US00RE48599E

(19) United States
(12) Reissued Patent
Podack et al.

(10) Patent Number: US RE48,599 E
(45) Date of Reissued Patent: Jun. 22, 2021

(54) COMPOSITIONS COMPRISING TLIA-IG FUSION PROTEIN FOR THE REGULATION OF T REGULATORY CELLS, AND METHODS FOR THEIR USE

(71) Applicant: University of Miami, Miami, FL (US)

(72) Inventors: Eckhard R. Podack, Coconut Grove, FL (US); Taylor H. Schreiber, Miami, FL (US); Samia Q. Khan, Miami, FL (US)

(73) Assignee: University of Miami, Miami, FL (US)

(21) Appl. No.: 16/366,676

(22) Filed: Mar. 27, 2019

Related U.S. Patent Documents

Reissue of:
(64) Patent No.: 9,603,925
Issued: Mar. 28, 2017
Appl. No.: 14/185,295
Filed: Feb. 20, 2014

U.S. Applications:
(63) Continuation of application No. 14/151,497, filed on Jan. 9, 2014, now abandoned.

(60) Provisional application No. 61/843,558, filed on Jul. 8, 2013, provisional application No. 61/842,127, filed on Jul. 2, 2013, provisional application No. 61/753,634, filed on Jan. 17, 2013, provisional application No. 61/750,672, filed on Jan. 9, 2013.

(51) Int. Cl.

| | |
|---|---|
| ***A61K 39/395*** | (2006.01) |
| ***C07K 14/52*** | (2006.01) |
| ***C07K 14/525*** | (2006.01) |
| ***A61K 38/20*** | (2006.01) |
| ***C07K 14/55*** | (2006.01) |
| ***A61K 31/7088*** | (2006.01) |
| ***A61K 31/436*** | (2006.01) |
| *C07K 16/24* | (2006.01) |

(52) U.S. Cl.
CPC ..... *A61K 39/3955* (2013.01); *A61K 31/436* (2013.01); *A61K 31/7088* (2013.01); *A61K 38/20* (2013.01); *A61K 38/2013* (2013.01); *A61K 39/395* (2013.01); *C07K 14/55* (2013.01); *C07K 14/52* (2013.01); *C07K 16/246* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 4,190,495 | A | 2/1980 | Curtiss, III |
| 4,376,110 | A | 3/1983 | David et al. |
| 4,518,584 | A | 5/1985 | Mark et al. |
| 4,575,013 | A | 3/1986 | Bartley |
| 4,654,307 | A | 3/1987 | Morgan |
| 4,719,179 | A | 1/1988 | Barany |
| 4,737,462 | A | 4/1988 | Mark et al. |
| 4,745,051 | A | 5/1988 | Smith et al. |
| 4,761,367 | A | 8/1988 | Edgell et al. |
| 4,870,009 | A | 9/1989 | Evans et al. |
| 4,952,496 | A | 8/1990 | Studier et al. |
| 5,093,246 | A | 3/1992 | Cech et al. |
| 5,109,124 | A | 4/1992 | Ramachandran et al. |
| 5,118,627 | A | 6/1992 | Browne |
| 5,122,463 | A | 6/1992 | Varshavsky et al. |
| 5,168,062 | A | 12/1992 | Stinski |
| 5,169,784 | A | 12/1992 | Summers et al. |
| 5,173,403 | A | 12/1992 | Tang et al. |
| 5,175,269 | A | 12/1992 | Stavrianopoulos |
| 5,176,996 | A | 1/1993 | Hogan et al. |
| 5,187,153 | A | 2/1993 | Cordell et al. |
| 5,198,343 | A | 3/1993 | DeGryse |
| 5,204,254 | A | 4/1993 | Schmid et al. |
| 5,212,058 | A | 5/1993 | Baker et al. |
| 5,212,286 | A | 5/1993 | Lewicki et al. |
| 5,215,907 | A | 6/1993 | Tang et al. |
| 5,218,088 | A | 6/1993 | Gorenstein et al. |
| 5,220,013 | A | 6/1993 | Ponte et al. |
| 5,223,483 | A | 6/1993 | Thomas et al. |
| 5,229,279 | A | 7/1993 | Peoples et al. |
| 5,242,687 | A | 9/1993 | Tykocinski et al. |
| 5,243,041 | A | 9/1993 | Fernandez-Pol |
| 5,244,805 | A | 9/1993 | Miller |
| 5,256,775 | A | 10/1993 | Froehler |
| 5,264,564 | A | 11/1993 | Matteucci |
| 5,266,317 | A | 11/1993 | Tomalski et al. |
| 5,278,050 | A | 1/1994 | Summers |
| 5,362,718 | A | 11/1994 | Skotnicki et al. |
| 5,434,065 | A | 7/1995 | Mahan et al. |
| 5,510,099 | A | 4/1996 | Short et al. |
| 5,567,440 | A | 10/1996 | Hubbell et al. |
| 5,656,481 | A | 8/1997 | Baetge et al. |
| 5,693,622 | A | 12/1997 | Wolff et al. |
| 5,700,657 | A | 12/1997 | Beaudry et al. |

(Continued)

FOREIGN PATENT DOCUMENTS

| | | |
|---|---|---|
| CA | 2451138 | 1/2003 |
| CN | 101253199 | 8/2008 |
| EP | 1405645 | 4/2004 |
| EP | 1246925 | 5/2008 |
| JP | 2009505678 | 2/2009 |

(Continued)

OTHER PUBLICATIONS

Lo, K.-M. et al. Protein Eng. (1998), 11(6); 495-500.*
Czajkowsky, D. M., et al. EMBO Mol. Med. (2012), 4(10); 1015-1028.*

(Continued)

*Primary Examiner* — Kevin S Orwig
(74) *Attorney, Agent, or Firm* — Morgan, Lewis & Bockius LLP

(57) ABSTRACT

Compositions comprising TL1A-Ig fusion proteins and methods of their use, e.g., for the treatment of diseases and disorders associated with antigen-specific immune responses, are described. Also described are combination therapies that include the administration of a TNFRSF25 agonist and an interleukin (e.g., IL-2) and/or an mTOR inhibitor (e.g., rapamycin).

30 Claims, 17 Drawing Sheets

Specification includes a Sequence Listing.

(56) References Cited

U.S. PATENT DOCUMENTS

| | | | |
|---|---|---|---|
| 5,714,323 | A | 2/1998 | Ohshima et al. |
| 5,773,246 | A | 6/1998 | Keene et al. |
| 5,859,208 | A | 1/1999 | Fiddes et al. |
| 5,955,056 | A | 9/1999 | Short et al. |
| 5,985,644 | A | 11/1999 | Roseman et al. |
| 6,254,874 | B1 | 7/2001 | Mekalanos et al. |
| 6,534,061 | B1 | 3/2003 | Goddard et al. |
| 6,713,061 | B1 | 3/2004 | Yu et al. |
| 7,226,617 | B2 | 6/2007 | Ding et al. |
| 7,300,774 | B1 | 11/2007 | Kornbluth |
| 7,357,927 | B2 | 4/2008 | Yu et al. |
| 7,385,032 | B2 | 6/2008 | Tschopp |
| 7,723,454 | B2 | 5/2010 | Keller et al. |
| 7,736,657 | B2 | 6/2010 | Gaide et al. |
| 2002/0009773 | A1 | 1/2002 | Yu |
| 2002/0015703 | A1 | 2/2002 | Rennert |
| 2002/0111325 | A1 | 8/2002 | Li et al. |
| 2002/0150534 | A1 | 10/2002 | Yu et al. |
| 2003/0092044 | A1 | 5/2003 | Goddard et al. |
| 2003/0129189 | A1 | 7/2003 | Yu et al. |
| 2003/0170203 | A1 | 9/2003 | Yu et al. |
| 2004/0013655 | A1 | 1/2004 | Shiozawa et al. |
| 2004/0156847 | A1 | 8/2004 | Miura et al. |
| 2005/0123536 | A1 | 6/2005 | Law et al. |
| 2005/0158831 | A1 | 7/2005 | Kornbluth |
| 2005/0282223 | A1 | 12/2005 | Tittle et al. |
| 2006/0233751 | A1 | 10/2006 | Bluestone et al. |
| 2007/0128184 | A1 | 6/2007 | Podack et al. |
| 2008/0003221 | A1 | 1/2008 | Podack et al. |
| 2008/0233119 | A2 | 9/2008 | Podack |
| 2009/0317388 | A1 | 12/2009 | Burkly et al. |
| 2011/0243951 | A1 | 10/2011 | Podack et al. |
| 2012/0029472 | A1 | 2/2012 | Podack et al. |
| 2012/0135011 | A1 | 5/2012 | Podack et al. |
| 2012/0263718 | A1 | 10/2012 | Siegel et al. |
| 2012/0321645 | A1 | 12/2012 | Podack et al. |
| 2012/0328559 | A1 | 12/2012 | Podack et al. |
| 2013/0142793 | A1 | 6/2013 | Ledbetter et al. |
| 2013/0211051 | A1 | 8/2013 | Sun et al. |
| 2014/0193410 | A1 | 7/2014 | Podack et al. |
| 2016/0015779 | A1 | 1/2016 | Podack |

FOREIGN PATENT DOCUMENTS

| | | |
|---|---|---|
| JP | 2011528562 | 11/2011 |
| WO | WO 1989007142 | 8/1989 |
| WO | WO 1991013160 | 9/1991 |
| WO | WO 1993001286 | 1/1993 |
| WO | WO 1994009010 | 4/1994 |
| WO | WO 1995016691 | 6/1995 |
| WO | WO 1995030762 | 11/1995 |
| WO | WO 1996001899 | 1/1996 |
| WO | WO 1996039154 | 12/1996 |
| WO | WO 1996041807 | 12/1996 |
| WO | WO 1997003211 | 1/1997 |
| WO | WO 1998002441 | 1/1998 |
| WO | WO 1999015530 | 4/1999 |
| WO | WO 1999023105 | 5/1999 |
| WO | WO 1999043839 | 9/1999 |
| WO | WO 2000064465 | 11/2000 |
| WO | WO 2001014387 | 3/2001 |
| WO | WO 2001035995 | 5/2001 |
| WO | WO 2001085207 | 11/2001 |
| WO | WO 2002011767 | 2/2002 |
| WO | WO 2002094192 | 11/2002 |
| WO | WO 2002100345 | 12/2002 |
| WO | WO 2003000286 | 1/2003 |
| WO | WO 2003039491 | 5/2003 |
| WO | WO 2003043583 | 5/2003 |
| WO | WO 2003068977 | 8/2003 |
| WO | WO 2005018571 | 3/2005 |
| WO | WO 2006127900 | 11/2006 |
| WO | WO 2007027751 | 3/2007 |
| WO | WO 2007041317 | 4/2007 |
| WO | WO 2010010051 | 1/2010 |
| WO | WO 2011017303 | 2/2011 |
| WO | WO 2012055083 | 5/2012 |
| WO | WO2012055083 A1 | 5/2012 |
| WO | WO 2012170072 | 12/2012 |

OTHER PUBLICATIONS

"TNFRSF25" entry in National Library of Medicine—Medical Subject Headings, "Receptors, Tumor Necrosis Factor, Member 25,"' National Library of Medicine [online], 2013 [retrieved on May 3, 2013]. Retrieved from the Internet: < URL: http://www.nlm.nih.gov/cgi/mesh/2013/MB_cgi?mode=&index=23859&field=all&H M=&II=&P A=&form=&input=>, 3 pages.

Bamias, et al., "Expression, localization, and functional activity of TL1A, a novel Th1-polarizing cytokine in inflanmlatory bowel disease," J Inmmnol., 171 (9):4868-4874, Nov. 1, 2003.

International Search Report and Written Opinion in International Application No. PCT/US2014/010874, dated Apr. 15, 2014, 13 pages.

Jin, et al., "TL1A/TNFSF15 directly induces proinflammatory cytokines, including TNFα, from CD3+CD161+ T cells to exacerbate gut inflammation," Mucosal Immunol., 6(5):886-889, Epub Dec. 19, 2012.

Mattes, et al., "IL-13 induces airways hyperreactivity independently of the IL-4R alpha chain in the allergic lung," J Jmmunol., 167(3):1683-1692, Aug. 1, 2001.

Meloni, et al., "Peripheral CD4+ CD25+ Trcg cell expansion in lung transplant recipients is not affected by calcineurin inhibitors," Int Immunopharmacol., 6(13-14):2002-10. Epub Aug. 17, 2006.

Meloni, et al., "Regulatory CD4+CD25+ T cells in the pelipheral blood of lung transplant recipients: correlation with transplant outcome," Transplantation, 77(5):762-766, Mar. 15, 2004.

Papadakis, et al., "Dominant role for TL1A/DR3 pathway in IL-12 plus IL-18-inducd IFN-gamma production by peripheral blood and mucosal CCR9+ T lymphocytes," J Immunol., 174(8):4985-4990, Apr. 15, 2005.

Papadakis, et al., "TLIA synergizes with IL-12 and IL-18 to enhance IFN-gamma production in human T cells and NK cells," J Immunol., 172(11):7002-7007, Jun. 1, 2004.

Pappu, et al., "TL1A-DR3 interaction regulates Thl7 cell function and Th 17-mediated autoimmune disease," J Exp Med., 205(5):1049-1062, Epub Apr. 14, 2008.

Prehn, et al., "Potential role for TL1A, the new TNF-family member and potent costimulator of IFN-gamma, in mucosal inflammation," Clin Immunol., 112(1):66-77, Jul. 2004.

Purello-D'Ambrosio, et al., "Effect of fluticasone propionate on soluble CD30 release in patients with severe allergic asthma," J Investig Allergol Clin Immunol., 10(5):283-285, Sep.-Oct. 2000.

R&D Systems, "Adiponectin/Acrp30: Products," R&D Systems [online], as appeared on Jan. 26, 2013 [retrieved on Sep. 9, 2014]. Retrieved from the Internet: < Url: http://web.archive.org/web/20130126225534/http://rndsystems.com/product_results.aspx?m=1034>, 2 pages.

Sánchez-Fueyo, et al., "CD4+CD25+ regulatory T cells in transplantation tolerance," Inmunologia, 23(2):231-238, Apr.-Jun. 2004.

Schreiber, et al., "T cell costimulation by TNFR superfamily (TNFRSF)4 and TNFRSF25 in the context of vaccination," J Immunol., 189(7):3311-3318, Epub Sep. 5, 2012.

Schreiber, et al., "Therapeutic Treg expansion in mice by TNFRSF25 prevents allergic lung inflammation," J Clinic Invest., 120(10):3629-3644, Oct. 2010.

Screaton, et al., "LARD: a new lymphoid-specific death domain containing receptor regulated by alternative pre-mRNA splicing," Proc Natl Acad Sci USA, 94(9):4615-4619, Apr. 29, 1997.

Takedatsu, et al., "TL1A (TNFSF15) regulates the development of chronic colitis by modulating both T-helper 1 and T-helper 17 activation," Gastroenterology, 135(2):552-567, Epub May 7, 2008.

Schreiber et al., "The role of TNFRSF25:TNFSF15 in disease . . . and health?" Adv Exp Med Biol., 691:289-298, 2011.

International Search Report and Written Opinion in International Application No. PCT/US2014/010874, mailed Apr. 15, 2014, 13 pages.

(56) References Cited

OTHER PUBLICATIONS

Schreiber et al., "Therapeutic Treg expansion in mice by TNFRSF25 prevents allergic lung inflammation," J Clinic Invest, Oct. 2010, 120(10):3629-36240.
Akbari et al., "Essential role of NKT cells producing IL-4 and IL-13 in the development of allergen-induced airway hyperreactivity," *Nat Med.*, 9(5):582-588, Mar. 31, 2003.
Al Lamki et al., "TL1A both promotes and protects from renal inflammation and injury," *J Am Soc Nephrol.*, 19(5):953-960, Epub Feb. 20, 2008.
Al-Lamki et al., "Expression of silencer of death domains and death-receptor-3 in normal human kidney and in rejecting renal transplants," *Am J Pathol.*, 163(2):401-411, Aug. 2003.
Allan et al., "CD4+ T-regulatory cells: toward therapy for human diseases," *Immunol Rev.*, 223:391-421, Jun. 2008.
Benghiat et al., "Critical influence of natural regulatory CD25+ T cells on the fate of allografts in the absence of immunosuppression," *Transplantation*, 79(6):648-654, Mar. 27, 2005.
Berg et al., "ACRP30/adiponectin: an adipokine regulating glucose and lipid metabolism," *Trends Endocrinol Metab.*, 13(2):84-89, Mar. 2002.
Bodmer et al., "TRAMP, a novel apoptosis-mediating receptor with sequence homology to tumor necrosis factor receptor 1 and Fas(Apo-1/CD95)," *Immunity.*, 6(1):79-88, Jan. 1997.
Branch, "A good antisense molecule is hard to find," *Trends Biochem Sci.*, 23(2):45-50, Feb. 1998.
Bull et al., "The Death Receptor 3-TNF-like protein 1A pathway drives adverse bone pathology in inflammatory arthritis," *J Exp Med.*, 205(11):2457-2464, Epub Sep. 29, 2008.
Chen, "TGF-Betal Regulation of chemokine receptors in rat microglia and human macrophages," University of Florida, 2001, 119 pages [Dissertation].
Chew et al., "A novel secreted splice variant of vascular endothelial cell growth inhibitor," *FASEB J.*, 16(7):742-744. Epub Mar. 26, 2002.
Chinnaiyan et al., "Signal transduction by DR3, a death domain-containing receptor related to TNFR-1 and CD95," *Science.*, 274(5289):990-992, Nov. 8, 1996.
Cobrin and Abreu, "Defects in mucosal immunity leading to Crohn's disease," *Immunol Rev.*, 206:277-295, Aug. 2005.
Cui, "Requirement for Valpha14 NKT cells in IL-12-mediated rejection of tumors," *Science.*, 278(5343):1623-1626, Nov. 28, 1997.
Del Prete et al., CD30-mediated signaling promotes the development of human T helper type 2-like T cells, *J Exp Med.*, 182(6):1655-1661, Dec. 1, 1995.
Deyev et al.,"TNFR25 expression on CD4(+)CD25(+) T cells; Down modulation of regulatory activity," Blood, 108(11)Pt1:903A, Nov. 16, 2006.
Fang, "Death receptor 3 (TNFR-SF25) delivers a late-acting costimulatory signal for Th2 cytokine production during the development of allergic asthma" University of Miami, Dec. 2004, 153 pages [Dissertation].
Grunig et al., "Requirement for IL-13 independently of IL-4 in experimental asthma," *Science.*, 282(5397):2261-2263, Dec. 18, 1998.
Harlin et al., "Tcr-independent CD30 signaling selectively induces IL-13 production via a TNF receptor-associated factor/p38 mitogen-activated protein kinase-dependent mechanism," *J Immunol.*, 169(5):2451-2459, Sep. 1, 2002.
Huang, "Structural chemistry and therapeutic intervention of protein-protein interactions in immune response, human immunodeficiency virus entry, and apoptosis," *Pharmacol Ther.*, 86(3):201-215, Jun. 2000.
Jin et al., "TL1A/TNFSF15 directly induces proinflammatroy cytokines, including TNF⊕, from CD3+CD161+ T cells to exacerbate gut inflammation," *Mucosal Immunol.*, 6(5):886-899, Epub Dec. 19, 2012.
Khan et al., "Cloning, expression, and functional characterization of TL1A-Ig;" *J Immunol.*, 190(4):1540-1550, Epub Jan. 14, 2013.
Kitson et al., "A death-domain-containing receptor that mediates apoptosis," *Nature*, 384(6607):372-375, Nov. 28, 1996.
Leonard et al., "Allergen-induced CD30 expression on T cells of atopic asthmatics," *Clin Exp Allergy.*, 27(7):780-786, Jul. 1997.
Li et al., "Effects of Th2 cytokines on chemokine expression in the lung: IL-13 potently induces eotaxin expression by airway epithelial cells," *J Immunol.*, 162(5):2477-2487, Mar. 1, 1999.
Marsters et al., "Apo-3, a new member of the tumor necrosis factor receptor family, contains a death domain and activates apoptosis and NF-kappa B," *Curr Biol.*, 6(12):1669-1676, Dec. 1, 1996.
Migone et al., "TL1A is a TNF-like ligand for DR3 and TR6/DcR3 and functions as a T cell costimulator," *Immunity.*, 16(3):479-492, Mar. 2002.
Miller et al., "4-1BB-specific monoclonal antibody promotes the generation of tumor-specific immune responses by direct activation of CD8 T cells in a CD40-dependent manner," *J Immunol.*, 169(4):1792-1800, Aug. 15, 2002.
Nam et al., "CD30 deficiency diminishes airway eosinophillia in a mouse model of pulmonary inflammation," *FASEB J.*, 17(7): C14, Abstract 30.24, May 6-10, 2003, Denver, Colorado.
Shuford et al., "4-1BB costimulatory signals preferentially induce CD8+ T cell proliferation and lead to the amplification in vivo of cytotoxic T cell responses," *J Exp Med.* 186(1):47-55, Jul. 7, 1997.
Takedatsu et al., "TL1A (TNFSF15) regulated the development of chronic colitis by modulating both T-helper 1 and T-helper 17 activation," *Gastroenterology*, 135(2):552-567, Epub May 7, 2008.
Tan et al., "Characterization of a novel TNF-like ligand and recently described TNF ligand and TNF receptor superfamily genes and their constitutive and inducible expression in hematopoietic and non-hematopoietic cells," *Gene*, 204(1-2):35-46, Dec. 19, 1997.
Wang et al., "DR3 regulates negative selection during thymocyte development," *Mol Cell Biol.*, 21(10):3451-3461, May 2001.
Wen et al., "4-1BB ligand-mediated costimulation of human T cells induces CD4 and CD8 T cell expansion, cytokine production, and the development of cytolytic effector function," *J Immunol.*, 168(10):4897-4906, May 15, 2002.
Wen et al., "TL1A-induced NF-kappaB activation and c-IAP2 production prevent DR3-mediated apoptosis in TF-1 cells," *J Biol Chem.* 278(40):39251-39258, Epub Jul. 25, 2003.
Wills-Karp et al., "Interleukin-13: central mediator of allergic asthma," *Science*, 282(5397):2258-2261, Dec. 18, 1998.
Wolf et al., "Tregs expanded in vivo by TNFRSF25 agonists promote cardiac allograft survival," *Transplantation.*, 94(6):569-574, Sep. 27, 2012.
Zhang et al., "Role of TL1A in the pathogenesis of rheumatoid arthritis," *J Immunol.*, 183(8):5350-5357, Epub Sep. 28, 2009.
Pulendran, "Modulating vaccine responses with dendritic cells and Toll-like receptors," Immunol Rev., 199:227-250, Jun. 2004.
Watts, "TNF/TNFR family members in costimulation of T cell responses," Annu Rev Immunol., 23:23-68, 2005.
Neuhaus et al., "mTOR inhibitors: an overview," Liver Transpl., 7(6):473-484, Jun. 2001.
Reddy, "TNFRSF25 agonistic antibody and galectin-9 combination therapy controls herpes simplex virus-induced immunoinflammatory lesions," J Virol., 86(19):10606-10620, Epub Jul. 18, 2012.
International Preliminary Report on Patentability for PCT/US2014/010874, mailed Jul. 23, 2015, 9 pages.
Kim et al., "Treatment with agonistic DR3 antibody results in expansion of donor Tregs and reduced graft-versus-host disease," Blood, 126(4):546-557, Epub Jun. 10, 2015.
Schreiber et al., "Response to Taraban, Ferdinand, and Al-Shamkhani," J Clin Invest., 121(2):465-465, Feb. 1, 2011.
European Search Report for Application No. 14737866.5, dated Sep. 9, 2016, 8 pages.

* cited by examiner

FIG. 7A
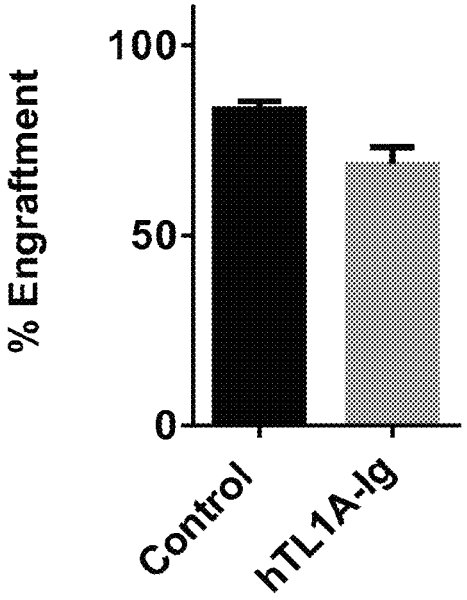
FIG. 7B
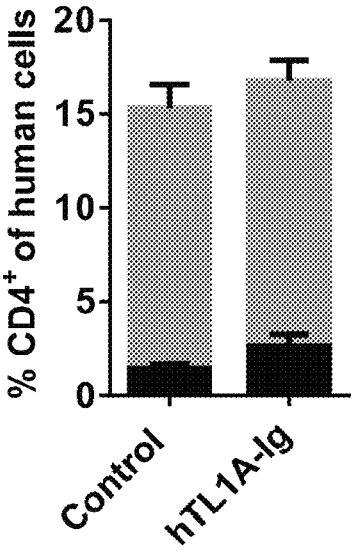
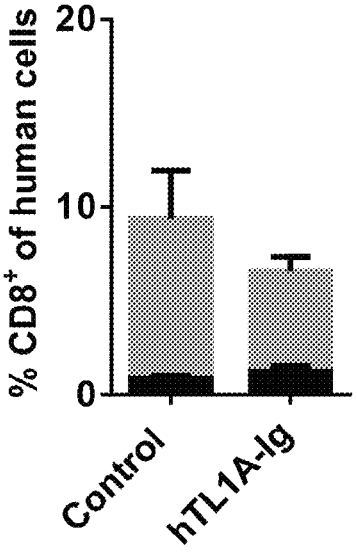
FIG. 7C
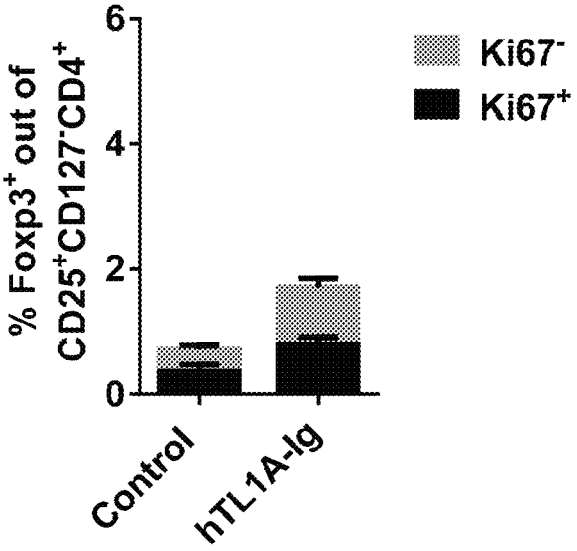
FIG. 7D

FIG. 8A
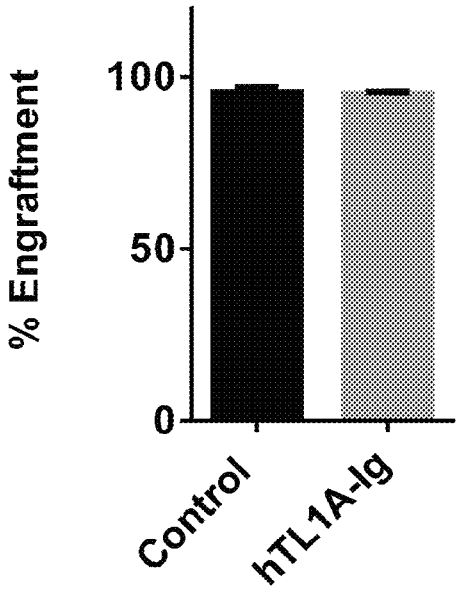
FIG. 8B
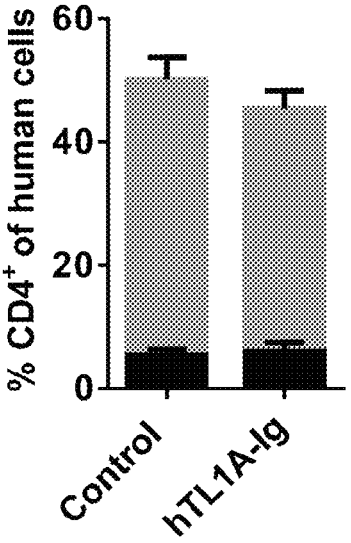
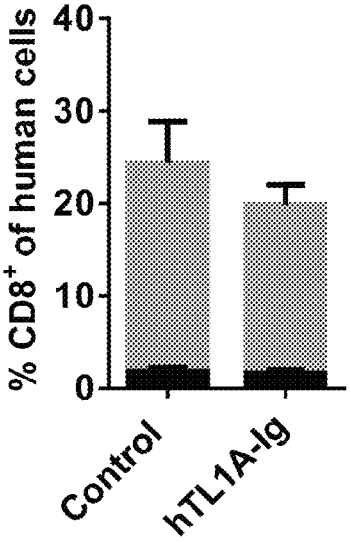
FIG. 8C
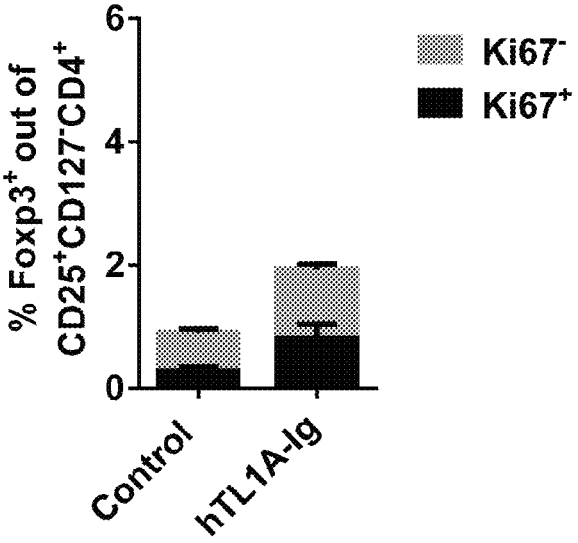
FIG. 8D

FIG. 9A
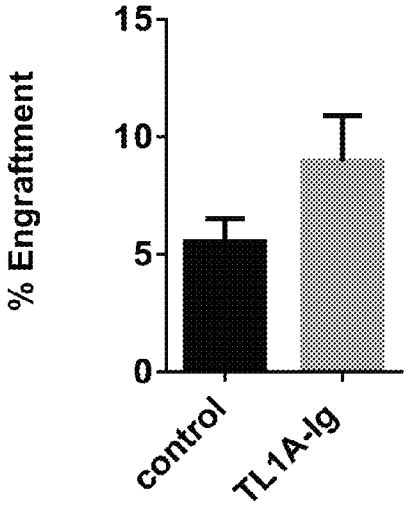
FIG. 9B
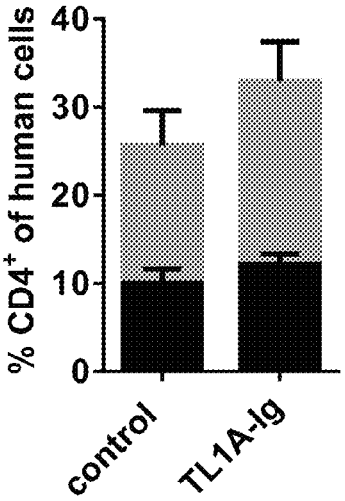
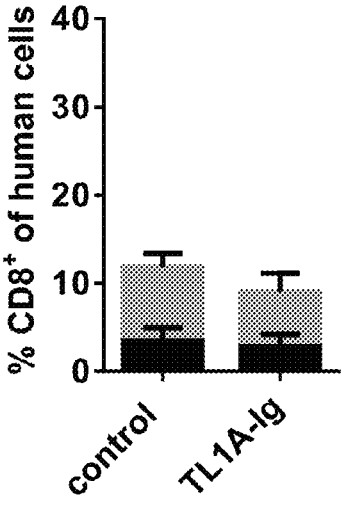
FIG. 9C
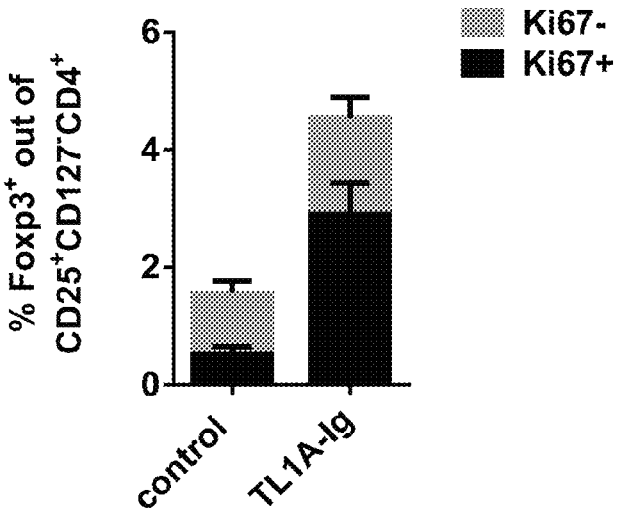
FIG. 9D

FIG. 13A
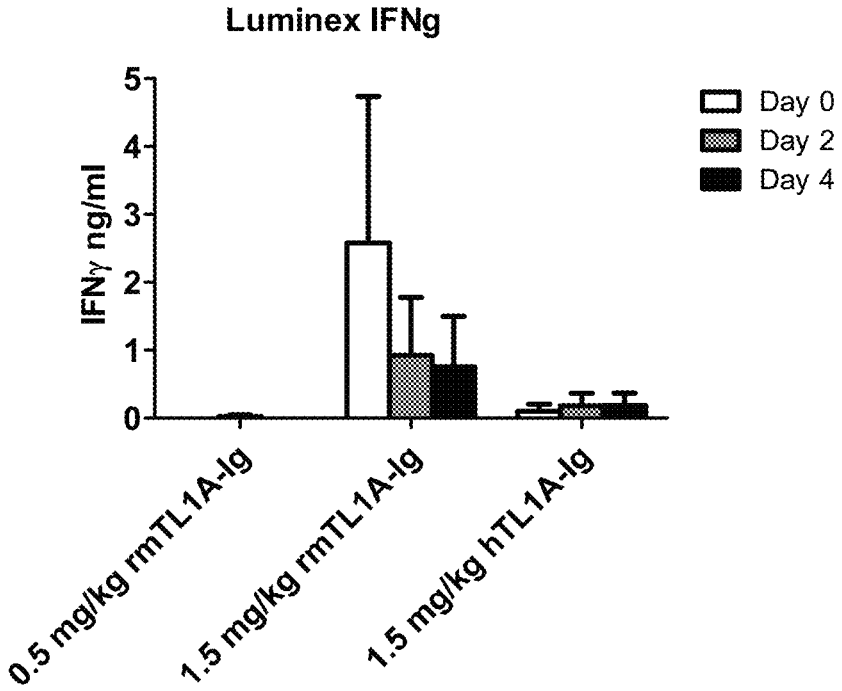
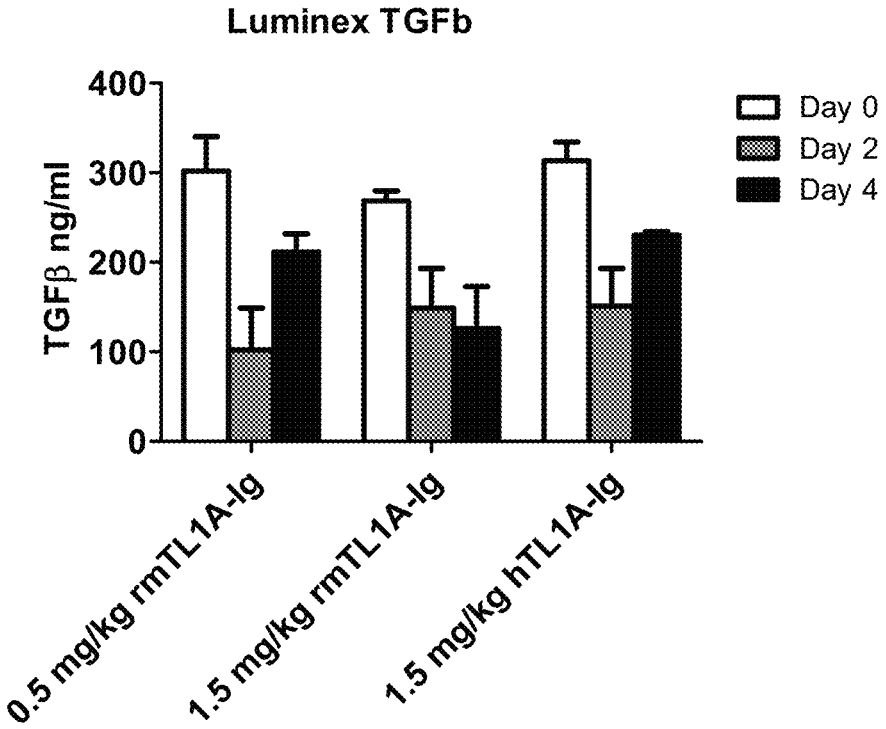
FIG. 13B

COMPOSITIONS COMPRISING TLIA-IG FUSION PROTEIN FOR THE REGULATION OF T REGULATORY CELLS, AND METHODS FOR THEIR USE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED APPLICATIONS

This application is a continuation of U.S. application Ser. No. 14/151,497, filed Jan. 9, 2014, which claims the benefit of priority to U.S. provisional application Ser. Nos. 61/750,672, filed Jan. 9, 2013; 61/753,634, filed Jan. 17, 2013; 61/842,127, filed Jul. 2, 2013; and 61/843,558, filed Jul. 8, 2013; the entire contents of each are incorporated by reference in their entireties.

STATEMENT REGARDING FEDERALLY SPONSORED RESEARCH OR DEVELOPMENT

This invention was made with government support under 5P01CA109094 awarded by the National Institutes of Health. The government has certain rights in the invention.

TECHNICAL FIELD

This disclosure relates to the fields of molecular biology and immunology.

BACKGROUND

Stimulation of tumor necrosis factor receptor superfamily, member 25 (TNFRSF25) in vivo with its natural ligand TNFSF15 (also known as TL1A), facilitates selective proliferation of Treg in mice and suppression of immunopathology in allergic lung inflammation, allogeneic heart transplantation and HSV-1 mediated ocular inflammation. Progress in translating Treg therapy in humans has been slow, however, and thus far limited to ex vivo cell culture methodologies. Furthermore, such therapies must also be safe and avoid dangerous side effects, such as susceptibilities to inflammatory bowel disease (IBD). Prolonged stimulation with certain TNFRSF25 agonists have been known to cause harmful side effects in vivo, including, for example, increased inflammation in mouse models of asthma, inflammatory bowel disease and arthritis. Thus improved therapies that are safe and effective for Treg therapy in humans are needed.

SUMMARY

As discussed above, safe and effective therapies for so treating autoimmune diseases and disorders, establishing tolerance to allogeneic solid organ transplantation, and for modulating other antigen-specific immune responses, particularly in human patients, are needed in the art. The present disclosure provides these and other related advantages.

In some embodiments, provided here is an isolated or recombinant nucleic acid comprising a polynucleotide sequence which encodes a fusion protein, the fusion protein comprising (a) a first polypeptide comprising a polypeptide sequence that specifically binds to Tumor Necrosis Factor Receptor Superfamily, Member 25 (TNFRSF25), and (b) a second polypeptide comprising an immunoglobulin (Ig) polypeptide; or a complementary polynucleotide sequence thereof. In some embodiments, the first polypeptide comprises the extracellular domain of a human TL1A polypeptide or a fragment thereof, wherein the fragment is capable of specifically binding to TNFRSF25. In some embodiments, the nucleic acid encodes a monomeric fusion protein capable of forming a fusion protein homomultimer. In some embodiments, the homomultimer is a dimer of trimers. In some embodiments, the nucleic acid encodes a polypeptide that, when administered to a human in need thereof, reduces the frequency of naive CD4 T cells in the human. In some embodiments, the second polypeptide comprises one or more of a hinge region, a CH2 domain, and a CH3 domain of an IgG polypeptide (e.g., IgG1). In some embodiments, the second polypeptide comprises two or more of a hinge region, a CH2 domain, and a CH3 domain of an IgG polypeptide. In some embodiments, the second polypeptide comprises a hinge region, a CH2 domain, and a CH3 domain of an IgG polypeptide. In some embodiments, the second polypeptide comprises the polypeptide sequence of SEQ ID NO: 14. In some embodiments, the first polypeptide comprises a polypeptide sequence that has at least 90% sequence identity to SEQ ID NO: 12. In some embodiments, the first polypeptide comprises a polypeptide sequence that has at least 95% sequence identity to SEQ ID NO: 12. In some embodiments, the first polypeptide comprises a polypeptide sequence that has at least 97%, 98%, or 99% sequence identity to SEQ ID NO: 12. In some embodiments, the first polypeptide comprises the sequence of SEQ ID NO: 12. In some embodiments, the first polypeptide consists of the sequence of SEQ ID NO: 12. In some embodiments, the nucleic acid encodes a fusion protein comprising SEQ ID NO: 12 and SEQ ID NO: 14. In some embodiments, the nucleic acid encodes a fusion protein comprising SEQ ID NO: 16. In some embodiments, the nucleic acid encodes a fusion protein consisting of SEQ ID NO: 16. In some embodiments, the nucleic acid comprising a sequence that encodes a fusion protein further comprises a nucleotide sequence that encodes a signal peptide. In some embodiments, the nucleic acid further comprises a nucleotide sequence that encodes a secretory and/or signal peptide operably linked to the fusion protein. In some embodiments, the fusion protein is secreted from the host cell as a fusion protein homomultimer (e.g., a dimer of trimers).

Also provided herein is a vector comprising a nucleic acid described above (e.g., an isolated or recombinant nucleic acid comprising a polynucleotide sequence which encodes a fusion protein, the fusion protein comprising (a) a first polypeptide comprising a polypeptide sequence that specifically binds to TNFRSF25, and (b) a second polypeptide comprising an Ig polypeptide; or a complementary polynucleotide sequence thereof). In some embodiments, the nucleic acid is operably linked to a promoter. In some embodiments, the vector is an expression vector. In some embodiments, the vector is a plasmid vector. In some embodiments, also provided herein is an isolated or recombinant host cell comprising the vector described above (e.g., a vector comprising an isolated or recombinant nucleic acid comprising a polynucleotide sequence which encodes a fusion protein, the fusion protein comprising (a) a first polypeptide comprising a polypeptide sequence that specifically binds to TNFRSF25, and (b) a second polypeptide comprising an Ig polypeptide; or a complementary polynucleotide sequence thereof). In some embodiments, also provided herein is an isolated or recombinant host cell transfected with any of the nucleic acids described above (e.g., an isolated or recombinant nucleic acid comprising a polynucleotide sequence which encodes a fusion protein, the fusion protein comprising (a) a first polypeptide comprising a polypeptide sequence that specifically binds to TNFRSF25, and (b) a second polypeptide comprising an Ig polypeptide; or a complementary polynucleotide sequence thereof), wherein the host cell is capable of expressing the fusion protein. In some embodiments, the host cell is a eukaryotic cell.

Also provided herein is a method of producing a polypeptide, comprising: (a) introducing into a population of cells a nucleic acid described above (e.g., an isolated or recombinant nucleic acid comprising a polynucleotide sequence which encodes a fusion protein, the fusion protein comprising (a) a first polypeptide comprising a polypeptide sequence that specifically binds to TNFRSF25, and (b) a second polypeptide comprising an Ig polypeptide; or a complementary polynucleotide sequence thereof), wherein the nucleic acid is operatively linked to a regulatory sequence effective to produce the polypeptide encoded by the nucleic acid; and (b) culturing the cells in a culture medium to produce the polypeptide. In some embodiments, the method further comprises: (c) isolating the polypeptide from the cells or culture medium. In some embodiments, the polypeptide is a fusion protein. In some embodiments, the nucleic acid further comprises a third nucleotide sequence that encodes a secretory or signal peptide operably linked to the fusion protein. In some embodiments, the fusion protein is secreted from the host cell as a fusion protein homomultimer (e.g., dimer of trimers). In some embodiments, the fusion protein homomultimer is recovered from the culture medium. In some embodiments, the fusion protein is recovered from the culture medium, host cell, or host cell periplasm. In some embodiments, the fusion protein homomultimer comprises one or more covalent disulfide bonds between a cysteine residue of the first fusion protein and at least one cysteine residue of one or more additional fusion proteins.

Also provided herein is a composition comprising a human TL1A-Ig fusion protein, the fusion protein comprising (a) a first polypeptide comprising a polypeptide that specifically binds to TNFRSF25; and (b) a second polypeptide comprising an Ig polypeptide. In some embodiments, the first polypeptide comprises the extracellular domain of a human TL1A polypeptide or a fragment thereof, wherein the fragment is capable of specifically binding to TNFRSF25. In some embodiments, the composition, when administered to a human in need thereof, reduces the frequency of naive CD4 T cells in the human. In some embodiments, the first polypeptide comprises a polypeptide sequence that has at least 90% sequence identity to SEQ ID NO: 12. In some embodiments, the first polypeptide comprises a sequence that has at least 95% sequence identity to SEQ ID NO: 12. In some embodiments, the first polypeptide comprises a sequence that has at least 98% sequence identity to SEQ ID NO: 12. In some embodiments, the first polypeptide comprises a sequence that has at least 99% or 100% sequence identity to SEQ ID NO: 12. In some embodiments, the fusion protein is a homomultimer. In some embodiments, the fusion protein is a dimer of trimers. In some embodiments, the Ig polypeptide comprises one or more of a hinge region, a CH2 domain, and a CH3 domain of an IgG polypeptide. In some embodiments, the Ig polypeptide comprises two or more of a hinge region, a CH2 domain, and a CH3 domain of an IgG polypeptide. In some embodiments, the Ig polypeptide comprises a hinge region, a CH2 domain, and a CH3 domain of an IgG polypeptide. In some embodiments, the Ig polypeptide comprises an amino acid sequence that has at least 90% sequence identity to SEQ ID NO: 14. In some embodiments, the Ig polypeptide comprises an amino acid sequence that has at least 95% sequence identity to SEQ ID NO: 14. In some embodiments, the Ig polypeptide comprises an amino acid sequence that has at least 97% sequence identity to SEQ ID NO: 14. In some embodiments, the Ig polypeptide comprises an amino acid sequence that has at least 99% or 100% sequence identity to SEQ ID NO: 14. In some embodiments, the fusion protein comprises an amino acid sequence that has at least 90% sequence identity to SEQ ID NO: 16. In some embodiments, the fusion protein comprises an amino acid sequence that has at least 95% sequence identity to SEQ ID NO: 16. In some embodiments, the fusion protein comprises an amino acid sequence that has at least 97% sequence identity to SEQ ID NO: 16. In some embodiments, the fusion protein comprises an amino acid sequence that has at least 99% or 100% sequence identity to SEQ ID NO: 16. In some embodiments, the composition is characterized by enhanced in vivo efficacy compared to the first polypeptide when it is not coupled with an Ig polypeptide.

Also provided herein is a method of modulating an antigen-specific immune response in a human patient in need thereof, the method comprising: administering to the patient a composition described above (e.g., a composition comprising a human TL1A-Ig fusion protein, the fusion protein comprising (a) a first polypeptide comprising a polypeptide that specifically binds to TNFRSF25; and (b) a second polypeptide comprising an Ig polypeptide), wherein the composition is administered in an amount that comprises a therapeutically effective amount of the fusion protein. In some embodiments, the patient in need thereof is a patient selected from the group consisting of a patient undergoing or about to undergo induction therapy in preparation for a solid organ or stem cell transplant, a patient who is a solid organ or stem cell transplant recipient and is undergoing or is about to undergo maintenance therapy, a patient who is a solid organ or stem cell transplant recipient, an allergic patient; a patient who is receiving or about to receive a vaccine, a patient being treated or about to be treated with an immune checkpoint inhibitor (e.g., CTLA-4 or PD-1 inhibitor). In some embodiments, the therapeutically effective amount of the fusion protein is in a range of 0.1-10 milligrams per kilogram of body weight per day (mg/kg/day). In some embodiments, the therapeutically effective amount of the fusion protein is in a range of 0.5-5 mg/kg/day. In some embodiments, the therapeutically effective amount of the fusion protein is in a range of 1-2 mg/kg/day. In some embodiments, the composition reduces an antigen-specific immune response in the patient by at least 20%. In some embodiments, the method comprises multiple administrations of the composition to the patient. In some embodiments, the above compositions further comprise an effective amount of IL-2. In some embodiments, the effective amount of IL-2 is an amount that would induce suboptimal expansion of Treg cells if administered alone to a subject. In some embodiments, the effective amount of IL-2 is a dosage in the range of between 30,000 to 300,000 units per square meter per day. In some embodiments, the effective amount of IL-2 is 30,000 units per square meter per day. In some embodiments, the effective amount of IL-2 is 300,000 units per square meter per day. In some embodiments, any of the above compositions further comprise an effective amount of an mTOR inhibitor. In some embodiments, the mTOR inhibitor is selected from the group consisting of rapamycin (sirolimus), CI-779, everolimus ABT-578, tacrolimus, AP-23675, BEZ-235, OSI-027, QLT-0447, ABI-009, BC-210, salirasib, TAFA-93, deforolimus (AP-23573), temsirolimus, 2-(4-Amino-1-isopropyl-1H-pyrazolo[3,4-d]pyrimidin-3-yl)-1H-indol-5-ol (PP242), AP-23841, 32-deoxorapamycin, 16-pent-2-ynyloxy-32-deoxorapamycin, 16-pent-2-ynyloxy-32(S or R)-dihydro-rapamycin, 16-pent-2-ynyloxy-32(S or R)-dihydro-40-O-(2-hydroxyethyl)-rapamycin, 40-[3-hydroxy-2-(hydroxymethyl)-2-methylpropanoate]-rapamycin (CCI779), 40-epi-(tetrazolyl)-rapamycin (ABT578), biolimus-7, biolimus-9, and AP23464.

Also provided herein is a method of treating a disease or disorder associated with an antigen-specific immune response, or treating one or more symptoms of the disease or disorder, in a human patient in need thereof, the method comprising: administering to the patient a composition described above (e.g., a composition comprising a human TL1A-Ig fusion protein, the fusion protein comprising (a) a first polypeptide comprising a polypeptide that specifically binds to TNFRSF25; and (b) a second polypeptide comprising an Ig polypeptide), wherein the composition is administered in an amount that comprises a therapeutically effective amount of the fusion protein. In some embodiments, the therapeutically effective amount of the fusion protein is in a range of 0.1-10 mg/kg/day. In some embodiments, the therapeutically effective amount of the fusion protein is in a range of 0.5-5 mg/kg/day. In some embodiments, the therapeutically effective amount of the fusion protein is in a range of 1-2 mg/kg/day. In some embodiments, the disease or disorder is selected from the group consisting of autoimmune disease or disorder, transplant rejection, graft-versus-host disease, inflammation, asthma, allergies, and chronic infection. In some embodiments, the disease or disorder is asthma. In some embodiments, the method comprises multiple administrations of the composition to the patient. In some embodiments of the method of treating a disease or disorder associated with an antigen-specific immune response, the composition reduces an antigen-specific immune response in the patient by at least 20%. In some embodiments, the method of treating a disease or disorder associated with an antigen-specific immune response further comprises administering to the patient an effective amount of IL-2. In some embodiments, the effective amount of IL-2 is an amount that would induce suboptimal, or fail to induce, expansion of Treg cells if administered alone to the patient. In some embodiments, the effective amount of IL-2 is a dosage in the range of between 30,000 to 300,000 units per square meter per day. In some embodiments, the effective amount of IL-2 is 30,000 units per square meter per day. In some embodiments, the effective amount of IL-2 is 300,000 units per square meter per day. In some embodiments, the method of treating a disease or disorder associated with an antigen-specific immune response further comprises administering to the patient an effective amount of an mTOR inhibitor. In some embodiments, the mTOR inhibitor is selected from the group consisting of rapamycin (sirolimus), CI-779, everolimus ABT-578, tacrolimus, AP-23675, BEZ-235, OSI-027, QLT-0447, ABI-009, BC-210, salirasib, TAFA-93, deforolimus (AP-23573), temsirolimus, 2-(4-Amino-1-isopropyl-1H-pyrazolo [3,4-d]pyrimidin-3-yl)-1H-indol-5-ol (PP242), AP-23841, 32-deoxorapamycin, 16-pent-2-ynyloxy-32-deoxorapamycin, 16-pent-2-ynyloxy-32(S or R)-dihydro-rapamycin, 16-pent-2-ynyloxy-32(S or R)-dihydro-40-O-(2-hydroxyethyl)-rapamycin, 40-[3-hydroxy-2-(hydroxymethyl)-2-methylpropanoate]-rapamycin (CCI779), 40-epi-(tetrazolyl)-rapamycin (ABT578), biolimus-7, biolimus-9, and AP23464.

Also provided herein is a method of reducing the severity and/or frequency of an adverse event associated with a therapy that comprises the administration of a TNFRSF25 agonist, wherein the method of reducing the severity and/or frequency of the adverse event comprises administering to a patient in need thereof any of the compositions described above (e.g., a composition comprising a human TL1A-Ig fusion protein, the fusion protein comprising (a) a first polypeptide comprising a polypeptide that specifically binds to TNFRSF25; and (b) a second polypeptide comprising an Ig polypeptide, and/or an agonistic anti-TNFRSF25 antibody, and/or a small molecule agonist of TNFRSF25, and/or an interleukin or analog thereof (e.g., IL-2, IL-7, IL-15), and/or an mTOR inhibitor (e.g., rapamycin)) in a physiologically acceptable carrier. In some embodiments, the adverse event is the development of one or more symptoms of inflammatory bowel disease. In some embodiments, the adverse event is development of inflammatory bowel disease. In some embodiments, the adverse event is selected from the group consisting of weight loss, rash, diarrhea, myalgias, decreased platelet counts, elevated liver enzyme levels, and death. In some embodiments, the composition is administered to the patient in an amount that significantly increases proliferation of Treg cells in the patient following the administration. In some embodiments, the composition is administered to the patient in an amount that increases proliferation of Treg cells by at least two-fold in the patient following the administration. In some embodiments, the method comprises multiple administrations of the composition to the patient. In some embodiments, the disease or disorder is an autoimmune disease. In some embodiments, the autoimmune disease is selected from the group consisting of inflammatory bowel disease and rheumatoid arthritis. In some embodiments, the composition is formulated as a pharmaceutical preparation. In some embodiments, the above methods for reducing the severity and/or frequency of an adverse event further comprise administering to the patient an effective amount of IL-2. In some embodiments, the effective amount of IL-2 is an amount that would induce suboptimal, or fail to induce, expansion of Treg cells if administered alone to the patient. In some embodiments of the above methods of reducing the severity and/or frequency of an adverse event, the effective amount of IL-2 is a dosage in the range of between 30,000 to 300,000 units per square meter per day. In some embodiments, the effective amount of IL-2 is 30,000 units per square meter per day. In some embodiments, the effective amount of IL-2 is 300,000 units per square meter per day. In some embodiments, the above methods of reducing the severity and/or frequency of an adverse event further comprise administering to the patient an effective amount of an mTOR inhibitor. In some embodiments, the mTOR inhibitor is selected from the group consisting of rapamycin (sirolimus), CI-779, everolimus ABT-578, tacrolimus, AP-23675, BEZ-235, OSI-027, QLT-0447, ABI-009, BC-210, salirasib, TAFA-93, deforolimus (AP-23573), temsirolimus, 2-(4-Amino-1-isopropyl-1H-pyrazolo[3,4-d]pyrimidin-3-yl)-1H-indol-5-ol (PP242), AP-23841, 32-deoxorapamycin, 16-pent-2-ynyloxy-32-deoxorapamycin, 16-pent-2-ynyloxy-32(S or R)-dihydro-rapamycin, 16-pent-2-ynyloxy-32(S or R)-dihydro-40-O-(2-hydroxyethyl)-rapamycin, 40-[3-hydroxy-2-(hydroxymethyl)-2-methylpropanoate]-rapamycin (CCI779), 40-epi-(tetrazolyl)-rapamycin (ABT578), biolimus-7, biolimus-9, and AP23464.

Also provided herein is a pharmaceutical composition comprising: (a) any of the compositions described above (e.g., a composition comprising a human TL1A-Ig fusion protein, the fusion protein comprising (a) a first polypeptide comprising a polypeptide that specifically binds to TNFRSF25; and (b) a second polypeptide comprising an Ig polypeptide, and/or an agonistic anti-TNFRSF25 antibody, and/or a small molecule agonist of TNFRSF25, and/or an interleukin or analog thereof (e.g., IL-2, IL-7, IL-15), and/or an mTOR inhibitor (e.g., rapamycin)); and (b) a pharmaceutically acceptable carrier. In some embodiments, the pharmaceutical composition further comprises an effective amount of IL-2. In some embodiments, the effective amount of IL-2 is an amount that would induce suboptimal, or fail to induce, expansion of Treg cells if administered alone to the patient. In some embodiments, the effective amount of IL-2 is a dosage in the range of between 30,000 to 300,000 units per square meter per day. In some embodiments, the effective amount of IL-2 is 30,000 units per square meter per day. In some embodiments, the effective amount of IL-2 is 300,000 units per square meter per day.

Also provided herein are methods of modulating an antigen-specific immune response, and/or for treating a disease or disorder associated with an antigen-specific immune response, and/or for treating one or more symptoms of the disease or disorder, in a human patient in need thereof, the method comprising: administering to the patient a combination therapy comprising a TNFRSF25 agonist and an effective amount of interleukin 2 and/or an mTOR inhibitor. In some embodiments of this method, the TNFRSF25 agonist is a small molecule, an agonistic anti-TNFRSF25 antibody, or a TL1A fusion protein, as described herein. In some embodiments, the TL1A fusion protein is administered in an amount in a range of 0.1-10 mg/kg/day, 0.5-5 mg/kg/day, or 1-2 mg/kg/day. In some embodiments, the effective amount of IL-2 is an amount that would induce suboptimal, or fail to induce, expansion of Treg cells if administered alone to the patient. In some embodiments of the method, the effective amount of IL-2 is a dosage in the range of between 30,000 to 300,000 units per square meter per day. In some embodiments, the effective amount of IL-2 is 30,000 units per square meter per day. In some embodiments, the effective amount of IL-2 is 300,000 units per square meter per day. In some embodiments, the TNFRSF25 agonist and the effective amount of IL-2 are administered on the same day, together or separately. In some embodiments, the TNFRSF25 agonist and the effective amount of IL-2 are administered on different days. In some embodiments of the method, the combination therapy comprises a TNFRSF25 agonist and an effective amount of an mTOR inhibitor. In some embodiments, the mTOR inhibitor is administered in an amount in a range of 75 to 300 micrograms per kg body weight per day. In some embodiments, the TNFRSF25 agonist and the mTOR inhibitor are administered on the same day, together or separately. In some embodiments, the TNFRSF25 agonist and the mTOR inhibitor are administered on different days. In some embodiments of the above methods comprising a combination therapy, the disease or disorder is selected from the group consisting of autoimmune disease or disorder, transplant rejection, graft-versus-host disease, inflammation, asthma, allergies, and chronic infection. In some embodiments of these methods, the mTOR inhibitor is selected from the group consisting of rapamycin (sirolimus), CI-779, everolimus ABT-578, tacrolimus, AP-23675, BEZ-235, OSI-027, QLT-0447, ABI-009, BC-210, salirasib, TAFA-93, deforolimus (AP-23573), temsirolimus, 2-(4-Amino-1-isopropyl-1H-pyrazolo [3,4-d]pyrimidin-3-yl)-1H-indol-5-ol (PP242), AP-23841, 32-deoxorapamycin, 16-pent-2-ynyloxy-32-deoxorapamycin, 16-pent-2-ynyloxy-32(S or R)-dihydro-rapamycin, 16-pent-2-ynyloxy-32(S or R)-dihydro-40-O-(2-hydroxyethyl)-rapamycin, 40-[3-hydroxy-2-(hydroxymethyl)-2-methylpropanoate]-rapamycin (CCI779), 40-epi-(tetrazolyl)-rapamycin (ABT578), biolimus-7, biolimus-9, and AP23464.

The details of one or more embodiments of the present disclosure are set forth in the accompanying drawings and the description below. Other features, objects, and advantages of the invention will be apparent from the description and drawings, and from the claims.

Unless otherwise defined, all technical and scientific terms used herein have the same meaning as commonly understood by one of ordinary skill in the art to which this disclosure pertains. In case of conflict, the present document, including definitions, will control.

All publications, patent applications, patents, and other references mentioned herein are each incorporated by reference in their entirety. The materials, methods, and examples disclosed herein are illustrative only and not intended to be limiting.

DESCRIPTION OF DRAWINGS

FIGS. 7-9 depict bar graphs quantifying the % engraftment (% of human CD45+ cells/total live lymphoid cells) (upper left graph), frequency (%) of CD4+ cells (upper right graph), frequency (%) CD8+ cells (lower left graph), and frequency of human Treg cells (% FoxP3+ out of total CD25+CD127−CD4+ cells) (lower right graph) in the spleens (FIGS. 7A-7D), mLN (FIGS. 8A-8D), and small intestine (FIGS. 9A-9D) of NSG-hu mice 5 days after treatment with human (h) TL1A-Ig fusion protein (100 μg, intraperitoneally (i.p.)) or IgG control (i.p.). In each graph, the light gray bars quantify the percentages of Ki67-cells and the dark gray bars quantify the percentage of Ki67+ cells. Data illustrate the mean±S.E.M. with a total of 8 mice per group from 3 independent experiments.

FIGS. 13A and 13B are bar graphs quantifying the serum concentration of IFN-γ (ng/ml) (FIG. 13A) and TGFIβ (ng/ml) (FIG. 13B) in individual rhesus macaques on Day 0, and on Days 2 and 4 following treatment with the indicated concentration of rhesus macaque (rm) TL1A-Ig fusion protein or human (h) TL1A-Ig fusion protein. Data illustrate the mean±S.E.M. with 2 animals receiving 0.5 mg/kg rmTL1A-Ig, 4 animals receiving 1.5 mg/kg rmTL1A-Ig and 2 animals receiving 1.5 mg/kg hTL1A-Ig.

DETAILED DESCRIPTION

Figure 1:
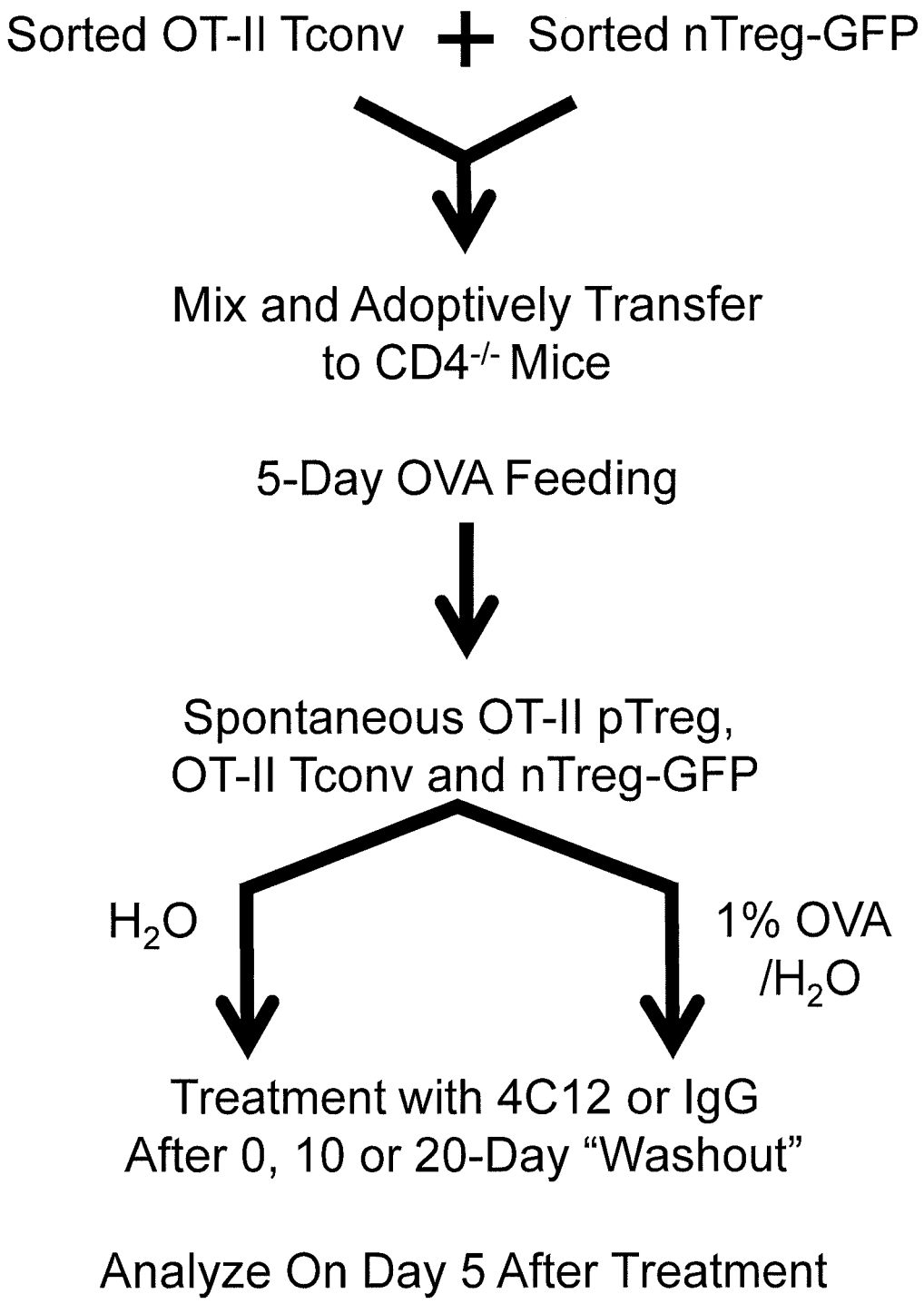
FIG. 1 is a schematic outline of the murine adoptive transfer model.

In some embodiments, the present disclosure provides an isolated or recombinant nucleic acid comprising a polynucleotide sequence which encodes a fusion protein. The fusion protein can comprise (a) a first polypeptide comprising a polypeptide sequence that specifically binds to Tumor Necrosis Factor Receptor Superfamily, Member 25 (TNFRSF25), and (b) a second polypeptide comprising an immunoglobulin (Ig) polypeptide; or a complementary polynucleotide sequence thereof.

In some embodiments, disclosed herein are fusion proteins and nucleic acid encoding the fusion proteins, wherein the fusion proteins comprise a functionally active fragment of the human or rhesus macaque TL1A polypeptide. The functionally active fragment can be, for example, the extracellular domain of TL1A (e.g., human or rhesus macaque TL 1 A) or any fragment thereof that retains specific binding to the TL 1 A receptor, TNFRSF25. In some embodiments, the functionally active fragment of TL1A includes amino acids 68-252 from the human TL1A extracellular domain. The fusion proteins can also contain one or more Ig molecules, such as one or more domains of the Ig constant regions, e.g., hinge region, CH2 domain, and/or CH3 domain.

It is presently discovered that the fusion proteins disclosed herein safely and selectively stimulate the proliferation of cognate T regulatory cells (Treg) in vivo. Based on epidemiologic data linking TL1A polymorphism to inflammatory bowel disease (IBD) in humans (see, e.g., International Patent Publication No. WO 2006/127900), and on murine studies demonstrating that transgenic overexpression of TL1A predisposes to IBD susceptibility, it was uncertain whether the fusion proteins could be safely and effectively administered in vivo. Further, it was entirely unpredictable whether therapeutically effective doses of the TL1A fusion proteins could be safely administered, in part because certain TNFRSF25 agonists have been known to cause harmful side effects in vivo. For example, prior mouse models examining transgenic expression of TL1A in mouse models of inflammatory bowel disease, asthma and arthritis, as described, e.g., by Meylan et al. Immunity. 2008 Jul. 18; 29(1):79-89; Meylan et al. Mucosal Immunol. 2011 March; 4(2):172-85; Migone et al. Immunity. 2002 March; 16(3):479-92; Fang et al. J Exp Med. 2008 May 12; 205(5):1037-48; and Bull et al. J Exp Med. 2008 Oct. 27; 205(11):2457-64. These reports demonstrated that the presence of TL1A, and signaling through TNFRSF25, resulted in enhanced stimulation of effector T cells and increased severity of immunopathology observed in the disease setting being investigated. Further, it was demonstrated that signaling through TNFRSF25 in the context of vaccination led to increased proliferation of effector T cells despite a concurrent expansion of Treg cells (see Schreiber et al. J. Immunol. 2012 Oct. 1; 189(7):3311-8). These studies demonstrated that the specificity of TNFRSF25 stimulation was governed by the availability of cognate antigen, and raised serious safety concerns regarding the specificity of these agents in primates. The reason for this concern arose from the knowledge that prior studies were performed in laboratory mice that were housed in pathogen-free settings and thus did not have a history of exposure to a diverse array of environmental antigens. Because the environmental setting is very different in humans and non-human primates (i.e., not pathogen-free), there was significant concern that exposure of human or non-human primate cells to TNFRSF25 agonists (e.g., TL1A-derived agonists) would lead to stimulation of effector T cells and enhanced immunopathology, despite enhancing effects on Treg cells. In particular, based on laboratory data in mice, enhanced inflammation in the lungs and intestinal system was predicted due to the high prevalence of 'foreign' antigens (endogenous bacteria) and environmental or food antigens.

Unexpectedly, however, it is presently demonstrated, in studies in humanized mice and primates, that treatment with the TL1A fusion proteins described herein was not only effective for inducing Treg cell proliferation, but also did not induce weight loss, cause changes in white blood cell count, or lead to any other dangerous or unwanted side effects, surprisingly indicating that the TL1A fusion proteins could be safely administered in vivo, including to primates (indicating that the TL1A fusion proteins are expected to be safely administered to humans). Thus, in addition to the fusion proteins themselves, also described herein are methods for reducing an adverse event associated with a therapy that includes the administration of a TNFRSF25 agonist, wherein the methods include administering a composition containing a TL1A fusion protein described herein. These methods reduce adverse events associated with TNFRSF25 agonist therapy, while at the same are effective for modulating an antigen-specific immune response and for treating a disease or disorder associated with an antigen-specific immune response, as discussed below.

Furthermore, while not intending to be bound by any particular theory or mechanism of action, the present examples also demonstrate that the effect of the TL1A fusion proteins was antigen-specific, both systemically and in the mucosa, indicating that the fusion proteins could be used to modulate both systemic and mucosal antigen-specific immune response. Thus, also described herein are methods of using the fusion proteins for modulating an antigen-specific immune response (e.g., in a human patient in need thereof). Also described are methods of treating a disease or disorder associated with an antigen-specific immune response (e.g., autoimmune disease or disorder (e.g. inflammatory bowel disease (IBD) and rheumatoid arthritis), transplant rejection, graft-versus-host disease (GVHD), inflammation, asthma, allergies, and chronic infection), and/or treating one or more symptoms of the disease or disorder (e.g., in a human patient in need thereof). The fusion proteins and method of their use are described in detail below.

It is also presently discovered that combination therapies that comprise administering to a subject (1) a TNFRSF25 agonist, (a TL1A fusion protein disclosed herein, or the agonistic anti-TNFRSF25 antibody 4C 12), and (2) a low dose or very low dose of interleukin (IL)-2, had a surprising and unexpected synergistic effect on the expansion of FoxP3+ T regulatory cells. While not intending to be bound by theory or limited to a particular mechanism of action, the expansion of Treg cells is thought to have beneficial effects in diseases and disorders associated with undesirable antigen-specific immune responses, e.g., autoimmune disease or disorder (e.g., IBD) and rheumatoid arthritis), transplant rejection, GVHD, inflammation, asthma, allergies, and chronic infection. Thus, also provided herein are methods of treating the above diseases and disorders and others, using the above-described combination therapies.

It is also presently discovered that administering the mTOR inhibitor rapamycin in combination with the agonistic anti-TNFRSF25 antibody 4C12 to a subject resulted in a specific reduction of effector T cells, but had no effect on the expansion of Treg cells induced by the agonistic anti-TNFRSF25 antibody. This discovery was surprising, since it was previously thought that rapamycin would have a global inhibitory effect on both effector T cells and Treg cells. Based at least in part on this discovery, also provided herein is a combination therapy comprising administering to a subject in need thereof a TNFRSF25 agonist and the administration of an mTOR inhibitor, e.g., to inhibit unwanted activation and expansion of CD4+ and/or CD8+ T effector cells.

Definitions:

As used herein, the term "isolated" means that the referenced material is removed from the environment in which it is normally found. Thus, an isolated biological material can be free of cellular components, i.e., components of the cells in which the material is found or produced. Isolated nucleic acid molecules include, for example, and without limitation, a PCR product, an isolated mRNA, a cDNA, or a restriction fragment. Isolated nucleic acid molecules also include, for example, sequences inserted into vectors, plasmids, cosmids, artificial chromosomes, and the like. An isolated nucleic acid molecule is preferably excised from the genome in which it may be found, and more preferably is no longer joined to non-regulatory sequences, non-coding sequences, or to other genes located upstream or downstream of the nucleic acid molecule when found within the genome. An isolated nucleic acid has 3' and 5' ends that are different than the 3' and 5' ends of the nucleic acid when in its natural environment (i.e., in the nucleus of a cell). An isolated protein may be associated with other proteins or nucleic acids, or both, with which it associates in the cell, or with cellular membranes if it is a membrane-associated protein. An isolated fusion protein may be associated with cellular components of the cell used to produce the fusion protein in vitro.

As used herein, the term "nucleic acid encoding" or "polynucleotide encoding" a TL1A fusion protein encompasses a nucleic acid which includes only coding sequence for a TL1A fusion protein as well as a nucleic acid which includes additional coding and/or non-coding sequence(s).

The terms "percent (%) sequence identity," and the like, generally refer to the degree of identity or correspondence between different nucleotide sequences of nucleic acid molecules or amino acid sequences of proteins that may or may not share a common evolutionary origin. Sequence identity can be determined using any of a number of publicly available sequence comparison algorithms, such as BLAST, FASTA, DNA Strider, GCG (Genetics Computer Group, Program Manual for the GCG Package, Version 7, Madison, Wis.), etc. To determine the percent identity between two amino acid sequences or two nucleic acid molecules, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are, or are about, of the same length. The percent identity between two sequences can be determined using techniques similar to those described below, with or without allowing gaps. In calculating percent sequence identity, typically exact matches are counted. The determination of percent identity between two sequences can be accomplished using a mathematical algorithm. A non-limiting example of a mathematical algorithm utilized for the comparison of two sequences is the algorithm of Karlin and Altschul, Proc. Natl. Acad. Sci. USA 1990, 87:2264, modified as in Karlin and Altschul, Proc. Natl. Acad. Sci. USA 1993, 90:5873-5877. Such an algorithm is incorporated into the NBLAST and XBLAST programs of Altschul et al., J. Mol. Biol. 1990; 215: 403. BLAST nucleotide searches can be performed with the NBLAST program, score=100, wordlength=12, to obtain nucleotide sequences homologous to sequences disclosed herein. BLAST protein searches can be performed with the XBLAST program, score=50, wordlength=3, to obtain amino acid sequences homologous to protein sequences disclosed herein. To obtain gapped alignments for comparison purposes, Gapped BLAST can be utilized as described in Altschul et al., Nucleic Acids Res. 1997, 25:3389. Alternatively, PSI-Blast can be used to perform an iterated search that detects distant relationship between molecules. See Altschul et al. (1997) supra. When utilizing BLAST, Gapped BLAST, and PSI-Blast programs, the default parameters of the respective programs (e.g., XBLAST and NBLAST) can be used. See ncbi.nlm.nih.gov/BLAST/on the World-WideWeb. Another non-limiting example of a mathematical algorithm utilized for the comparison of sequences is the algorithm of Myers and Miller, CABIOS1988; 4: 11-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used. The percent identity between two amino acid sequences can be determined using the algorithm of Needleman and Wunsch (J. Mol. Biol. 1970, 48:444-453), which has been incorporated into the GAP program in the GCG software package (Accelrys, Burlington, Mass.; available at accelrys.com on the WorldWideWeb), using either a Blossum 62 matrix or a PAM250 matrix, a gap weight of 16, 14, 12, 10, 8, 6, or 4, and a length weight of 1, 2, 3, 4, 5, or 6. In yet another preferred embodiment, the percent identity between two nucleotide sequences is determined using the GAP program in the GCG software package using a NWSgapdna.CMP matrix, a gap weight of 40, 50, 60, 70, or 80, and a length weight of 1, 2, 3, 4, 5, or 6. A particularly preferred set of parameters (and the one that can be used if the practitioner is uncertain about what parameters should be applied to determine if a molecule has a certain sequence identity is using a Blossum 62 scoring matrix with a gap open penalty of 12, a gap extend penalty of 4, and a frameshift gap penalty of 5.

The term "substantially identical," at the amino acid sequence level, means that the sequence identity of two amino acid sequences has at least about 70% or greater (e.g., 75%, 80%, 85%, 90%, 91%, 92%, 93%, 94%, 95%, 96%, 97%, 98% or 99%) sequence identity.

As used herein, the TL1A polypeptide that is "capable of specifically binding to Tumor Necrosis Factor Receptor Superfamily, Member 25 (TNFRSF25)" is one which interacts with TNFRSF25 such that at least one function mediated by the natural ligand TL1A is mediated. This function can be, for example, induction and/or enhancement of regulatory T cell proliferation. Moreover, the TL1A polypeptides and fusion proteins described herein are said to be "specifically binding" if: 1) they exhibit a threshold level of binding activity, and/or 2) they do not significantly cross-react with known related receptors. The specificity of binding to TNFRSF25 is routinely confirmed using the caspase-release assay as demonstrated in FIG. 6. The control groups for these studies include cells not transfected with TNFRSF25, which demonstrate no susceptibility to death following treatment with TNFRSF25 agonists including TL1A-Ig. The potency and $EC_{50}$ of the agonists is also approximated with this assay, and routinely demonstrated to be in the ng-μg range as demonstrated in FIG. 6.

The meaning of the phrase "antigen-specific immune response" is known in the art. By way of example, an immune response that is specific for antigen "X" will have activated B and/or T cells that recognize one or more epitopes present in antigen "X."

As used herein, the phrase "modulating an antigen-specific immune response" means that the immune response against the antigen, as measured by any suitable measure (e.g., frequency of antigen-specific antibodies, T cells, B cells, antigen-specific T cell proliferation, etc.) is increased or decreased by at least 5%, at least 10%, at least 15%, 25%, 50%, 70%, 75%, 80%, 90%, 95%, 99%, or 100%.

As used herein, "TNFRSF25 agonist" means a substance that binds to the TNFRSF25 receptor and triggers a response in the cell on which the TNFRSF25 receptor is expressed similar to a response that would be observed by exposing the cell to a natural TNFRSF25 ligand, e.g., TL1A.

As used herein, "suboptimal" in the context of the expansion of Treg cells induced by an interleukin (e.g., IL-2 or an analog thereof) in a combination therapy with another agent (e.g., a TNFRSF25 agonist, e.g., a TL1A fusion protein, an agonistic anti-TNFRSF25 antibody, or small molecule agonist of TNFRSF25) means less than 100% compared to the amount or degree of Treg cell expansion induced in the presence of that same interleukin or analog thereof alone (i.e., not in a combination therapy).As used herein, the term "antibody" is inclusive of all species, including human and humanized antibodies and the antigenic target, for example, TNFRSF25, can be from any species. Thus, an antibody, for example, anti-TNFRSF25 can be mouse anti-human TNFR25, goat anti-human TNFR25; goat anti-mouse TNFR25; rat anti-human TNFR25; mouse anti-rat TNFR25 and the like. The combinations of antibody generated in a certain species against an antigen target, e.g. TNFRSF25, from another species, or in some instances the same species (for example, in autoimmune or inflammatory response) are limitless and all species are embodied in the present disclosure. The term antibody is used in the broadest sense and includes fully assembled antibodies, monoclonal antibodies (including human, humanized or chimeric antibodies), polyclonal antibodies, multispecific antibodies (e.g., bispecific antibodies), and antibody fragments that can bind antigen (e.g., Fab', $F(ab)_2$, Fv, single chain antibodies, diabodies), comprising complementarity determining regions (CDRs) of the foregoing as long as they exhibit the desired biological activity.

Depending on the amino acid sequence of the constant domain of their heavy chains, human immunoglobulins can be assigned to different classes. There are five major classes, IgA, IgD, IgE, IgG and IgM, and several of these may be further divided into subclasses or isotypes, e.g., IgG1, IgG2, IgG3, IgG4, IgA1 and IgA2. The heavy-chain constant domains that correspond to the different classes of immunoglobulins are called alpha, delta, epsilon, gamma and mu respectively. The subunit structures and three-dimensional configurations of different classes of immunoglobulins are well known. Different isotypes have different effector functions; for example, IgG1 and IgG3 isotypes have ADCC activity. The invention contemplates that antibodies of any class or subclass may be prepared, including IgA, IgD, IgE, IgG and IgM, although IgG is preferred.

An "immunogenic polypeptide" or "antigen" is a polypeptide derived from the cell or organism that elicits in a subject an antibody-mediated immune response (i.e., a "B cell" response or humoral immunity), a cell-mediated immune response (i.e. a "T cell" response), or a combination thereof. A cell-mediated response can involve the mobilization helper T cells, cytotoxic T-lymphocytes (CTLs), or both. Preferably, an immunogenic polypeptide elicits one or more of an antibody-mediated response, a CD4+ Th1-mediated response (Th1: type 1 helper T cell), and a CD8+T cell response. It should be understood that the term "polypeptide" as used herein refers to a polymer of amino acids and does not refer to a specific length of a polymer of amino acids. Thus, for example, the terms peptide, oligopeptide, and protein are included within the definition of polypeptide.

As used herein, "treating" or "treatment" of a state, disease, disorder or condition includes: (1) preventing or delaying the appearance of clinical or sub-clinical symptoms of the state, disease, disorder or condition developing in a mammal that may be afflicted with or predisposed to the state, disease, disorder or condition but does not yet experience or display clinical or subclinical symptoms of the state, disease, disorder or condition; or (2) inhibiting the state, disease, disorder or condition, i.e., arresting, reducing or delaying the development of the state, disease, disorder or condition, or a relapse thereof (in case of maintenance treatment) or at least one clinical or sub-clinical symptom thereof; or (3) relieving the state, disease, disorder or condition, i.e., causing regression of the state, disease, disorder or condition or at least one of its clinical or sub-clinical symptoms. The benefit (e.g., alleviation of at least one symptom of the state, disease, disorder or condition) to a subject to be treated is either statistically significant or at least perceptible to the patient or to the physician. The alleviation (e.g., of at least one symptom of the state, disease, disorder or condition) is typically at least about 10%, 20%, 30%, 40%, 50%, 60%, 70%, 80%, 90% or greater (compared to before treatment).

As used herein, "preventing" a state, disease, disorder or condition (e.g., a state, disease, disorder or condition associated with an antigen-specific immune response, e.g., an autoimmune disease or disorder, transplant rejection, graft-versus-host disease, inflammation, asthma, allergies, and chronic infection) in a subject means for example, to stop the development of one or more symptoms of the state, disease, disorder or condition, in a subject before they occur or are detectable, e.g., by the patient or the patient's doctor. Preferably, the state, disease, disorder or condition does not develop at all, i.e., no symptom of the state, disease, disorder or condition is detectable. However, it can also result in delaying or slowing of the development of one or more symptoms of the state, disease, disorder or condition. Alternatively, or in addition, it can result in the decreasing of the severity of one or more subsequently developed symptoms.

As used herein "combination therapy" means the treatment of a subject (e.g., a subject in need of treatment, e.g., a human patient) with a TNFRSF25 agonist described herein (e.g., TL1A fusion protein, agonistic anti-TNFRSF25 antibody, small molecule, etc.) and one or more other therapies (e.g., drug or therapeutic treatment) for, e.g., modifying an antigen-specific immune response and/or treating a disease or disorder (e.g., treating one or more symptoms of the disease or disorder). Such combination therapy can be sequential therapy wherein the patient is treated first with one therapy and then the other, and so on, or all therapies can be administered simultaneously. In either case, these therapies are said to be "coadministered." It is to be understood that "coadministered" does not necessarily mean that the drugs and/or therapies are administered in a combined form (i.e., they may be administered separately or together to the same or different sites at the same or different times).

The term "pharmaceutically acceptable carrier" means a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The term "pharmaceutically acceptable derivative" as used herein means any pharmaceutically acceptable salt, solvate or prodrug, e.g., ester, of a compound disclosed herein, which upon administration to the recipient is capable of providing (directly or indirectly) a compound disclosed herein, or an active metabolite or residue thereof. Such derivatives are recognizable to those skilled in the art, without undue experimentation. Nevertheless, reference is made to the teaching of Burger's Medicinal Chemistry and Drug Discovery, 5th Edition, Vol 1: Principles and Practice, which is incorporated herein by reference to the extent of teaching such derivatives. Preferred pharmaceutically acceptable derivatives are salts, solvates, esters, carbamates, and phosphate esters. Particularly preferred pharmaceutically acceptable derivatives are salts, solvates, and esters. Most preferred pharmaceutically acceptable derivatives are salts and esters.

The term "nucleic acid hybridization" refers to the pairing of complementary strands of nucleic acids. The mechanism of pairing involves hydrogen bonding, which may be Watson-Crick, Hoogsteen or reversed Hoogsteen hydrogen bonding, between complementary nucleoside or nucleotide bases (nucleobases) of the strands of nucleic acids. For example, adenine and thymine are complementary nucleobases that pair through the formation of hydrogen bonds. Hybridization can occur under varying circumstances. Nucleic acid molecules are "hybridizable" to each other when at least one strand of one nucleic acid molecule can form hydrogen bonds with the complementary bases of another nucleic acid molecule under defined stringency conditions. Stringency of hybridization is determined, e.g., by (i) the temperature at which hybridization and/or washing is performed, and (ii) the ionic strength and (iii) concentration of denaturants such as formamide of the hybridization and washing solutions, as well as other parameters. Hybridization requires that the two strands contain substantially complementary sequences. Depending on the stringency of hybridization, however, some degree of mismatches may be tolerated. Under "low stringency" conditions, a greater percentage of mismatches are tolerable (i.e., will not prevent formation of an anti-parallel hybrid). See Molecular Biology of the Cell, Alberts et al., 3rd ed., New York and London: Garland Publ., 1994, Ch. 7.

Typically, hybridization of two strands at high stringency requires that the sequences exhibit a high degree of complementarity over an extended portion of their length. Examples of high stringency conditions include: hybridization to filter-bound DNA in 0.5 M NaHPO4, 7% SDS, 1 mM EDTA at 65° C., followed by washing in 0.1×SSC/0.1% SDS (where 1×SSC is 0.15 M NaCl, 0.15 M Na citrate) at 68° C. or for oligonucleotide (oligo) inhibitors washing in 6×SSC/0.5% sodium pyrophosphate at about 37° C. (for 14 nucleotide-long oligos), at about 48° C. (for about 17 nucleotide-long oligos), at about 55° C. (for 20 nucleotide-long oligos), and at about 60° C. (for 23 nucleotide-long oligos).

Conditions of intermediate or moderate stringency (such as, for example, an aqueous solution of 2×SSC at 65° C.; alternatively, for example, hybridization to filter-bound DNA in 0.5 M NaHPO4, 7% SDS, 1 mM EDTA at 65° C. followed by washing in 0.2×SSC/0.1% SDS at 42° C.) and low stringency (such as, for example, an aqueous solution of 2×SSC at 55° C.), require correspondingly less overall complementarity for hybridization to occur between two sequences. Specific temperature and salt conditions for any given stringency hybridization reaction depend on the concentration of the target DNA or RNA molecule and length and base composition of the probe, and are normally determined empirically in preliminary experiments, which are routine (see Southern, J. Mol. Biol. 1975; 98:503; Sambrook et al., Molecular Cloning: A Laboratory Manual, 2nd ed., vol. 2, ch. 9.50, CSH Laboratory Press, 1989; Ausubel et al. (eds.), 1989, Current Protocols in Molecular Biology, Vol. I, Green Publishing Associates, Inc., and John Wiley & Sons, Inc., New York, at p. 2.10.3). An extensive guide to the hybridization of nucleic acids is found in, e.g., Tijssen (1993) Laboratory Techniques in Biochemistry and Molecular Biology—Hybridization with Nucleic Acid Probes part I, chapt 2, "Overview of principles of hybridization and the strategy of nucleic acid probe assays," Elsevier, N.Y. ("Tijssen").

As used herein, the term "standard hybridization conditions" refers to hybridization conditions that allow hybridization of two nucleotide molecules having at least 50% sequence identity. According to a specific embodiment, hybridization conditions of higher stringency may be used to allow hybridization of only sequences having at least 75% sequence identity, at least 80% sequence identity, at least 90%, 91%, 92%, 93%, 94%, 95%, 96%, 97%, 98%, or 99% sequence identity.

The definitions of protein, peptide and polypeptide are well-known in the art. The term "protein", as used herein, is synonymous with the term "peptide" or "polypeptide," and is understood to mean a chain of amino acids arranged linearly and joined together by peptide bonds between the carboxyl and amino groups of adjacent amino acid residues. Thus, the term polypeptide can refer to a full length amino acid sequence of a protein, or to a fragment thereof.

As used herein, the terms "nucleic acid," "oligonucleotide," "polynucleotide" and "polynucleotide sequence" are used interchangeably, and refer to a deoxyribonucleotide or ribonucleotide in either single- or double-stranded form. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene (methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press). PNAs contain non-ionic backbones, such as N-(2-aminoethyl) glycine units. Phosphorothioate linkages are described in WO 97/03211; WO 96/39154; Mata (1997) Toxicol. Appl. Pharmacol. 144:189-197. Other synthetic backbones encompassed by the term include methyl-phosphonate linkages or alternating methylphosphonate and phosphodiester linkages (Strauss-Soukup (1997) Biochemistry 36:8692-8698), and benzylphosphonate linkages (Samstag (1996) Antisense Nucleic Acid Drug Dev 6:153-156). The term nucleic acid is used interchangeably with cDNA, cRNA, mRNA, oligonucleotide, polynucleotide and amplification product.

As used herein, "operably linked" with a polynucleotide sequence means that a target polynucleotide sequence and one or more expression control sequences (e.g., promoters) are physically linked so as to permit expression of the polypeptide encoded by the target polynucleotide sequence within a host cell.

As used herein, the term "about" or "approximately" usually means within an acceptable error range for the type of value and method of measurement. For example, it can mean within 20%, more preferably within 10%, and most preferably still within 5% of a given value or range. Alternatively, especially in biological systems, the term "about" means within about a log (i.e., an order of magnitude) preferably within a factor of two of a given value.

TNFRSF25 Agonists

The present disclosure provides methods that include the administration, either alone, or as part of a combination therapy, of an agonist of TNFRSF25 (also known as DR3). The present disclosure provides novel TNFRSF25 agonists, such as the TL1A fusion proteins described herein. However, also provided herein are novel methods that include the use of other TNFRSF25 agonists which are known in the art. For example, non-limiting examples of TNFRSF25 agonists that may be used in the combination therapies disclosed herein (which include the co-administration of an mTOR inhibitor, e.g., rapamycin, and/or IL-2 with a TNFRSF25 agonist) include, e.g., small molecules, antibodies, and fusion proteins. Non-limiting examples of such TNFRSF25 agonists are described, e.g., in U.S. pre-grant publication Nos. 2011/0243951, 2012/0029472, and 2012/0135011, all by Podack et al. Methods for preparing anti-TNFRSF25 antibodies are described in US 2012/0029472 by Podack et al. The present methods, e.g., the combination therapies disclosed herein, envision the use of any suitable TNFRSF25 agonist known in the art. In some embodiments, TNFRSF25 agonists are ones which enhance the expansion of Treg cells.

In some embodiments, a TNFRSF25 agonist is a small molecule. Chemical agents, referred to in the art as "small molecules" are typically organic, non-peptide molecules, having a molecular weight less than 10,000 Da, preferably less than 5,000 Da, more preferably less than 1,000 Da, and most preferably less than 500 Da. This class of modulators includes chemically synthesized molecules, for instance, compounds from combinatorial chemical libraries. Synthetic compounds may be rationally designed or identified by screening compound libraries for TNFRSF25-modulating activity according to methods known in the art. Alternative appropriate modulators of this class are natural products, particularly secondary metabolites from organisms such as plants or fungi, which can also be identified by screening compound libraries for TNFRSF25-modulating activity. Methods for generating and obtaining small molecules are well known in the art (see, e.g., Schreiber, Science 2000; 151:1964-1969; Radmann et al., Science 2000; 151: 1947-1948).

In some embodiments, the present disclosure provides nucleic acids encoding TL1A fusion proteins and compositions that contain the TL1A fusion proteins. Also described herein are methods of producing TL1A fusion proteins. The method can include for example, introducing into a population of cells a nucleic acid encoding the TL1A fusion protein, e.g., a nucleic acid described herein (e.g., SEQ ID NO: 15), wherein the nucleic acid is operatively linked to a regulatory sequence effective to produce the fusion protein polypeptide encoded by the nucleic acid; and culturing the cells in a culture medium to produce the polypeptide. In some embodiments, the method can further include isolating the fusion protein polypeptide from the cells or culture medium. The nucleic acid can also further contain a third nucleotide sequence that encodes a secretory or signal peptide operably linked to the fusion protein. In some embodiments, the fusion protein is secreted from the host cell as a fusion protein homomultimer (e.g., as a dimer of trimers). In some embodiments, the fusion protein homomultimer is recovered from the culture medium, the host cell or host cell periplasm. Further, the fusion protein homomultimer can contain one or more covalent disulfide bonds between a cysteine residue of the first fusion protein and at least one cysteine residue of one or more additional fusion proteins.

TL1A is a type II transmembrane protein belonging to the TNF superfamily and has been designated TNF superfamily member 15 (TNFSF15). TL1A is the natural ligand for TNFRSF25. See U.S. Pat. No. 6,713,061, and Borysenko, et al., Biochem Biophys Res Commun. 2005 Mar. 18; 328(3): 794-9, Sheikh, et al., Curr. Cancer Drug Targets. 2004 February; 4(1):97-104, and U.S. publication number 2007/0128184. Human TL1A nucleic acid and amino acid sequences are known and have been described. See, for example GenBank® Accession No. CCDS6809.1 (nucleic acid sequence) (SEQ ID NO: 1); and GenBank® Accession No. EAW87431 (amino acid sequence) (SEQ ID NO: 2). Other nucleic acid and amino acid sequences for human TL1A have been described, including, but not limited to GenBank® Accession Nos. NM_001204344.1/NP_001191273.1, NM_005118.3/NP_005109.2, NM_001039664.1/NP 001034753.1, NM_148970.1/NP_683871.1, NM 148967.1/NP_683868.1, NM_148966.1/NP_683867.1, NM_148965.1/NP_683866.1, and NM_003790.2/NP_003781.1, each of which is incorporated by reference (including the referenced sequences).

Rhesus macaque TL1A nucleic acid and amino acid sequences can be inferred from the Macaca mulatta chromosome 15, Mmul_051212, whole genome shotgun sequence (GenBank® Accession No. NC_007872.1). The mRNA sequence having GenBank® Accession No. NM_001194132.1 (SEQ ID NO: 3). An exemplary rhesus macaque amino acid sequence has GenBank® Accession No. NP_001181061, which is incorporated by reference (including the referenced sequence). (SEQ ID NO: 4).

Encompassed herein are non-naturally occurring polynucleotides encoding fusion proteins that specifically bind to TNFRSF25. For example, provided herein are isolated or recombinant nucleic acids containing a polynucleotide sequence which encodes a fusion protein, the fusion protein containing (a) a first polypeptide containing a polypeptide sequence that specifically binds to TNFRSF25, and (b) a second polypeptide containing an Ig polypeptide; or a complementary polynucleotide sequence thereof. A fusion protein described herein can also contain a TL1A polypeptide linked to another second polypeptide that promotes multimerization, e.g., to for a dimer, a trimer, a dimer of trimers, etc. For example, the second polypeptide can be a surfactant protein.

In general, the fusion proteins are agonists of TNFRSF25. In some embodiments, the fusion protein comprises a TL1A polypeptide (a "TL1A fusion protein"). Typically, a TL1A fusion protein encompassed herein induces a signaling response that is similar to the response induced by the natural ligand, TL1A. For example, in some embodiments, TL1A fusion proteins encompassed herein induce proliferation of Treg cells in vitro and/or in vivo. In some embodiments, the TL1A fusion proteins encompassed herein have a T effector cells costimulation effect. Suitable assays for measuring T cell proliferation in vitro and in vivo are known in the art and described in Example 1 (materials and methods). The activity of the TL1A fusion proteins can be measured as described in detail in Khan et al. J. Immunol. 2013 Feb. 15; 190(4):1540-50. In some embodiments, the TL1A fusion protein comprises: a first polypeptide that is capable of binding to TNFRSF25; and at least a second polypeptide. In some embodiments the polypeptide comprises or consists of the extracellular domain of TL1A (e.g., human TL1A extracellular domain) or a fragment thereof that is capable of binding to TNFRSF25 (i.e., a "functionally active fragment"). In some embodiments, the polypeptide is a variant or ortholog of human TL1A or a functionally active fragment thereof. In some embodiments, the human TL1A polypeptide comprises or consists of amino acid residues 68-252 from the TL1A extracellular domain.

In some embodiments, the second polypeptide can be an Ig molecule. For example the immunoglobulin molecule can be the constant region of an antibody (e.g., IgG, IgA, IgM or IgD). The Ig heavy chains can be divided into three functional regions: Fd (containing $V_H$ and CH1 domains), hinge, and Fc. Fd in combination with the light chain forms the "Fab" portion of an antibody. The hinge region is found in IgG, IgA, and IgD classes, and acts as a flexible spacer, allowing the Fab portion to move freely in space. The hinge domains are structurally diverse, varying in both sequence and length among immunoglobulin classes and subclasses. Three human IgG subclasses, IgG1, IgG2, and IgG4, have hinge regions of 12-15 amino acids while IgG3 has approximately 62 amino acids, including 21 proline residues and 11 cysteine residues. The structure of the hinge region is described in detail in Shin et al., Immunological Reviews 130:87 (1992) and in U.S. Patent Application Publication No. 2013/0142793.

For an immunoglobulin fusion protein which is intended for use in humans, the constant regions may be of human sequence origin in order to minimize a potential anti-human immune response. The constant region may also be of human sequence origin in order to provide appropriate effector functions. In some embodiments, the constant region may facilitate multimerization of the fusion protein. Manipulation of sequences encoding antibody constant regions is described in the PCT publication of Morrison and Oi, WO 89/007142. For example, the CH1 domain can be deleted and the carboxyl end of the binding domain is joined to the amino terminus of CH2 through the hinge region. In some embodiments, the Ig molecule comprises a CH2 domain and/or a CH3 domain and/or a hinge region of an immunoglobulin. In some embodiments the second polypeptide is an Ig molecule comprising a hinge region, a CH2 domain and a CH3 domain of an IgG molecule (e.g., human IgG). In some embodiments, the second polypeptide is an Ig molecule comprising a CH2 domain and a CH3 domain of an IgG molecule (e.g., human IgG). In some embodiments, the second polypeptide is an Ig molecule comprising a hinge region and one or more of: a CH2 domain and a CH3 domain of an IgG molecule (e.g., human IgG). In some embodiments, the second polypeptide is an Ig molecule comprising a CH2 domain and at least one of: a hinge region and a CH3 domain of an IgG molecule (e.g., human IgG). In some embodiments, the human immunoglobulin hinge region is an IgG1 hinge region comprising 0, 1, 2, 3, or more cysteine residues.

Fusion proteins encompassed herein can also contain other polypeptides instead of or in addition to the Ig molecules described above. For example, a fusion protein can contain a polypeptide that binds to TNFRSF25 and a surfactant protein, or other polypeptide that facilitates multimerization of the fusion protein.

The nucleic acids disclosed herein, also referred to herein as polynucleotides, may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The sense and anti-sense strands are "complementary" to each other. The nucleic acids which encode TL1A fusion proteins for use according to the compositions and methods disclosed herein may include, but are not limited to: only the coding sequence for the TL1A fusion protein; the coding sequence for the TL1A fusion protein and additional coding sequence; the coding sequence for the TL1A fusion protein (and optionally additional coding sequence) and non-coding sequence, such as introns or non-coding sequences 5' and/or 3' of the coding sequence for the TL1A fusion polypeptide, which for example may further include but need not be limited to one or more regulatory nucleic acid sequences that may be a regulated or regulatable promoter, enhancer, other transcription regulatory sequence, repressor binding sequence, translation regulatory sequence or any other regulatory nucleic acid sequence. Thus, as defined above, the term "nucleic acid encoding" or "polynucleotide encoding" a TL1A fusion protein encompasses a nucleic acid which includes only coding sequence for a TL1A fusion polypeptide as well as a nucleic acid which includes additional coding and/or non-coding sequence(s).

Exemplary fusion proteins and the nucleic acid molecules encoding the fusion proteins are described below. It is to be understood that the sequences described below are not limiting. As discussed in more detail below, other TL1A fusion proteins (e.g. those containing fragments, variants, and orthologs of TL1A are also encompassed by the present disclosure, as well as various second polypeptides and/or other functional domains. For example, also encompassed herein are fusion proteins that comprise TL1A and a surfactant protein. In some embodiments, the human TL1A polypeptide comprises or consists of amino acid residues 68-252 from the TL1A extracellular domain.

By way of non-limiting example, in some embodiments the nucleic acid and amino acid sequences of the TL1A portion of the rhesus macaque TL1A fusion protein are:

(SEQ ID NO: 5)

aaaggacaggagtttgcaccttcacatcagcaagtttatgcacctcttag agcagacggagataagccaagggcacacctgacagttgtgacacaaactc ccacacagcactttaaaaatcagttcccagctctgcactgggaacatgaa ctaggcctggccttcaccaagaaccgaatgaactataccaacaaattcct gctgatcccagagtcgggagactacttcatttactcccaggtcacattcc gtgggatgacctctgagtgcagtgaaatcagacaagcaggccgaccaaac aagccagactccatcactgtggtcatcaccaaggtaacagacagctaccc tgagccaacccagctcctcatggggaccaagtctgtgtgcgaagtaggta gcaactggttccagcccatctacctcggacccatgttctccttgcaagaa ggggacaagctaatggtgaacgtcagtgacatctccttggtggattacac aaaagaagataaaaccttctttggagccttcttactatag;

and (SEQ ID NO: 6)

kgqefapshqqvyaplradgdkprahltvvtqtptqhfknqfpalhwehe lglaftknrmnytnkfllipesgdyfiysqvtfrgmtsecseirpgrpnk pdsitvvitkvtdsypeptqllmgtksvcevgsnwfqpiy1gpmfslqeg dklmvnvedislvdytkedktffgafll.

Furthermore, in some embodiments the nucleic acid of the rhesus macaque Ig sequence (IgG1 hinge-CH2-CH3 sequence) is:

ataaaaacatgtggtggtggcagcaaacctcccacgtgcccaccgtgccca gcacctgaactcctgggggac cgtcagtcttcctcttccccccaaaaccc aaggacaccctcatgatctcccggacccctgaggtcacatgcgtggtggtagacgt gagccaggaagaccccgatgtcaagttcaactggtacgtaaacggcgcggaggt gcatcatgcccagacgaagccacggga gacgcagtacaacagcacatatc gtgtggtcagcgtcctcaccgtcacgcaccaggactggct-gaacggcaaggagtacacgt gcaaggtctccaacaaagccctcccggtccc-catccagaaaaccatct ccaaagacaaagggcagccccgagagcctcagg tgtacaccct gcccccgtcccgggaggagctgac-caagaaccaggtcagcctgacctgcctgg tcaaaggcttctacccca gcga-catcgtcgtggagtgggagaacagcgggcagccggag aacacctacaagac-caccccgcccgtgctggactccg acggctcctactt cctctacagcaagctcaccgtggacaagagcaggtggcagcaggggaacgtct tctcatgctccgtgat gcatgaggctctgcacaaccactacacgcag (SEQ ID NO: 7), wherein residues 1-52 (bold text) are the hinge region, residues 53-382 are the CH2 domain, and residues 383-675 (bold, italicized text) are the CH3 domain; and the amino acid sequence of the rhesus macaque Ig sequence (IgG1 hinge-CH2-CH3 sequence) is:

iktcgggskpptcppcpapellggpsvflfppkpkdtlmisrtpevtcvvvd vsqedpdvkfnwyvngaevh haqtkpretqynstyrvvsvltvthq dwlngkeytckvsnkalpvpiqktiskdkgqprepqvytlppsreelt-knqvsltcl vkgfypsdivvewensgqentykttppvldsdgsyflysk-ltvdksr wqqgnvfscsvmhealhnhytq (SEQ ID NO: 8), wherein residues 1-17 (bold text) are the hinge region, residues 18-127 are the CH2 domain, and residues 128-225 (bold, italicized text) are the CH3 domain.

In some embodiments, the nucleic acid and amino acid sequences of the rhesus macaque TL1A-Ig fusion protein are:

(SEQ ID NO: 9)

atggagacagacacactcctgctatgggtactgctgctctgggttccagg ttccactggtgacctcgagataaaaacatgtggtggtggcagcaaacctc ccacgtgcccaccgtgcccagcacctgaactcctgggggggaccgtcagtc ttcctcttccccccaaaacccaaggacaccctcatgatctcccggacccc tgaggtcacatgcgtggtggtagacgtgagccaggaagaccccgatgtca agttcaactggtacgtaaacggcgcggaggtgcatcatgcccagacgaag ccacgggagacgcagtacaacagcacatatcgtgtggtcagcgtcctcac cgtcacgcaccaggactggctgaacggcaaggagtacacgtgcaaggtct ccaacaaagccctcccggtccccatccagaaaaccatctccaaagacaaa gggcagccccgagagcctcaggtgtacaccctgcccccgtcccgggagga gctgaccaagaaccaggtcagcctgacctgcctggtcaaaggcttctacc ccagcgacatcgtcgtggagtgggagaacagcgggcagccggagaacacc tacaagaccaccccgcccgtgctggactccgacggctcctacttcctcta cagcaagctcaccgtggacaagagcaggtggcagcaggggaacgtcttct catgctccgtgatgcatgaggctctgcacaaccactacacgcaggaattc aaaggacaggagtttgcaccttcacatcagcaagtttatgcacctcttag agcagacggagataagccaagggcacacctgacagttgtgacacaaactc ccacacagcactttaaaaatcagtteccagctctgcactgagaacatgaa ctaggcctggccttcaccaagaaccgaatgaactataccaacaaattcct gctgatcccagagtcgggagactacttcatttactcccaggtcacattcc gtgggatgacctctgagtgcagtgaaatcagacaagcaggccgaccaaac aagccagactccatcactgtggtcatcaccaaggtaacagacagctaccc tgagccaacccagctcctcatggggaccaagtctgtgtgcgaagtaggta gcaactggttccagcccatctacctcggacccatgttctccttgcaagaa ggggacaagctaatggtgaacgtcagtgacatctccttggtggattacac aaaagaagataaaaccttctttggagccttcttactatag;

and (SEQ ID NO: 10:

*metdtlllwvlllwvpgstgd*leiktcgggskpptcppcpapellggps vflfppkpkdtlmisrtpevtcyvvdvsgedpdvkfnwyvngaevhhagt kpretqynstyrvvsyltvthqdwlngkeytckvsnkalpvpiqktiskd kgqprepgvytlppereeltkngveltclvkgfypsdivvewensggpen tykttppvldsdgsyflyskltvdksrwqqgnvfscsvmhealhnhytq

*ef*kgqefapshqqvyaplradgdkprahltvvtqtptqhfknqfpalhwe helqlaftknrmnytnkfllipesgdyfiysqvtfrgmtsecseirqaqr pnkpdsitvvitkvtdsypeptqllmgtksvcevgsnwfqpiylqpmfsl qegdklmvnvsdislvdytkedktffgafll.

In the above fusion protein sequences (DNA and amino acid, SEQ ID NOs: 9 and 10), the italicized and underlined residues correspond to the mouse kappa leader sequence (residues 1-63 of SEQ ID NO: 9 and residues 1-21 of SEQ ID NO: 10); the bold and italicized text corresponds to restriction enzyme cloning sites (residues 64-69 and 745-750 of SEQ ID NO: 9 and residues 22-23 and 249-250 of SEQ ID NO: 10); the plain text corresponds to the rhesus macaque IgG1 hinge-CH2-CH3 sequence (residues 70-744 of SEQ ID NO: 9 and residues 24-248 of SEQ ID NO: 10); and the underlined text corresponds to rhesus macaque TL1A extracellular domain sequence (residues 751-1290 of SEQ ID NO: 9 and residues 251-429 of SEQ ID NO: 10).

In some embodiments, the human TL1A polypeptide comprises or consists of amino acid residues 68-252 from the extracellular domain of human TL1A.

Also, by way of non-limiting example, in some embodiments the nucleic acid and amino acid sequences of the TL1A portion of the human TL1A-Ig fusion protein are:

(SEQ ID NO: 11)

cgggcccagggagaggcctgtgtgcagttccaggctctaaaaggacagga gtttgcaccttcacatcagcaagtttatgcacctcttagagcagacggag ataagccaagggcacacctgacagttgtgagacaaactcccacacagcac tttaaaaatcagttcccagctctgcactgggaacatgaactaggcctggc cttcaccaagaaccgaatgaactataccaacaaattcctgctgatcccag agtcgggagactacttcatttactcccaggtcacattccgtgggatgacc tctgagtgcagtgaaatcagacaagcaggccgaccaaacaagccagactc catcactgtggtcatcaccaaggtaacagacagctaccctgagccaaccc agctcctcatggggaccaagtctgtgtgcgaagtaggtagcaactggttc cagcccatctacctcggagccatgttctccttgcaagaaggggacaagct aatggtgaacgtcagtgacatctctttggtggattacacaaaagaagata aaaccttctttggagccttcttactatag (encoding the extracellular domain of human TL1A);

and (SEQ ID NO: 12)

raqgeacvqfgalkgqefapshqqvyaplradgdkprahltvvrqtptqh fknqfpalhwehelglaftknrmnytnkfllipesgdyfiysqvtfrgmt secseirqagrpnkpdsitvvitkvtdsypeptqllmgtksvcevgsnwf qpiylgamfslqegdklmvnvsdislvdytkedktffgafll (the extracellular domain of human TL1A).

In some embodiments the nucleic acid and amino acid sequences of the human Ig molecule (IgG1 hinge-CH2-CH3 sequence) are:

(SEQ ID NO: 13)

tgtgacaaaactcacacatgcccaccgtgcccagcacctgaactcctggg gggaccgtcagtcttcctcttccccccaaaacccaaggacaccctcatga tctcccggacccctgaggtcacatgcgtggtggtggacgtgagccacgaa gaccctgaggtcaagttcaactggtacgtggacggcgtggaggtgcataa tgccaagacaaagccgcgggaggagcagtacaacagcacgtaccgtgtgg tcagcgtcctcaccgtcctgcaccaggactggctgaatggcaaggagtac aagtgcaaggtctccaacaaagccctcccagcccccatcgagaaaaccat ctccaaagccaaagggcagccccgagaaccacaggtgtacaccctgcccc catcccgggatgagctgaccaagaaccaggtcagcctgacctgcctggtc aaaggcttctatcccagcgacatcgccgtggagtgggagagcaatgggca gccggagaacaactacaagaccacgcctcccgtgctggactccgacggct -continued

```
ccttcttcctctacagcaagctcaccgtggacaagagcaggtggcagcag

gggaacgtatctcatgctccgtgatgcatgaggctctgcacaaccactac

acgcagaagagcctctccctgtctccgggtaaa;
and
                                        (SEQ ID NO: 14)
cdkthtcppcpapellggpsvflfppkpkdtlmisrtpevtcvvvdvshe

dpevkfnwyvdgvevhnaktkpreeqynstyrvvsyltvlhqdwlngkey

kckvsnkalpapiektiskakgqprepqvytlppsrdeltknqvsltclv

kgfypsdiavewesngqpennykttppvldsdgsfflyskltvdkerwqg

gnvfscsvmhealhnhytqkslslspgk (the hinge, CH2 and

CH3 region of human IgG).
```

In some embodiments the nucleic acid and amino acid sequences of the human TL1A fusion protein are:

```
                                        (SEQ ID NO: 15)
tgtgacaaaactcacacatgcccaccgtgcccagcacctgaactcctggg

gggaccgtcagtcttcctcttccccccaaaacccaaggacaccctcatga

tctcccggacccctgaggtcacatgcgtggtggtggacgtgagccacgaa

gaccctgaggtcaagttcaactggtacgtggacggcgtggaggtgcataa

tgccaagacaaagccgcgggaggagcagtacaacagcacgtaccgtgtgg

tcagcgtcctcaccgtcctgcaccaggactggctgaatggcaaggagtac

aagtgcaaggtctccaacaaagccctcccagcccccatcgagaaaaccat

ctccaaagccaaagggcagccccgagaaccacaggtgtacaccctgcccc

catcccgggatgagctgaccaagaaccaggtcagcctgacctgcctggtc

aaaggcttctatcccagcgacatcgccgtggagtgggagagcaatgggca

gccggagaacaactacaagaccacgcctcccgtgctggactccgacggct

ccttcttcctctacagcaagctcaccgtggacaagagcaggtggcagcag

gggaacgtcttctcatgctccgtgatgcatgaggctctgcacaaccacta

cacgcagaagagcctctccctgtctccgggtaaagaattccgggcccagg

gagaggcctgtgtgcagttccaggctctaaaaggacaggagtttgcacct

tcacatcagcaagtttatgcacctettagagcagacggagataagccaag

ggcacacctgacagttgtgagacaaactcccacacagcactttaaaaatc

agtteccagctctgcactgggaacatgaactaggcctggccttcaccaag

aaccgaatgaactataccaacaaattcctgctgatcccagagtcgggaga

ctacttcatttactcccaggtcacattccgtgggatgacctctgagtgca

gtgaaatcagacaagcaggccgaccaaacaagccagactccatcactgtg

gtcatcaccaaggtaacagacagctaccctgagccaacccagctcctcat

ggggaccaagtctgtgtgcgaagtaggtagcaactggttccagcccatct

acctcggagccatgttctecttgcaagaaggggacaagctaatggtgaac

gtcagtgacatctctttggtggattacacaaaagaagataaaaccttctt

tggagccttcttactatag;
and
                                        (SEQ ID NO: 16)
cdkthtcppcpapellggpsvflfppkpkdtlmisrtpevtcvvvdvshe

dpevkfnwyvdgvevhnaktkpreeqynstyrvvsvltvlhqdwlngkey

kckvsnkalpapiektiskakgqprepqvytlppsrdeltknqvsltclv

kgfypsdiavewesngqpennykttppvldsdgsfflyskltvdkerwqq

gnvfscsvmhealhnhytqkslslspgkefraggeacvqfgalkgqefap

shqgvyaplradqdkprahltvvrgtptghfknqfpalhwehelglaftk

nrmnytnkfllipesgdyfiysqvtfrgmtsecseirqagrpnkpdsitv

vitkvtdsypeptqllmgtksvcevqsnwfqpiylqamfslqegdklmvn

vsdislvdytkedktffgafll.
```

In the above exemplary fusion protein sequences (human nucleic acid and amino acid sequences, SEQ ID NOs: 15 and 16), the bold and italicized residues correspond to the restriction enzyme cloning site (residues 685-690 of SEQ ID NO: 15 and residues 229-230 of SEQ ID NO: 16), the residues occurring before the restriction enzyme cloning site (plain text) correspond to the human IgG1 hinge-CH2-CH3 sequence (residues 1-684 of SEQ ID NO: 15 and residues 1-228 of SEQ ID NO: 16), and the residues following the restriction enzyme cloning site (underlined text) correspond to the human TL extracellular domain sequence (residues 691-1269 of SEQ ID NO: 15 and residues 231-422 of SEQ ID NO: 16).

Murine TL1A fusion proteins were also constructed and encompassed herein. The methods for their construction, and the functional characterization of an exemplary murine fusion protein, are described in detail in Khan, S. Q., et al. (2013) "Cloning, expression, and functional characterization of TL1A-Ig." J Immunol 190:1540-1550.

In addition to the polynucleotide sequences described above, polynucleotide sequences comprising nucleotide sequences having certain percent sequence identities to any of the aforementioned sequences are also encompassed. For example, polynucleotides encompassed herein can have about, e.g., 80%, 85%, 90%, 91%, 92%, 93%, 94%, 95%, 96%, 97%, 98%, 99%, or 100% sequence identity to any of the aforementioned polynucleotides (e.g., encoding human or rhesus macaque TL1A and/or immunoglobulin polynucleotides). Such polynucleotide sequences can include, e.g., variants and species orthologs, and preferably hybridize under conditions of moderate or high stringency as described above. A variant, e.g. of a TL1A polynucleotide, is a modified or altered gene or DNA sequence, e.g., mutant. "Mutant" and "mutation" refer to any detectable change in genetic material (e.g., DNA) or any process, mechanism, or result of such a change. This includes gene mutations, in which the structure (e.g., DNA sequence) of a gene is altered, any gene or DNA arising from any mutation process, and any expression product (e.g., protein, e.g., TL1A) expressed by a modified gene or DNA sequence.

Modification of the polypeptide may be effected by any means known to those of skill in this art. Such methods may rely on modification of DNA encoding the fusion protein and expression of the modified DNA. DNA encoding one of the TL1A fusion proteins discussed above may be mutagenized using standard methodologies, including those described below. For example, cysteine residues that may otherwise facilitate multimer formation or promote particular molecular conformations can be deleted from a polypeptide or replaced, e.g., cysteine residues that are responsible for aggregate formation. Conversely, where aggregation is desired, e.g., to produce dimers or trimers and/or dimers of trimers, additional cysteine residues can be introduced, e.g., to the hinge region of an Ig molecule. If necessary, the identity of cysteine residues that contribute to aggregate formation may be determined empirically, by deleting and/or replacing a cysteine residue and ascertaining whether the resulting protein aggregates in solutions containing physiologically acceptable buffers and salts. Moreover, conservative substitutions of amino acids are well-known and may be made generally without altering the biological activity of the resulting TL1A fusion protein molecule. For example, such substitutions are generally made by interchanging within the groups of polar residues, charged residues, hydrophobic residues, small residues, and the like. If necessary, such substitutions may be determined empirically merely by testing the resulting modified protein for the ability to bind to the appropriate cell surface receptors (e.g., TNFRSF25) and/or trigger desired effects (e.g., Treg cell proliferation) in in vitro biological assays.

Orthologs are genes in different species that apparently evolved from a common ancestral gene by speciation. Normally, orthologs retain the same function through the course of evolution. Identification of orthologs can provide reliable prediction of gene function in newly sequenced genomes. Sequence comparison algorithms that can be used to identify orthologs include without limitation BLAST, FASTA, DNA Strider, and the GCG pileup program. Orthologs often have high sequence similarity. Contemplated for use herein are all orthologs of TL1A that retain the ability to specifically bind to TNFRSF25, and preferably, to human TNFRSF25.

In some embodiments, truncated components (i.e., fragments) of TL1A polypeptide, hinge region polypeptide, linker, etc., for use in a TL1A fusion protein, are provided. Also provided are nucleic acids encoding a TL1A fusion protein having such truncated components. A truncated molecule may be any molecule that contains less than a full length version of the molecule. Truncated molecules provided by the present disclosure may include truncated biological polymers and, in some embodiments of the disclosure, such truncated molecules may be truncated nucleic acid molecules or truncated polypeptides. Truncated nucleic acid molecules have less than the full length nucleotide sequence of a known or described nucleic acid molecule, where such a known or described nucleic acid molecule may be a naturally occurring, a synthetic or a recombinant nucleic acid molecule. Thus, for example, truncated nucleic acid molecules that correspond to a gene sequence contain less than the full length gene where the gene contains coding and non-coding sequences, promoters, enhancers and other regulatory sequences, flanking sequences and the like, and other functional and non-functional sequences that are recognized as part of the gene. In another example, truncated nucleic acid molecules that correspond to a mRNA sequence contain less than the full length mRNA transcript, which may include various translated and non-translated regions as well as other functional and non-functional sequences.

Truncated molecules can be polypeptides that contain less than the full length amino acid sequence of a particular protein or polypeptide component. As used herein "deletion" has its common meaning as understood by those familiar with the art, and may refer to molecules that lack one or more of a portion of a sequence from either terminus or from a non-terminal region, relative to a corresponding full length molecule, for example, as in the case of truncated molecules provided herein. Truncated molecules that are linear biological polymers such as nucleic acid molecules or polypeptides may have one or more of a deletion from either terminus of the molecule or a deletion from a non-terminal region of the molecule, where such deletions may be deletions of 1-550, 1-500, 1-450, 1-400, 1-350, 1-300, 1-250, 1-200, 1-150, 1-100, 1-50, 1-25, 1-20, 15, 1-10, or 1-5 contiguous nucleotide residues. Truncated polypeptide molecules may have a deletion of 1-250, 1-200, 1-150, 1-100, 1-50, 1-25, 1-20, 1-15, 1-10, or 1-5 contiguous amino acid residues. Truncation molecules (i.e., fragments) can include, e.g., a portion of the extracellular domain of TL1A that specifically bind to TNFRSF25.

Exemplary truncated TL1A polypeptides that can be used in the compositions and methods disclosed herein include, e.g., a fragment containing, e.g. 421 or fewer continuous amino acids of SEQ ID NO: 16, e.g., 400-420, 350-400, 300-350, 250-300, 200-250, 150-200, 100-150, 50-100, 25-75, 50-75, 25-75, 15-25, or 10-20 contiguous amino acids of SEQ ID NO: 16. Any fragment of TL1A polypeptide (or nucleic acid) is contemplated for use as described herein, provided that the fragment is functionally active, i.e., retains the ability to specifically bind to TNFRSF25 (or, for nucleic acid fragments, encodes a polypeptide that is functionally active).

The present disclosure further relates to variants of the herein referenced nucleic acids which encode fragments, analogs and/or derivatives of a TL1A fusion protein. The variants of the nucleic acids encoding TL1A fusion proteins may be naturally occurring allelic variants of the nucleic acids or non-naturally occurring variants. As is known in the art, an allelic variant is an alternate form of a nucleic acid sequence which may have at least one of a substitution, a deletion or an addition of one or more nucleotides, any of which does not substantially alter the function of the encoded TL1A fusion protein.

Variants and derivatives of TL1A fusion protein may be obtained by mutations of nucleotide sequences encoding TL1A fusion proteins. Alterations of the native amino acid sequence may be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene wherein predetermined codons can be altered by substitution, deletion or insertion. Exemplary methods of making such alterations are disclosed by Walder et al. (Gene 42:133, 1986); Bauer et al. (Gene 37:73, 1985); Craik (BioTechniques, January 1985, 12-19); Smith et al. (Genetic Engineering: Principles and Methods BioTechniques, January 1985, 12-19); Smith et al. (Genetic Engineering: Principles and Methods, Plenum Press, 1981); Kunkel (Proc. Natl. Acad. Sci. USA 82:488, 1985); Kunkel et al. (Methods in Enzymol. 154:367, 1987); and U.S. Pat. Nos. 4,518,584 and 4,737,462.

As an example, modification of DNA may be performed by site-directed mutagenesis of DNA encoding the protein combined with the use of DNA amplification methods using primers to introduce and amplify alterations in the DNA template, such as PCR splicing by overlap extension (SOE). Site-directed mutagenesis is typically effected using a phage vector that has single- and double-stranded forms, such as M13 phage vectors, which are well-known and commercially available. Other suitable vectors that contain a single-stranded phage origin of replication may be used (see, e.g., Veira et al., Meth. Enzymol. 15:3, 1987). In general, site-directed mutagenesis is performed by preparing a single-stranded vector that encodes the protein of interest (e.g., all or a component portion of a given TL1A fusion protein). An oligonucleotide primer that contains the desired mutation within a region of homology to the DNA in the single-stranded vector is annealed to the vector followed by addition of a DNA polymerase, such as E. coli DNA polymerase I (Klenow fragment), which uses the double stranded region as a primer to produce a heteroduplex in which one strand encodes the altered sequence and the other the original sequence. The heteroduplex is introduced into appropriate bacterial cells and clones that include the desired mutation are selected. The resulting altered DNA molecules may be expressed recombinantly in appropriate host cells to produce the modified protein.

Equivalent DNA constructs that encode various additions or substitutions of amino acid residues or sequences, or deletions of terminal or internal residues or sequences not needed for biological activity are also encompassed herein. For example, and as discussed above, sequences encoding Cys residues that are not desirable or essential for biological activity can be altered to cause the Cys residues to be deleted or replaced with other amino acids, preventing formation of incorrect intramolecular disulfide bridges upon renaturation. Alternatively, additional Cys residues can be introduced to facilitate multimerization.

Binding domains for TL and binding interactions of TL with its receptor, TNFRSF25 have been characterized, such that one having ordinary skill in the art may readily select appropriate polypeptide domains for inclusion in the encoded products of the instant expression constructs, and will understand which nucleic acid and/or amino acid residues are amenable to modification (e.g., substitution, deletion, addition, etc.). See e.g., Zhan et al. Biochemistry. 2009 Aug. 18; 48(32):7636-45. Further, assays for determining whether any of the above described polypeptides specifically bind to TNFRSF25 are known in the art and described in Example 1, as discussed above.

Nucleic acids and oligonucleotides for use as described herein can be synthesized by any method known to those of skill in this art (see, e.g., WO 93/01286, U.S. application Ser. No. 07/723,454; U.S. Pat. Nos. 5,218,088; 5,175,269; 5,109,124). Identification of oligonucleotides and nucleic acid sequences for use in the present disclosure involves methods well known in the art. For example, the desirable properties, lengths and other characteristics of useful oligonucleotides are well known. In certain embodiments, synthetic oligonucleotides and nucleic acid sequences may be designed that resist degradation by endogenous host cell nucleolytic enzymes by containing such linkages as: phosphorothioate, methylphosphonate, sulfone, sulfate, ketyl, phosphorodithioate, phosphoramidate, phosphate esters, and other such linkages that have proven useful in antisense applications (see, e.g., Agrawal and Goodchild; Tetrehedron Lett. 28:3539-3542 (1987); Miller et al., J. Am. Chem. Soc. 93:6657-6665 (1971); Stec et al., Tetrehedron Lett. 26:2191-2194 (1985); Moody et al., Nucl. Acids Res. 12:4769-4782 (1989); Uznanski et al., Nucl. Acids Res. (1989); Letsinger et al., Tetrahedron 40:137-143 (1984); Eckstein, Annu Rev. Biochem. 54:367-402 (1985); Eckstein, Trends Biol. Sci. 14:97-100 (1989); Stein In: Oligodeoxynucleotides. Antisense Inhibitors of Gene Expression, Cohen, Ed, Macmillan Press, London, pp. 97-117 (1989); Jager et al., Biochemistry 27:7237-7246 (1988)).

Host organisms include those organisms in which recombinant production of TL1A fusion products encoded by the recombinant constructs of the present disclosure may occur, such as bacteria (for example, E. coli), yeast (for example, Saccharomyces cerevisiae and Pichia pastoris), insect cells and mammals, including in vitro and in vivo expression. Host organisms thus may include organisms for the construction, propagation, expression or other steps in the production of the compositions provided herein; hosts also include subjects in which immune responses take place, as described above. Presently preferred host organisms are E. coli bacterial strains, inbred murine strains and murine cell lines, non-human primate subjects and cell lines, and human cells, subjects and cell lines.

The DNA construct encoding the desired TL1A fusion protein is introduced into a plasmid for expression in an appropriate host. The host can be a bacterial host. The sequence encoding the ligand or nucleic acid binding domain is preferably codon-optimized for expression in the particular host. Thus, for example, if a human TL1A fusion protein is expressed in bacteria, the codons would be optimized for bacterial usage. For small coding regions, the gene can be synthesized as a single oligonucleotide. For larger proteins, splicing of multiple oligonucleotides, mutagenesis, or other techniques known to those in the art may be used. The sequences of nucleotides in the plasmids that are regulatory regions, such as promoters and operators, are operationally associated with one another for transcription. The sequence of nucleotides encoding a TL1A fusion protein may also include DNA encoding a secretion signal, whereby the resulting peptide is a precursor protein. The resulting processed protein may be recovered from the periplasmic space or the fermentation medium.

The DNA plasmids can also include a transcription terminator sequence. As used herein, a "transcription terminator region" is a sequence that signals transcription termination. The entire transcription terminator may be obtained from a protein-encoding gene, which may be the same or different from the inserted TL1A fusion protein encoding gene or the source of the promoter. Transcription terminators are optional components of the expression systems herein.

The plasmids used herein include a promoter in operative association with the DNA encoding the protein or polypeptide of interest and are designed for expression of proteins in a suitable host as described above (e.g., bacterial, murine or human) depending upon the desired use of the plasmid (e.g., administration of a vaccine containing TL1A fusion protein encoding sequences). Suitable promoters for expression of proteins and polypeptides herein are widely available and are well known in the art. Inducible promoters or constitutive promoters that are linked to regulatory regions are preferred. Such promoters include, but are not limited to, the T7 phage promoter and other T7-like phage promoters, such as the T3, T5 and SP6 promoters, the trp, 1 pp, and lac promoters, such as the lacUV5, from E. coli; the P10 or polyhedrin gene promoter of baculovirus/insect cell expression systems (see, e.g., U.S. Pat. Nos. 5,243,041, 5,242,687, 5,266,317, 4,745,051, and 5,169,784) and inducible promoters from other eukaryotic expression systems. This may also include the human ferritin promoter. For expression of the proteins such promoters are inserted in a plasmid in operative linkage with a control region such as the lac operon.

Preferred promoter regions are those that are inducible and functional in E. coli. Examples of suitable inducible promoters and promoter regions include, but are not limited to: the E. coli lac operator responsive to isopropyl β-D-thiogalactopyranoside (IPTG; see Nakamura et al., Cell 18:1109-1117, 1979); the metallothionein promoter metal-regulatory-elements responsive to heavy-metal (e.g., zinc) induction (see, e.g., U.S. Pat. No. 4,870,009 to Evans et al.); the phage T7lac promoter responsive to IPTG (see, e.g., U.S.

Pat. No. 4,952,496; and Studier et al., Meth. Enzymol. 185:60-89, 1990) and the TAC promoter.

The plasmids may optionally include a selectable marker gene or genes that are functional in the host. A selectable marker gene includes any gene that confers a phenotype on bacteria that allows transformed bacterial cells to be identified and selectively grown from among a vast majority of untransformed cells. Suitable selectable marker genes for bacterial hosts, for example, include the ampicillin resistance gene (Ampr), tetracycline resistance gene (Tc$^r$) and the kanamycin resistance gene (Kan).

The plasmids may also include DNA encoding a signal for secretion of the operably linked protein. Secretion signals suitable for use are widely available and are well known in the art. Prokaryotic and eukaryotic secretion signals functional in E. coli may be employed. The presently preferred secretion signals include, but are not limited to, those encoded by the following E. coli genes: ompA, ompT, ompF, ompC, beta-lactamase, and alkaline phosphatase, and the like (von Heijne, J. Mol. Biol. 184:99-105, 1985). In addition, the bacterial pelB gene secretion signal (Lei et al., J. Bacteriol. 169:4379, 1987), the phoA secretion signal, and the cek2 functional in insect cell may be employed. Other prokaryotic and eukaryotic secretion signals known to those of skill in the art may also be employed (see, e.g., von Heijne, J. Mol. Biol. 184:99-105, 1985). Using the methods described herein, one of skill in the art can substitute secretion signals that are functional in either yeast, insect or mammalian cells to secrete proteins from those cells.

In some embodiments preferred plasmids for transformation of E. coli cells include the pET expression vectors (e.g., pET-11 a, pET-12a-c, pET-15b; see U.S. Pat. No. 4,952,496; available from Novagen, Madison, Wis.). Other preferred plasmids include the pKK plasmids, particularly pKK 223-3, which contains the tac promoter (Brosius et al., Proc. Natl. Acad. Sci. 81:6929, 1984; Ausubel et al., Current Protocols in Molecular Biology; U.S. Pat. Nos. 5,122,463, 5,173,403, 5,187,153, 5,204,254, 5,212,058, 5,212,286, 5,215,907, 5,220,013, 5,223,483, and 5,229,279). Plasmid pKK has been modified by replacement of the ampicillin resistance gene with a kanamycin resistance gene. (Available from Pharmacia; obtained from pUC4K, see, e.g., Vieira et al. (Gene 19:259-268, 1982; and U.S. Pat. No. 4,719,179.) Baculovirus vectors, such as pBlueBac (also called pJVETL and derivatives thereof), particularly pBlueBac III (see, e.g., U.S. Pat. Nos. 5,278,050, 5,244,805, 5,243,041, 5,242,687, 5,266,317, 4,745,051, and 5,169,784; available from Invitrogen, San Diego) may also be used for expression of the polypeptides in insect cells. Other plasmids include the pIN-IIIompAplasmids (see U.S. Pat. No. 4,575,013; see also Duffaud et al., Meth. Enz. 153:492-507, 1987), such as pIN-IIIompA2.

In some embodiments, the DNA molecule is replicated in bacterial cells, preferably in E. coli. The preferred DNA molecule also includes a bacterial origin of replication, to ensure the maintenance of the DNA molecule from generation to generation of the bacteria. In this way, large quantities of the DNA molecule can be produced by replication in bacteria. Preferred bacterial origins of replication include, but are not limited to, the fl-ori and col E1 origins of replication. Preferred hosts contain chromosomal copies of DNA encoding T7 RNA polymerase operably linked to an inducible promoter, such as the lacUV promoter (see U.S. Pat. No. 4,952,496). Such hosts include, but are not limited to, lysogens E. coli strains HMS174(DE3)pLysS, BL21 (DE3)pLysS, HMS174(DE3) and BL21(DE3). Strain BL21 (DE3) is preferred. The pLys strains provide low levels of T7 lysozyme, a natural inhibitor of T7 RNA polymerase.

The DNA molecules provided may also comprise a gene coding for a repressor protein. The repressor protein is capable of repressing the transcription of a promoter that contains sequences of nucleotides to which the repressor protein binds. The promoter can be de-repressed by altering the physiological conditions of the cell. For example, the alteration can be accomplished by adding to the growth medium a molecule that inhibits the ability to interact with the operator or with regulatory proteins or other regions of the DNA or by altering the temperature of the growth media. Repressor proteins include, but are not limited to the E. coli lad repressor responsive to IPTG induction, the temperature sensitive λc1857 repressor, and the like.

In general, recombinant constructs will also contain elements necessary for transcription and translation. In particular, such elements are preferred where the recombinant expression construct containing nucleic acid sequences encoding TL1A fusion proteins is intended for expression in a host cell or organism. In certain embodiments of the present disclosure, cell type preferred or cell type specific expression of a cell TL1A fusion protein encoding gene may be achieved by placing the gene under regulation of a promoter. The choice of the promoter will depend upon the cell type to be transformed and the degree or type of control desired. Promoters can be constitutive or active and may further be cell type specific, tissue specific, individual cell specific, event specific, temporally specific or inducible. Cell-type specific promoters and event type specific promoters are preferred. Examples of constitutive or nonspecific promoters include the SV40 early promoter (U.S. Pat. No. 5,118,627), the SV40 late promoter (U.S. Pat. No. 5,118,627), CMV early gene promoter (U.S. Pat. No. 5,168,062), and adenovirus promoter. In addition to viral promoters, cellular promoters can also be used. In particular, cellular promoters for the so-called housekeeping genes are useful. Viral promoters are preferred, because generally they are stronger promoters than cellular promoters. Promoter regions have been identified in the genes of many eukaryotes including higher eukaryotes, such that suitable promoters for use in a particular host can be readily selected by those skilled in the art.

Inducible promoters may also be used. These promoters include MMTV LTR (PCT WO 91/13160), inducible by dexamethasone; metallothionein promoter, inducible by heavy metals; and promoters with cAMP response elements, inducible by cAMP. By using an inducible promoter, the nucleic acid sequence encoding a TL1A fusion protein may be delivered to a cell by the expression construct and will remain quiescent until the addition of the inducer. This allows further control on the timing of production of the gene product.

Event-type specific promoters are active or up-regulated only upon the occurrence of an event, such as tumorigenicity or viral infection. The HIV LTR is a well-known example of an event-specific promoter. The promoter is inactive unless the tat gene product is present, which occurs upon viral infection. Some event-type promoters are also tissue-specific.

Additionally, promoters that are coordinately regulated with a particular cellular gene may be used. For example, promoters of genes that are coordinately expressed may be used when expression of a particular TL1A fusion protein-encoding gene is desired in concert with expression of one or more additional endogenous or exogenously introduced genes. This type of promoter is especially useful when one knows the pattern of gene expression relevant to induction of an immune response in a particular tissue of the immune system, so that specific immunocompetent cells within that tissue may be activated or otherwise recruited to participate in the immune response.

In addition to the promoter, repressor sequences, negative regulators, or tissue-specific silencers may be inserted to reduce non-specific expression of TL1A fusion protein encoding genes in certain situations, such as, for example, a host that is transiently immunocompromised as part of a therapeutic strategy. Multiple repressor elements may be inserted in the promoter region. Repression of transcription is independent on the orientation of repressor elements or distance from the promoter. One type of repressor sequence is an insulator sequence. Such sequences inhibit transcription (Dunaway et al., Mol Cell Biol 17: 182-9, 1997; Gdula et al., Proc Natl Acad Sci USA 93:9378-83, 1996, Chan et al., J Virol 70: 5312-28, 1996; Scott and Geyer, EMBO J. 14:6258-67, 1995; Kalos and Fournier, Mol Cell Biol 15:198-207, 1995; Chung et al., Cell 74: 505-14, 1993) and will silence background transcription.

Repressor elements have also been identified in the promoter regions of the genes for type II (cartilage) collagen, choline acetyltransferase, albumin (Hu et al., J. Cell Growth Differ. 3(9):577-588, 1992), phosphoglycerate kinase (PGK-2) (Misuno et al., Gene 119(2):293-297, 1992), and in the 6-phosphofructo-2-kinase/fructose-2,6-bisphosphatase gene. (Lemaigre et al., Mol. Cell. Biol. 11(2):1099-1106.) Furthermore, the negative regulatory element Tse-1 has been identified in a number of liver specific genes, and has been shown to block cAMP response element—(CRE) mediated induction of gene activation in hepatocytes. (Boshart et al., Cell 61(5):905-916, 1990).

In some embodiments, elements that increase the expression of the desired product are incorporated into the construct. Such elements include internal ribosome binding sites (IRES; Wang and Siddiqui, Curr. Top. Microhiol. Immunol 203:99, 1995; Ehrenfeld and Semler, Curr. Top. Microhiol. Immunol. 203:65, 1995; Rees et al., Biotechniques 20:102, 1996; Sugimoto et al., Biotechnology 12:694, 1994). IRES increase translation efficiency. Other sequences may also enhance expression, e.g., for some genes, sequences especially at the 5' end inhibit transcription and/or translation. These sequences are usually palindromes that can form hairpin structures. Any such sequences in the nucleic acid to be delivered are generally deleted. Expression levels of the transcript or translated product are assayed to confirm or ascertain which sequences affect expression. Transcript levels may be assayed by any known method, including Northern blot hybridization, RNase probe protection and the like. Protein levels may be assayed by any known method, including ELISA, western blot, immunocytochemistry or other well-known techniques.

Other elements may be incorporated into the TL1A fusion protein encoding constructs of the present disclosure. For example, the construct can include a transcription terminator sequence, including a polyadenylation sequence, splice donor and acceptor sites, and an enhancer. Other elements useful for expression and maintenance of the construct in mammalian cells or other eukaryotic cells may also be incorporated (e.g., origin of replication). Because the constructs can be conveniently produced in bacterial cells, elements that are necessary for, or that enhance, propagation in bacteria can be incorporated. Such elements include an origin of replication, a selectable marker and the like.

As provided herein, an additional level of controlling the expression of nucleic acids encoding TL1A fusion proteins delivered to cells using the constructs disclosed herein may be provided by simultaneously delivering two or more differentially regulated nucleic acid constructs. The use of such a multiple nucleic acid construct approach may permit coordinated regulation of an immune response such as, for example, spatiotemporal coordination that depends on the cell type and/or presence of another expressed encoded component. Those familiar with the art will appreciate that multiple levels of regulated gene expression may be achieved in a similar manner by selection of suitable regulatory sequences, including but not limited to promoters, enhancers and other well known gene regulatory elements.

The present disclosure also relates to vectors, and to constructs prepared from known vectors that include nucleic acids of the present disclosure, and in particular to "recombinant expression constructs" that include any nucleic acids encoding TL1A fusion proteins and polypeptides as provided above; to host cells which are genetically engineered with vectors and/or constructs and to methods of administering expression constructs containing nucleic acid sequences encoding such TL1A fusion proteins disclosed herein, or fragments, orthologs or variants thereof, by recombinant techniques. TL1A fusion proteins can be expressed in virtually any host cell under the control of appropriate promoters, depending on the nature of the construct (e.g., type of promoter, as described above), and on the nature of the desired host cell (e.g., whether postmitotic terminally differentiated or actively dividing; e.g., whether the expression construct occurs in host cell as an episome or is integrated into host cell genome). Appropriate cloning and expression vectors for use with prokaryotic and eukaryotic hosts are described by Sambrook, et al., Molecular Cloning: A Laboratory Manual, Second Edition, Cold Spring Harbor, N.Y., (1989); as noted above, in some embodiments, recombinant expression is conducted in mammalian cells that have been transfected or transformed with the recombinant expression constructs described herein.

Typically, the constructs are derived from plasmid vectors. A preferred construct is a modified pNASS vector (Clontech, Palo Alto, Calif.), which has nucleic acid sequences encoding an ampicillin resistance gene, a polyadenylation signal and a T7 promoter site. Other suitable mammalian expression vectors are well known (see, e.g., Ausubel et al., 1995; Sambrook et al., supra; see also, e.g., catalogues from Invitrogen, San Diego, Calif.; Novagen, Madison, Wis.; Pharmacia, Piscataway, N.J.; and others). Presently preferred constructs may be prepared that include a dihydrofolate reductase (DHFR) encoding sequence under suitable regulatory control, for promoting enhanced production levels of the TL1A fusion protein, which levels result from gene amplification following application of an appropriate selection agent (e.g., methotrexate).

Generally, recombinant expression vectors will include origins of replication and selectable markers permitting transformation of the host cell, and a promoter derived from a highly-expressed gene to direct transcription of a downstream structural sequence, as described above. The heterologous structural sequence is assembled in appropriate phase with translation initiation and termination sequences. Thus, for example, the TL1A fusion protein encoding nucleic acids as provided herein may be included in any one of a variety of expression vector constructs as a recombinant expression construct for expressing a TL1A fusion protein in a host cell. In certain preferred embodiments the constructs are included in formulations that are administered in vivo. Such vectors and constructs include chromosomal, nonchromosomal and synthetic DNA sequences, e.g., derivatives of SV40; bacterial plasmids; phage DNA; yeast plasmids; vectors derived from combinations of plasmids and phage DNA, viral DNA, such as vaccinia, adenovirus, fowl pox virus, and pseudorabies, or replication deficient retroviruses as described below. However, any other vector may be used for preparation of a recombinant expression construct, and in preferred embodiments such a vector will be replicable and viable in the host.

The appropriate DNA sequence(s) may be inserted into the vector by a variety of procedures. In general, the DNA sequence is inserted into an appropriate restriction endonuclease site(s) by procedures known in the art. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described, for example, in Ausubel et al. (1993 Current Protocols in Molecular Biology, Greene Publ. Assoc. Inc. & John Wiley & Sons, Inc., Boston, Mass.); Sambrook et al. (1989 Molecular Cloning, Second Ed., Cold Spring Harbor Laboratory, Plainview, N.Y.); Maniatis et al. (1982 Molecular Cloning, Cold Spring Harbor Laboratory, Plainview, N.Y.); Glover (Ed.) (1985 DNA Cloning Vol. I and II, IRL Press, Oxford, UK); Hames and Higgins (Eds.), (1985 Nucleic Acid Hybridization, IRL Press, Oxford, UK); and elsewhere.

The DNA sequence in the expression vector is operatively linked to at least one appropriate expression control sequences (e.g., a constitutive promoter or a regulated promoter) to direct mRNA synthesis. Representative examples of such expression control sequences include promoters of eukaryotic cells or their viruses, as described above. Promoter regions can be selected from any desired gene using CAT (chloramphenicol transferase) vectors or other vectors with selectable markers. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art, and preparation of certain particularly preferred recombinant expression constructs containing at least one promoter or regulated promoter operably linked to a nucleic acid encoding an TL1A fusion protein is described herein.

Transcription of the DNA encoding the polypeptides of the present disclosure by higher eukaryotes may be increased by inserting an enhancer sequence into the vector. Enhancers are cis-acting elements of DNA, usually about from 10 to 300 by that act on a promoter to increase its transcription. Examples including the SV40 enhancer on the late side of the replication origin by 100 to 270, a cytomegalovirus early promoter enhancer, the polyoma enhancer on the late side of the replication origin, and adenovirus enhancers.

As provided herein, in some embodiments the vector may be a viral vector such as a retroviral vector. (Miller et al., 1989 BioTechniques 7:980; Coffin and Varmus, 1996 Retroviruses, Cold Spring Harbor Laboratory Press, NY.) For example, retroviruses from which the retroviral plasmid vectors may be derived include, but are not limited to, Moloney Murine Leukemia Virus, spleen necrosis virus, retroviruses such as Rous Sarcoma Virus, Harvey Sarcoma virus, avian leukosis virus, gibbon ape leukemia virus, human immunodeficiency virus, adenovirus, Myeloproliferative Sarcoma Virus, and mammary tumor virus.

Retroviruses are RNA viruses which can replicate and integrate into the genome of a host cell via a DNA intermediate. This DNA intermediate, or provirus, may be stably integrated into the host cell DNA. According to certain embodiments of the present disclosure, an expression construct may contain a retrovirus into which a foreign gene that encodes a foreign protein is incorporated in place of normal retroviral RNA. When retroviral RNA enters a host cell coincident with infection, the foreign gene is also introduced into the cell, and may then be integrated into host cell DNA as if it were part of the retroviral genome. Expression of this foreign gene within the host results in expression of the foreign protein.

Most retroviral vector systems which have been developed for gene therapy are based on murine retroviruses. Such retroviruses exist in two forms, as free viral particles referred to as virions, or as proviruses integrated into host cell DNA. The virion form of the virus contains the structural and enzymatic proteins of the retrovirus (including the enzyme reverse transcriptase), two RNA copies of the viral genome, and portions of the source cell plasma membrane containing viral envelope glycoprotein. The retroviral genome is organized into four main regions: the Long Terminal Repeat (LTR), which contains cis-acting elements necessary for the initiation and termination of transcription and is situated both 5' and 3' of the coding genes, and the three coding genes gag, pol, and env. These three genes gag, pol, and env encode, respectively, internal viral structures, enzymatic proteins (such as integrase), and the envelope glycoprotein (designated gp70 and p15e) which confers infectivity and host range specificity of the virus, as well as the "R" peptide of undetermined function.

Separate packaging cell lines and vector producing cell lines have been developed because of safety concerns regarding the uses of retroviruses, including their use in expression constructs as provided by the present disclosure. Briefly, this methodology employs the use of two components, a retroviral vector and a packaging cell line (PCL). The retroviral vector contains long terminal repeats (LTRs), the foreign DNA to be transferred and a packaging sequence (y). This retroviral vector will not reproduce by itself because the genes which encode structural and envelope proteins are not included within the vector genome. The PCL contains genes encoding the gag, pol, and env proteins, but does not contain the packaging signal "y". Thus, a PCL can only form empty virion particles by itself. Within this general method, the retroviral vector is introduced into the PCL, thereby creating a vector-producing cell line (VCL). This VCL manufactures virion particles containing only the retroviral vector's (foreign) genome, and therefore has previously been considered to be a safe retrovirus vector for therapeutic use.

"Retroviral vector construct" refers to an assembly which is capable of directing the expression of a sequence(s) or gene(s) of interest, such as TL1A fusion protein encoding nucleic acid sequences. Briefly, the retroviral vector construct must include a 5' LTR, a tRNA binding site, a packaging signal, an origin of second strand DNA synthesis and a 3' LTR. A wide variety of heterologous sequences may be included within the vector construct, including for example, sequences which encode a protein (e.g., cytotoxic protein, disease-associated antigen, immune accessory molecule, or replacement gene), or which are useful as a molecule itself (e.g., as a ribozyme or antisense sequence).

Retroviral vector constructs of the present disclosure may be readily constructed from a wide variety of retroviruses, including for example, B, C, and D type retroviruses as well as spumaviruses and lentiviruses (see, e.g., RNA Tumor Viruses, Second Edition, Cold Spring Harbor Laboratory, 1985). Such retroviruses may be readily obtained from depositories or collections such as the American Type Culture Collection ("ATCC"; Rockville, Md.), or isolated from known sources using commonly available techniques. Any of the above retroviruses may be readily utilized in order to assemble or construct retroviral vector constructs, packaging cells, or producer cells of the present disclosure given the disclosure provided herein, and standard recombinant techniques (e.g., Sambrook et al, Molecular Cloning: A Laboratory Manual, 2d ed., Cold Spring Harbor Laboratory Press, 989; Kunkle, PNAS 82:488, 1985).

Suitable promoters for use in viral vectors generally may include, but are not limited to, the retroviral LTR; the SV40 promoter; and the human cytomegalovirus (CMV) promoter described in Miller, et al., Biotechniques 7:980-990 (1989), or any other promoter (e.g., cellular promoters such as eukaryotic cellular promoters including, but not limited to, the histone, pol III, and (β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein, and may be from among either regulated promoters or promoters as described above.

As described above, the retroviral plasmid vector is employed to transduce packaging cell lines to form producer cell lines. Examples of packaging cells which may be transfected include, but are not limited to, the PE501, PA317, .Psi-2, Psi-AM, PA12, T19-14×, VT-19-17-H2, Psi-CRE, Psi-CRIP, GP+E-86, GP+envAm12, and DAN cell lines as described in Miller, Human Gene Therapy, 1:5-14 (1990). The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the TL1A fusion proteins. Such retroviral vector particles then may be employed, to transduce eukaryotic cells, either in vitro or in vivo. The transduced eukaryotic cells will express the nucleic acid sequence(s) encoding the TL1A fusion protein. Eukaryotic cells which may be transduced include, but are not limited to, embryonic stem cells, as well as hematopoietic stem cells, hepatocytes, fibroblasts, circulating peripheral blood mononuclear and polymorphonuclear (PMN) cells including myelomonocytic cells, lymphocytes, myoblasts, tissue macrophages, dendritic cells, Kupffer cells, lymphoid and reticuloendothelia cells of the lymph nodes and spleen, keratinocytes, endothelial cells, and bronchial epithelial cells.

As another example in which a viral vector is used to prepare the recombinant TL1A fusion expression construct, host cells transduced by a recombinant viral construct directing the expression of TL1A fusion proteins or fusion proteins may produce viral particles containing expressed TL1A fusion proteins or fusion proteins that are derived from portions of a host cell membrane incorporated by the viral particles during viral budding.

In some embodiments, the present disclosure relates to host cells containing the above described recombinant TL1A fusion expression constructs. Host cells are genetically engineered (transduced, transformed or transfected) with the vectors and/or expression constructs disclosed herein, which may be, for example, a cloning vector, a shuttle vector or an expression construct. The vector or construct may be, for example, in the form of a plasmid, a viral particle, a phage, etc. The engineered host cells can be cultured in conventional nutrient media modified as appropriate for activating promoters, selecting transformants or amplifying particular genes such as genes encoding TL1A fusion proteins or TL1A fusion proteins. The culture conditions for particular host cells selected for expression, such as temperature, pH and the like, will be readily apparent to the ordinarily skilled artisan.

The host cell can be a higher eukaryotic cell, such as a mammalian cell, or a lower eukaryotic cell, such as a yeast cell, or the host cell can be a prokaryotic cell, such as a bacterial cell. Representative examples of appropriate host cells according to the present disclosure include, but need not be limited to, bacterial cells, such as E. coli, Streptomyces, Salmonella typhimurium; fungal cells, such as yeast; insect cells, such as Drosophila S2 and Spodoptera 519; animal cells, such as CHO, COS or 293 cells; adenoviruses; plant cells, or any suitable cell already adapted to in vitro propagation or so established de novo. The selection of an appropriate host is deemed to be within the scope of those skilled in the art from the teachings herein.

Various mammalian cell culture systems can also be employed to express recombinant protein. Examples of mammalian expression systems include the COS-7 lines of monkey kidney fibroblasts, described by Gluzman, Cell 23:175 (1981), and other cell lines capable of expressing a compatible vector, for example, the C127, 3T3, CHO, HeLa and BHK cell lines. Mammalian expression vectors will contain an origin of replication, a suitable promoter and enhancer, and also any necessary ribosome binding sites, polyadenylation site, splice donor and acceptor sites, transcriptional termination sequences, and 5' flanking nontranscribed sequences, for example as described herein regarding the preparation of TL1A fusion expression constructs. DNA sequences derived from the SV40 splice, and polyadenylation sites may be used to provide the required nontranscribed genetic elements. Introduction of the construct into the host cell can be effected by a variety of methods with which those skilled in the art will be familiar, including but not limited to, for example, calcium phosphate transfection, DEAE Dextran mediated transfection, or electroporation (Davis et al., 1986 Basic Methods in Molecular Biology).

mTOR Inhibitors

In some embodiments, provided herein are combination therapies for, e.g., modulating an antigen-specific immune response, and/or for treating a disease or disorder associated with an antigen-specific immune response, and/or for treating one or more symptoms of the disease or disorder, in a human patient in need thereof. In some embodiments, the methods comprise administering to the patient in need thereof a composition comprising a TNFRSF25 agonist (e.g., TL1A fusion protein, agonistic anti-TNFRSF25 antibody, small molecule agonist of TNFR25 agonist, etc.) and an effective amount of an mTOR inhibitor. In some embodiments, the above methods comprise administering to the patient a combination therapy comprising TNFRSF25 agonist and an mTOR inhibitor.

The mammalian target of rapamycin, commonly known as mTOR, is a serine/threonine protein kinase that regulates cell growth, cell proliferation, cell motility, cell survival, protein synthesis, and transcription. mTOR is a key intermediary in multiple mitogenic signaling pathways and plays a central role in modulating proliferation and angiogenesis in normal tissues and neoplastic processes. mTOR exists within two complexes, mTORC1 and mTORC2. mTORC1 is sensitive to rapamycin analogs (such as temsirolimus or everolimus) and mTORC2 is largely rapamycin-insensitive.

As used herein, the term "mTOR inhibitor" refers to a compound or a ligand that inhibits at least one activity of an mTOR, such as the serine/threonine protein kinase activity on at least one of its substrates (e.g., p70S6 kinase 1, 4E-BP1, AKT/PKB and eEF2). A person skilled in the art can readily determine whether a compound, such as rapamycin or an analogue or derivative thereof, or other compound, antibody, or small molecule, etc., is an mTOR inhibitor. Methods of identifying mTOR inhibitors are known in the art. Examples of mTOR inhibitors include, without limitation, rapamycin (sirolimus), rapamycin derivatives, CI-779, everolimus (Certican™), ABT-578, tacrolimus (FK 506), ABT-578, AP-23675, BEZ-235, OSI-027, QLT-0447, ABI-009, BC-210, salirasib, TAFA-93, deforolimus (AP-23573), temsirolimus (Torisel™), 2-(4-Amino-1-isopropyl-1H-pyrazolo[3,4-d]pyrimidin-3-yl)-1H-indol-5-ol (PP242) and AP-23841.

As used herein, the term "selective mTOR inhibitor" refers to a compound or a ligand that inhibits mTOR activity but does not inhibit PI3K activity. Suitable selective mTOR inhibitors include RAD001. Accordingly, in some embodiments, provided herein is a combination therapy comprising the administration of a TNFRSF25 agonist and the administration of a selective mTOR inhibitor.

Rapamycin is a known macrolide antibiotic produced by Streptomyces hygroscopicus. Suitable derivatives of rapamycin are disclosed, e.g., in WO 94/09010, WO 95/16691, WO 96/41807, U.S. Pat. No. 5,362,718 and WO 99/15530. They may be prepared using the procedures described in these references. Representative rapamycin derivatives are, e.g., 32-deoxorapamycin, 16-pent-2-ynyloxy-32-deoxorapamycin, 16-pent-2-ynyloxy-32(S or R)-dihydro-rapamycin, 16-pent-2-ynyloxy-32(S or R)-dihydro-40-O-(2-hydroxyethyl)-rapamycin, 40-[3-hydroxy-2-(hydroxymethyl)-2-methylpropanoate]-rapamycin (also called CCI779) or 40-epi-(tetrazolyl)-rapamycin (also called ABT578). Rapamycin derivatives may also include the so-called rapalogs, e.g., as disclosed in WO 98/02441 and WO 01/14387, e.g. AP23573, AP23464, AP23675 or AP23841. Further, non-limiting examples of a rapamycin derivative are those disclosed under the name TAFA-93 (a rapamycin prodrug), biolimus-7 or biolimus-9.

In some embodiments, the mTOR inhibitor used in a composition and/or combination therapy provided herein is Everolimus (RAD001) or 2-(4-amino-1-isopropyl-1H-pyrazolo[3,4-d]pyrimidin-3-yl)-1H-indol-5-ol (PP242) (see, e.g., Apsel et al., Nature Chemical to Biology 4, 691-699 (2008)).

Interleukins

In any of the compositions and methods disclosed herein comprising an interleukin, the interleukin can be any interleukin that achieves the desired synergistic effect on the expansion of Treg cells, e.g. when administered in a combination therapy with an agonist of TNFRSF25. In some embodiments, the interleukin is IL-2. In some embodiments, the interleukin is IL-7. In some embodiments, the interleukin is IL-15.

Also encompassed herein are analogs of IL-2, e.g., agonist and partial agonist IL-2 analogs (e.g., IL-2 muteins). Such analogs are known in the art. A non-limiting example of an agonist IL-2 analog includes, e.g., BAY 50-4798 (see Margolin et al. Clin Cancer Res Jun. 1, 2007 13; 3312; for other examples, see also, Imler and Zurawski. J Biol. Chem. 1992 Jul. 5; 267(19):13185-90. Furthermore, in vitro screening assays for determining whether a compound is an IL-2 analog (i.e., maintains the ability to bind to the high affinity IL-2 receptor and initiate T cell proliferation) are known in the art. See, e.g., Zurawski and Zurawski. EMBO J. 1992 November; 11(11): 3905-3910; "The Interleukin 2 Receptor" Annual Review of Cell Biology; Vol. 5: 397-425 (Volume publication date November 1989; and "The Biology of Interleukin-2"; Annual Review of Immunology; Vol. 26: 453-479 (Volume publication date April 2008).

Compositions and Pharmaceutical Compositions

In some embodiments, provided herein are compositions comprising a human TL1A-Ig fusion protein, wherein the fusion protein comprises (a) a first polypeptide comprising a polypeptide that specifically binds to TNFRSF25; and (b) a second polypeptide comprising an immunoglobulin (Ig) polypeptide. In some embodiments, the first polypeptide comprises the extracellular domain of a human TL1A polypeptide or a fragment thereof, and wherein the fragment is capable of specifically binding to TNFRSF25. In some embodiments, when administered to a human in need thereof, the composition reduces the frequency of naive CD4 T cells in the human.

In some embodiments, provided herein are compositions comprising a TNFRSF25 agonist and one or both of an interleukin (e.g., IL-2, IL-7, IL-15, or an analog thereof) and an mTOR inhibitor.

In some embodiments, provided herein are compositions comprising a TL1A fusion protein as described herein and an effective amount of IL-2.

In some embodiments, provided herein are compositions comprising an agonistic TNFRSF25 antibody as described herein and an effective amount of IL-2.

In some embodiments, provided herein are compositions comprising a small molecule agonist of TNFRSF25 as described herein and an effective amount of IL-2.

In some embodiments, provided herein are compositions comprising a TL1A fusion protein as described herein and an effective amount of an mTOR inhibitor.

In some embodiments, provided herein are compositions comprising an agonistic TNFRSF25 antibody as described herein and an effective amount of an mTOR inhibitor.

In some embodiments, provided herein are compositions comprising a small molecule agonist of TNFRSF25 as described herein and an effective amount of an mTOR inhibitor.

In some embodiments, provided herein are compositions comprising a TL1A fusion protein as described herein and an effective amount of rapamycin.

In some embodiments, provided herein are compositions comprising an agonistic TNFRSF25 antibody as described herein and an effective amount of rapamycin.

In some embodiments, provided herein are compositions comprising a small molecule agonist of TNFRSF25 as described herein and an effective amount of rapamycin.

While it is possible to use a composition disclosed herein (a composition containing a TL1A fusion protein) for therapy as is, in some embodiments it may be preferable to formulate the composition in a pharmaceutical formulation, e.g., in admixture with a suitable pharmaceutical excipient, diluent, or carrier selected with regard to the intended route of administration and standard pharmaceutical practice. Accordingly, pharmaceutical compositions or formulations containing at least one active composition disclosed herein (e.g., TL1A fusion protein, agonistic anti-TNFRSF25 antibody, small molecule agonist of TNFRSF25, etc.) in association with a pharmaceutically acceptable excipient, diluent, and/or carrier are provided herein. The excipient, diluent and/or carrier must be "acceptable" in the sense of being compatible with the other ingredients of the formulation and not deleterious to the recipient thereof.

The compositions can be formulated for administration in any convenient way for use in human or veterinary medicine. For in vivo administration to humans, the compositions disclosed herein can be formulated according to known methods used to prepare pharmaceutically useful compositions. The TNFRSF25 agonists (e.g., TL1A fusion proteins, agonistic anti-TNFRSF25 antibodies, small molecule agonist of TNFRSF25, etc.) can be combined in admixture, either as the sole active material or with other known active materials, (e.g., one or more therapies useful for combination therapy, as described below) with pharmaceutically suitable diluents (e.g., Tris-HCl, acetate, phosphate), preservatives (e.g., Thimerosal, benzyl alcohol, parabens), emulsifiers, solubilizers, adjuvants and/or carriers. Suitable carriers and their formulations are described in Remington's Pharmaceutical Sciences, 16th ed. 1980, Mack Publishing Co.

The TNFRSF25 agonists (e.g., TL1A fusion proteins, antibodies) described herein, as well as interleukins (IL-2, or an analog thereof etc.) and mTOR inhibitors (e.g., rapamycin, etc.) can be formulated together or separately as a sustained release composition. A "sustained release composition" can include any suitable vehicle that releases the TL1A fusion protein over a period of time. Non-limiting examples of sustained release compositions include microspheres (e.g., poly(DL-lactide-co-glycolide) (PLGA) microspheres), anhydrous poly-vinyl alcohol (PVA), millicylinders, alginate gels, biodegradable hydrogels, complexing agents and nanoparticles. [See, e.g., Ashton, et al. (2007) Biomaterials, 28, 36, 5518; Drury, J. L. et al. (2003) Biomaterials; 24:4337-4351; U.S. Pat. No. 7,226,617 to Ding et al.; Simmons, C. A. et al. (2004) Bone; 35:562-569; Zhu, G. et al. (2000) Nat Biotech; 18:52-57, Biodegradable Hydrogels for Drug Delivery, K. Park et al, 1993, Technomic Publishing, Trans Am Ophthalmol Soc, K. Derwent et al, 2008; 106:206-13.]

Administration and Dosage

The compositions described herein can be administered by any suitable route of administration known in the art. For example, the TNFRSF25 agonists, interleukins, and mTOR inhibitors can be formulated, together or separately, for parenteral administration (e.g., intravenous, intraperitoneal, epidural, intrathecal, intramuscular, intraluminal, intratracheal, intradermal or subcutaneous).

In an exemplary embodiment, an TL1A fusion protein, agonistic anti-TNFRSF25 antibody, or a small molecule agonist of TNFRSF25 is administered to a patient via an immunization route, e.g., intra-venously, intra-muscularly, intra-peritoneally, and the like.

For any composition or formulation used in the methods described herein, the therapeutically effective dose can be estimated initially from animal models. Dose-response curves derived from animal systems are then used to determine testing doses for the initial clinical studies in humans. In safety determinations for each composition, the dose and frequency of administration should meet or exceed those anticipated for use in the clinical studies. The data obtained from the animal studies can be used in formulating a range of doses for use in humans. The therapeutically effective doses for use in humans is preferably within a range of circulating concentrations that include the $ED_{50}$ with little or no toxicity. The dosage can vary within this range depending upon the dosage form employed and the route of administration utilized.

The compositions described herein will typically contain an effective amount of the compositions for achieving the desired effect. As used herein the terms "therapeutically effective amount" and "effective amount," used interchangeably, applied to a dose or amount refers to a quantity of a composition, compound or pharmaceutical formulation that is sufficient to result in a desired activity upon administration to an animal in need thereof. Within the context of the present disclosure, the term "therapeutically effective amount" refers to that quantity of a composition, compound or pharmaceutical formulation that is sufficient to reduce or eliminate at least one symptom of a disease or condition specified herein. When a combination of active ingredients is administered, the effective amount of the combination may or may not include amounts of each ingredient that would have been effective if administered individually. The dosage of the therapeutic formulation will vary, depending upon the nature of the disease or condition, the patient's medical history, the frequency of administration, the manner of administration, the clearance of the agent from the host, and the like. The initial dose may be larger, followed by smaller maintenance doses. The dose may be administered, e.g., weekly, biweekly, daily, semi-weekly, etc., to maintain an effective dosage level. As used herein, an "effective amount of an interleukin" (e.g., IL-2, IL-7, IL-15, or an analog thereof) is the amount that, when administered to a subject as part of a combination therapy with a TNFRSF25 agonist (e.g., an agonistic anti-TNFRSF25 antibody, a TL1A fusion protein, or a small molecule agonist of TNFRSF25 as described herein), is sufficient to achieve a synergistic effect on the expansion of Treg cells. Typically, the effective amount of IL-2 or other suitable interleukin or analog thereof used in the methods (e.g., combination therapies) disclosed herein is an amount (dose) that would induce suboptimal, or fail to induce, expansion of Treg cells if administered alone (i.e., not in a combination therapy) to a human patient. Typically, a dose of IL-2 that would induce suboptimal, or fail to induce, expansion of Treg cells in a human patient is a dose that is less than 1 million units per square meter per day (see, e.g., Koreth, J.; N Engl J. Med. 2011 Dec. 1; 365(22):2055-66; and Matsuoka, K. Sci Transl Med. 2013 Apr. 3; 5(179):179ra43). In some embodiments, IL-2 is administered to a human patient in an amount that is considered to be a "low dose" of IL-2 or a "very low dose" of IL-2. As used herein, a "low dose of IL-2" is a dose of approximately 300,000 units per square meter per day. As used herein a "very low dose of IL-2" is a dose of approximately 30,000 units per square meter per day. In some embodiments, an effective amount of IL-2 is an amount in the range of 30,000 to 300,000 units per square meter per day.

As used herein, an "effective amount of an mTOR inhibitor" (e.g., rapamycin) is the amount that, when administered to a subject as part of a combination therapy with a TNFRSF25 agonist (e.g., an agonistic anti-TNFRSF25 antibody, a TL1A fusion protein, or a small molecule agonist of TNFRSF25 as described herein), is sufficient to reduce the frequency and/or expansion of effector T cells. Typically, the effective amount of an mTOR inhibitor is an amount that inhibits the expansion and/or reduced the frequency of effector T cells in a subject, e.g., by at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 50%, at least 55%, at least 60%, at least 65%, at least 70%, at least 75%, at least 80%, at least 85%, at least 90%, at least 95%, at least 99%. In other embodiments, the amount of inhibition of effector T cells expansion and/or reduction in the frequency of effector T cells is at 2-fold, at least 3-fold, at least 4-fold, at least 5-fold, at least 10-fold, or more. Therapeutically effective dosages can be determined stepwise by combinations of approaches such as (i) characterization of effective doses of the composition or compound in in vitro cell culture assays using, e.g., T regulatory cell proliferation as a read-out (ii) characterization in animal studies using T regulatory cell proliferation and/or animal survival and/or improvement in the modeled condition (e.g., IBD, asthma, etc.) as a readout, followed by (iii) characterization in human trials using improvement in condition (e.g., disease or disorder, e.g., autoimmune disease, asthma, graft-versus host disease, chronic infection, inflammation, etc.) and/or enhanced survival rates as a readout.

The appropriate dose and dosage times under certain conditions can be determined by the test based on the above-described indices but may be refined and ultimately decided according to the judgment of the practitioner and each patient's circumstances (age, general condition, severity of symptoms, sex, etc.) according to standard clinical techniques.

Typical dosages of a TL1A fusion protein in a composition described herein range from about 0.001-100 milligram per kilogram body weight per day (mg/kg/day), from about 0.001-50 mg/kg/day, from about 0.0025-40 mg/kg/day, from about 0.005-30 mg/kg/day, from about 0.01-25 mg/kg/day, from about 0.025-20 mg/kg/day, from about 0.05-15 mg/kg/day, from about 0.05-10 mg/kg/day, 0.05-5 mg/kg/day, or from about 1-2 mg/kg/day.

Typical dosages of an agonistic anti-TNFRSF25 antibody per day are between about 0.05 mg/kg and 10 mg/kg, between about 0.1 mg/kg and 8 mg/kg, between about 0.2 mg/kg and about 5 mg/kg, or between about 0.4 mg/kg and about 4 mg/kg. In some embodiments, a typical dosage of the agonistic anti-TNFRSF25 antibody is about 0.4 mg/kg, about 0.5 mg/kg, about 1 mg/kg, about 1.5 mg/kg, about 2 mg/kg, about 2.5 mg/kg, about 3 mg/kg, about 3.5 mg/kg, about 4 mg/kg, etc.

Typical dosages of IL-2 or other cytokine (e.g., IL-7, IL-15) for use in a combination therapy disclosed herein, e.g., a combination therapy with a TNFRSF25 agonist (e.g., TL1A fusion protein, agonistic anti-TNFRSF25 antibody, etc.) is a dosage between about 10,000 and 1,000,000 units per square meter per day, between about 15,000 and 900,000 units per square meter per day, between about 20,000 and 800,000 units per square meter per day, between about 25,000 and 700,000 units per square meter per day, between about 30,000 and 500,000 units per square meter per day, between about 30,000 and 400,000 units per square meter per day, or between about 30,000 and 300,000 units per square meter per day.

Typical dosages of rapamycin per day are between about 25 μg/kg and about 500 μg/kg, between about 50 μg/kg and about 400 μg/kg, or between about 75 μg/kg and about 300 μg/kg.

A TNFRSF25 agonist described herein (e.g., a TL1A fusion protein, an agonistic anti-TNFRSF25 antibody, a small molecule inhibitor of TNFRSF25, etc.), and/or one or more compositions comprising one or more TNFRSF25 agonists and/or comprising an interleukin (e.g., IL-2, IL-7, IL-15) can be administered to a subject in one or more dosages sufficient to increase proliferation of Treg cells in the subject by at least about 2-fold, at least about 3-fold, at least about 5-fold, at least about 10-fold, or more. According to the present invention, IL-2 and a TNFRSF25 agonist are administered in amounts that together result in a synergistic effect on the expansion of Treg cells. Methods for measuring Treg cell proliferation are known in the art. For example, for monitoring Treg proliferation in vivo, peripheral blood cells can be collected from treated subjects, stained (e.g., immunostaining) for cell markers including CD4, CD25, IL7R and FoxP3, and analyzed by flow cytometry. Numbers of circulating FoxP3 Treg cells can be quantified and compared to starting numbers (e.g., before treatment).

Further, in some embodiments, an effective amount of an mTOR inhibitor (e.g., rapamycin) is administered to a subject in one or more dosages sufficient to inhibit effector T cells expansion and/or to decrease the frequency of effector T cells in the subject by at least 5%, at least 10%, at least 20%, at least 25%, at least 30%, at least 40%, at least 50%, at least 60%, at least 70%, at least 75%, at least 80%, at least 85%, at least 90%, at least 95%, or at least 99%. In some embodiments, the amount of inhibition of effector T cells expansion and/or the reduction in the effector T cell frequency is at 2-fold, at least 3-fold, at least 4-fold, at least 5-fold, at least 10-fold, or more.

Methods for measuring the frequency and/or expansion (e.g., proliferation) of effector T cells are known in the art. For example, for monitoring CD4 and/or CD8 T cell proliferation in vivo, peripheral blood cells can be collected from treated subjects, stained (e.g., immunostaining) for cell markers including CD4, CD25, FoxP3, Ki67, and other suitable cell markers of proliferation, and analyzed by flow cytometry. Numbers and frequencies of circulating T effector cells can be quantified and compared to starting numbers (e.g., before treatment).

Uses of TL1A Fusion Proteins and Other TNFRSF25 Agonists

Described herein are methods of modulating an antigen-specific immune response in a human patient in need thereof. In some embodiments, the method can include administering to the patient a composition comprising a TL1A fusion protein described herein. Typically, the composition comprising the TL1A fusion protein contains a therapeutically effective amount of the TL1A fusion protein. In a specific embodiment, the antigen-specific immune response is inhibited.

In some embodiments, an antigen-specific immune response is determined to be modulated if the immune response against the antigen, as measured by any suitable measure (e.g., frequency of antigen-specific antibodies, T cells, B cells, antigen-specific T cell proliferation, etc.) is increased or decreased by at least 5%, at least 10%, at least 20%, at least 25%, at least 30%, at least 40%, at least 50%, at least 60%, at least 70%, at least 75%, at least 80%, at least 85%, at least 90%, at least 95%, or at least 99%. In other embodiments, an antigen-specific immune response is determined to be modulated if the immune response against the antigen, as measured by any suitable measure (e.g., frequency of antigen-specific antibodies, T cells, B cells, antigen-specific T cell proliferation, etc.) is increased or decreased by at 2-fold, at least 3-fold, at least 4-fold, at least 5-fold, at least 10-fold, or more. Also described herein are methods of treating a disease or disorder associated with an antigen-specific immune response, or treating one or more symptoms of the disease or disorder, in a human patient in need thereof The methods can include administering to the patient a composition comprising a TL1A fusion protein as described herein. Typically, the composition comprising the TL1A fusion protein contains a therapeutically effective amount of the TL1A fusion protein.

Also described herein are methods of reducing the severity and/or frequency of one or more adverse events associated with and/or caused by the administration of a TNFRSF25 agonist to a subject (e.g., patient). In some embodiments, the method of reducing the severity and/or frequency of one or more adverse events comprises administering to a human patient in need thereof a composition comprising a TL1A fusion protein as described herein in a physiologically acceptable carrier. In some embodiments, an adverse event that is reduced or inhibited is one or more symptoms of inflammatory bowel disease, development of inflammatory bowel disease, weight loss, rash, diarrhea, myalgias, decreased platelet counts, elevated liver enzyme levels, and death.

Also provided herein are methods of modulating an antigen-specific immune response, and/or for treating a disease or disorder associated with an antigen-specific immune response, and/or for treating one or more symptoms of the disease or disorder, in a human patient in need thereof, comprising administering a combination therapy comprising a TNFRSF2 agonist and an interleukin (e.g., an effective amount of an interleukin, e.g., IL-2) to a subject (patient) in need thereof. Also provided herein are methods of modulating an antigen-specific immune response, and/or for treating a disease or disorder associated with an antigen-specific immune response, and/or for treating one or more symptoms of the disease or disorder, in a human patient in need thereof, comprising administering a combination therapy comprising a TNFRSF25 agonist and an mTOR inhibitor (e.g., rapamycin) to a subject (patient) in need thereof. Also provided herein are methods of modulating an antigen-specific immune response, and/or for treating a disease or disorder associated with an antigen-specific immune response, and/or for treating one or more symptoms of the disease or disorder, in a human patient in need thereof, comprising administering a combination therapy comprising a TNFRSF25 agonist and an interleukin (e.g., an effective amount of an interleukin (e.g., IL-2, IL-7, IL-15, or an analog thereof)) and an mTOR inhibitor (e.g., rapamycin) to a subject (patient) in need thereof.

Exemplary effective amounts of TNFRSF25 agonists, interleukins, and mTOR inhibitors for use in the methods disclosed herein are described above.

In any of the above-described methods, a patient in need of treatment can be, for example and without limitation, a patient undergoing or about to undergo induction therapy in preparation for a solid organ or stem cell transplant, a patient who is a solid organ or stem cell transplant recipient and is undergoing or is about to undergo maintenance therapy, a patient who is a solid organ or stem cell transplant recipient, an allergic patient; a patient who is receiving or about to receive a vaccine, or a patient being treated or about to be treated with an immune checkpoint inhibitor (e.g., CTLA-4 or PD-1 inhibitor).

In any of the above methods, the disease or disorder that can be treated can be an autoimmune disease or disorder (e.g., inflammatory bowel disease, rheumatoid arthritis), transplant rejection, graft-versus-host disease, inflammation, asthma, allergies, and chronic infection.

In some embodiments the above methods reduce an antigen-specific immune response in the patient by at least 5%, at least 10%, at least 15%, at least 20%, at least 25%, at least 30%, at least 35%, at least 40%, at least 50%, at least 55%, at least 60%, at least 65%, at least 70%, at least 75%, at least 80%, at least 85%, at least 90%, at least 95%, at least 99%. In other embodiments, the antigen-specific immune response is reduced by at least 2-fold, at least 3-fold, at least 4-fold, at least 5-fold, at least 10-fold, or more.

In some embodiments, the above-described methods result in significantly increased proliferation of Treg cells in a patient following administration of a composition (e.g., comprising a TL1A fusion protein) or combination therapy (e.g., administration of a TNFRSF25 agonist and IL-2 and/or an mTOR inhibitor) described herein. For example in some embodiments, the methods described herein result in increased proliferation of Treg cells by at least 2-fold, at least 3-fold, at least 4-fold, at least 5-fold, or at least 10-fold or more, in the patient following administration of the method.

In any of the above embodiments, the methods can comprise one or multiple administrations of one or more of the compositions to be administered to the patient. For example, when a subject (e.g., patient) is to be administered a composition comprising a TL1A fusion protein, the method can comprise a single administration or more. Exemplary dosing regimens are described above. When a TNFRSF25 agonist is administered in a combination therapy with an interleukin (e.g., IL-2, IL-7, IL-15) and/or an mTOR inhibitor (e.g., rapamycin), the TNFRSF25 agonist can be administered on the same or a different day than the interleukin and/or mTOR inhibitor. Each active agent can be administered in a separate composition or two or more active agents can be administered in combination.

As described above, in some embodiments, the methods described herein are useful for treating autoimmune diseases, alloimmune responses, or any other disease, disorder or condition that involves a T cell response (e.g., in a patient in need thereof). Generally, these are conditions in which the immune system of an individual (e.g., activated T cells) attacks the individual's own tissues and cells, or implanted tissues, cells, or molecules (as in a graft or transplant). Non-limiting examples of diseases and disorders that can be treated according to the methods described herein, include, e.g., autoimmune disease or disorder (e.g., IBD and rheumatoid arthritis), transplant rejection, graft-versus-host disease (GVHD), inflammation, asthma, allergies, and chronic infection.

For transplant rejection and GVHD associated disorders, a patient in need of treatment can be a patient who is undergoing or about to undergo induction therapy in preparation for a solid organ or stem cell transplant, a patient who is a solid organ or stem cell transplant recipient and is undergoing or is about to undergo maintenance therapy, a patient who is a solid organ or stem cell transplant recipient (and the therapy, e.g., TL1A fusion protein or combination therapy comprising administration of a TNFRSF25 agonist and an interleukin (e.g., IL-2, IL-7, IL-15, or an analog thereof) and/or an mTOR inhibitor (e.g., rapamycin), is administered in order to facilitate early withdrawal of maintenance immunosuppressive therapy), an allergic patient (and the therapy, e.g., TL1A fusion protein or combination therapy comprising administration of a TNFRSF25 agonist and an interleukin (e.g., IL-2, IL-7, IL-15) and/or an mTOR inhibitor (e.g., rapamycin), is administered to reduce symptoms of a specific allergic reaction); a patient who is receiving or about to receive a vaccine (and the therapy, e.g., TL1A fusion protein or combination therapy comprising administration of a TNFRSF25 agonist and an interleukin (e.g., IL-2, IL-7, IL-15, or an analog thereof) and/or an mTOR inhibitor (e.g., rapamycin), is administered in order to enhance antigen-specific T cell responses stimulated by the vaccine or in order to enhance T cell memory immune responses), or a patient being treated or about to be treated with an immune checkpoint inhibitor (e.g., CTLA-4 or PD-1 inhibitor) (and the therapy, e.g., TL1A fusion protein or combination therapy comprising administration of a TNFRSF25 agonist and an interleukin (e.g., IL-2, IL-7, IL-15, or an analog thereof) and/or an mTOR inhibitor (e.g., rapamycin), is administered in order to enhance T cell immune responses).

Exemplary autoimmune diseases that can be treated with the methods of the present disclosure include, e.g., type I diabetes, multiple sclerosis, thyroiditis (such as Hashimoto's thyroiditis and Ord's thyroiditis), Grave's disease, systemic lupus erythematosus, scleroderma, psoriasis, arthritis, rheumatoid arthritis, alopecia greata, ankylosing spondylitis, autoimmune hemolytic anemia, autoimmune hepatitis, Behcet's disease, Crohn's disease, dermatomyositis, glomerulonephritis, Guillain-Barre syndrome, IBD, lupus nephritis, myasthenia gravis, myocarditis, pemphigus/pemphigoid, pernicious anemia, polyarteritis nodosa, polymyositis, primary biliary cirrhosis, rheumatic fever, sarcoidosis, Sjogren's syndrome, ulcerative colitis, uveitis, vitiligo, and Wegener's granulomatosis.

Exemplary alloimmune responses that can be treated with the methods of the present disclosure include GVHD and transplant rejection. Thus, for example, the fusion proteins disclosed herein can be administered as an "induction therapy" in preparation for a solid organ or stem cell transplant, or as "maintenance therapy" in solid organ or stem cell transplant recipients, and can also be administered to a solid organ or stem cell transplant recipient in order to facilitate early withdrawal of maintenance immunosuppressive therapy.

The methods described herein, e.g., comprising administration of a TL1A fusion protein or combination therapy comprising administration of a TNFRSF25 agonist and an interleukin (e.g., IL-2, IL-7, IL-15, or an analog thereof) and/or an mTOR inhibitor (e.g., rapamycin) can also be administered to an allergic patient to reduce one or more symptoms of a specific allergic reaction. Examples of allergic reaction include, e.g., allergic asthma, nut (e.g., peanut) allergy, celiac disease (wheat gluten) allergy, tolerization protocol for drug allergy (e.g., penicillins, sulfonamides). Many substances can act as allergens; however, some substances are very common allergens, such as, pollen and mold, dust mite droppings, pet allergens, various foods, insect stings, and cockroach antigens.

The compositions and combination therapies described herein can also be administered to a patient in conjunction with a vaccine in order to enhance antigen specific T cell responses stimulated by the vaccine. As described above, the TL1A fusion proteins described herein can enhance antigen-specific immune responses by having an effect on T effector cell co-stimulation.

The TL1A fusion proteins and the combination therapies comprising the administration of a TNFRSF25 agonist and the administration of an interleukin (e.g., IL-2, IL-7, IL-15, or an analog thereof) and/or an mTOR inhibitor (e.g., rapamycin) described herein can also be administered to a patient in conjunction with a vaccine in order to enhance T cell memory immune responses, or in conjunction with an immune checkpoint inhibitor (e.g., CTLA-4 or PD-1 inhibitor) in order to enhance T cell immune responses. As described above, the TL1A fusion proteins and the combination therapies comprising the administration of a TNFRSF25 agonist and the administration of an interleukin (e.g., IL-2, IL-7, IL-15, or an analog thereof) and/or an mTOR inhibitor (e.g., rapamycin) described herein can enhance antigen-specific immune responses by having an effect on T effector cell costimulation.

Also contemplated herein are combination therapies comprising the administration of a TL1A fusion protein and/or another TNFRSF25 agonist and an anti-inflammatory and/or immunosuppressive antibody or other anti-inflammatory or immunosuppressive agent. By way of example, in some embodiments, a TL1A fusion protein or other TNFRSF25 agonist described herein can be administered to a subject in an induction therapy in preparation for a solid organ or stem cell transplant, or as maintenance therapy in solid organ or stem cell transplant recipients, and can be administered to a solid organ or stem cell transplant recipient in order to facilitate early withdrawal of maintenance immunosuppressive therapy. In some embodiments it may be advantageous to coadminister the TL1A fusion protein in a combination therapy with agents such as rapamycin, tacrolimus, other mTOR inhibitors, MEK inhibitors, CTLA4-Ig molecules, CD80 or CD86 blocking antibodies or molecules, CD40 or CD40L blocking antibodies or molecules, PTEN blocking molecules, OX40 or OX40L blocking antibodies or molecules, prednisone, methylprednisone, fluticasone or combinations thereof. Alternatively, or in addition, the TL1A fusion protein or other TNFRSF25 agonist can be administered with an interleukin (e.g., a low dose or very low dose of IL-2 as described in the Examples below).

As another example, in some embodiments, a TL1A fusion protein or other TNFRSF25 agonist described herein can be administered to a subject patient to reduce one or more symptoms of a specific allergic reaction (e.g., asthma, celiac disease, drug allergies). It may be advantageous to coadminister the TL1A fusion protein or other TNFRSF25 agonist in a combination therapy with rapamycin, tacrolimus, other mTOR inhibitors, CTLA4-Ig molecules, CD80 or CD86 blocking antibodies or molecules, CD40 or CD40L blocking antibodies or molecules, PTEN blocking molecules, OX40 or OX40L blocking antibodies or molecules, prednisone, methylprednisone, fluticasone or calcineurin inhibitors. Alternatively, or in addition, the TL1A fusion protein or other TNFRSF25 agonist can be administered with an interleukin (e.g., a low dose or very low dose of IL-2, as described in the Examples below).

Furthermore, as discussed above, it is presently discovered that the TL1A fusion proteins disclosed herein safely and selectively stimulate the proliferation of cognate T regulatory cells (Treg) in vivo. In particular, in contrast to certain previously described attempts at modulating immune responses with TNFRSF25 modulating agents, it is presently demonstrated in studies in humanized mice and primates, that treatment with the TL1A fusion proteins described herein did not induce weight loss, cause changes in white blood cell count, or lead to any other dangerous or unwanted side effects, indicating that the TL1A fusion proteins could be safely administered in vivo, including to primates. The studies thus also demonstrated that the TL1A fusion proteins are expected to be safely administered to human patients. Thus, in conjunction with these discoveries, also contemplated herein are methods of reducing an adverse event associated with a therapy that includes the administration of a TNFRSF25 agonist in a human patient. The methods include administering to a patient in need thereof a TL1A fusion protein-containing composition described herein in a physiologically acceptable carrier. For example, the adverse event can be development of one or more symptoms of inflammatory bowel disease. The adverse event can also be weight loss, rash, diarrhea, myalgias, decreased platelet counts, elevated liver enzyme levels, and/or death.

In accordance with the present disclosure, there may be employed conventional molecular biology, microbiology, recombinant DNA, immunology, cell biology and other related techniques within the skill of the art. See, e.g., Sambrook et al., (2001) Molecular Cloning: A Laboratory Manual. 3rd ed. Cold Spring Harbor Laboratory Press: Cold Spring Harbor, N.Y.; Sambrook et al., (1989) Molecular Cloning: A Laboratory Manual. 2nd ed. Cold Spring Harbor Laboratory Press: Cold Spring Harbor, N.Y.; Ausubel et al., eds. (2005) Current Protocols in Molecular Biology. John Wiley and Sons, Inc.: Hoboken, N.J.; Bonifacino et al., eds. (2005) Current Protocols in Cell Biology. John Wiley and Sons, Inc.: Hoboken, N.J.; Coligan et al., eds. (2005) Current Protocols in Immunology, John Wiley and Sons, Inc.: Hoboken, N.J.; Coico et al., eds. (2005) Current Protocols in Microbiology, John Wiley and Sons, Inc.: Hoboken, N.J.; Coligan et al., eds. (2005) Current Protocols in Protein Science, John Wiley and Sons, Inc.: Hoboken, N.J.; Enna et al., eds. (2005) Current Protocols in Pharmacology John Wiley and Sons, Inc.: Hoboken, N.J.; Hames et al., eds. (1999) Protein Expression: A Practical Approach. Oxford University Press: Oxford; Freshney (2000) Culture of Animal Cells: A Manual of Basic Technique. 4th ed. Wiley-Liss; among others. The Current Protocols listed above are updated several times every year.

EXAMPLES

Example 1

Materials and Methods

The following are the materials and methods used in the Examples set forth below.

Mice and Adoptive Transfer Model

Foxp3+RFP+ (FIR mice) and Foxp3+GFP+ reporter mice on a B6 background (generously provided by Dr. Richard Flavell and Dr. Alexander Rudensky [see, Wan, Y. Y., and R. A. Flavell. 2005. Identifying Foxp3-expressing suppressor T cells with a bicistronic reporter. Proc. Natl. Acad. Sci. USA 102: 5126-5131]), CD4−/− mice, NOD.SCID/yc−/− (NSG), OT-II and OT-II/FIR mice were bred in an animal facility. Mice were used at 6-12 weeks of age and were maintained in pathogen-free conditions. Treg adoptive transfer models were established as previously reported (see, Schreiber et al. Oncoimmunology. 2012 Aug. 1; 1(5):642-648).

Cloning of Rhesus Macaque and Human TL1A-Ig

Total RNA was isolated from preparations of rhesus macaque peripheral blood mononuclear cells using RNeasy kits (Qiagen). A rhesus macaque cDNA library was then generated by PCR amplification of 5' capped and 3' poly-A tailed RNA using 5'RACE (Invitrogen). The extracellular domain of rhesus macaque TL1A (amino acids 73-252) were amplified using the following primers: forward 5'-AAAGGACAGGAGTTTGCACC-3' (SEQ ID NO: 17), reverse 5'-CTATAGTAAGAAGGCTCCAAA-3' (SEQ ID NO: 18), and fused to the hinge-CH2-CH3 domain of rhesus macaque IgG1, which was amplified using the following primers: forward 5'-ATAAAAACATGTGGTGGTGG-3' (SEQ ID NO; 19), and reverse 5'-CTGCGTGTAGTGGTTGTGCA-3' (SEQ ID NO: 20), in cloned into the second multiple cloning site of the mammalian expression vector pVITRO2-hygro-mcs (Invivogen).

For the human TL1A-Ig, a human cDNA library was generated by PCR amplification of 5' capped and 3' poly-A tailed RNA using 5'RACE (Invitrogen). The extracellular domain of human TL1A (amino acids 60-251) was amplified and fused to the hinge-$CH_2$—CH3 domain of human IgG1, and cloned into the pVITRO2-hygro (InvivoGen, San Diego, Calif.).

The nucleic acid and amino acid sequences of the TL1A portion of the rhesus macaque fusion protein were as follows:

```
Nucleic Acid Sequence:
                                                (SEQ ID NO: 5)
aaaggacaggagtttgcaccttcacatcagcaagtttatgcacctcttag

agcagacggagataagccaagggcacacctgacagttgtgacacaaactc

ccacacagcactttaaaaatcagttcccagctctgcactgggaacatgaa

ctaggcctggccttcaccaagaaccgaatgaactataccaacaaattcct

gctgatcccagagtcgggagactacttcatttactcccaggtcacattcc

gtgggatgacctctgagtgcagtgaaatcagacaagcaggccgaccaaac

aagccagactccatcactgtggtcatcaccaaggtaacagacagctaccc

tgagccaacccagctcctcatggggaccaagtctgtgtgcgaagtaggta

gcaactggttccagcccatctacctcggacccatgttctccttgcaagaa

ggggacaagctaatggtgaacgtcagtgacatctccttggtggattacac

aaaagaagataaaaccttctttggagccttcttactatag;
and

Amino Acid Sequence
                                                (SEQ ID NO: 6)
kgqefapshqqvyaplradgdkprahltvvtqtptqhfknqfpalhwehe

lglaftknrmnytnkfllipesgdyfiysqvtfrgmtsecseirpgrpnk

pdsitvvitkvtdsypeptqllmgtksvcevgsnwfqpiylgpmfslqeg

dklmvnvedislvdytkedktffgafll.
```

The nucleic acid and amino acid sequences of the rhesus macaque IgG1 hinge-CH2-CH3 sequence were as follows:

```
Nucleic Acid Sequence:
                                                (SEQ ID NO: 7)
ataaaaacatgtggtggtggcagcaaacctcccacgtgcccaccgtgccc

agcacctgaactcctgggggggaccgtcagtcttcctcttccccccaaaac

ccaaggacaccctcatgatctcccggacccctgaggtcacatgcgtggtg

gtagacgtgagccaggaagaccccgatgtcaagttcaactggtacgtaaa

cggcgcggaggtgcatcatgcccagacgaagccacgggagacgcagtaca

acagcacatatcgtgtggtcagcgtcctcaccgtcacgcaccaggactgg

ctgaacggcaaggagtacacgtgcaaggtctccaacaaagccctcccggt

ccccatccagaaaaccatctccaaagacaaagggcagccccgagagcctc

aggtgtacaccctgcccccgtcccgggaggagctgaccaagaaccaggtc

agcctgacctgcctggtcaaaggcttctaccccagcgacatcgtcgtgga

gtgggagaacagcgggcagccggagaacacctacaagaccaccccgcccg

tgctggactccgacggctcctacttcctctacagcaagctcaccgtggac

aagagcaggtggcagcaggggaacgtcttctcatgctccgtgatgcatga

ggctctgcacaaccactacacgcag;
and

Amino Acid Sequence:
                                                (SEQ ID NO: 8)
iktcgggskpptcppcpapellggpsvflfppkpkdtlmisrtpevtcvv

vdvsqedpdvkfnwyvngaevhhaqtkpretqynstyrvvsyltythqdw
```

-continued lngkeytekvsnkalpvpigktiskdkgqprepqvytlppereeltknqv sltelvkgfypsdivvewensggpentykttppvldsdgsyflyskltvd kerwqqgnvfscsvmhealhnhytg.

The nucleic acid and amino acid sequences of the complete rhesus macaque TL1A-Ig fusion protein were:

DNA Sequence:

(SEQ ID NO: 9)

atggagacagacacactcctgctatgggtactgctgctctgggttccagg ttccactggtgacctcgagataaaaacatgtggtggtggcagcaaacctc ccacgtgcccaccgtgcccagcacctgaactcctgggggggaccgtcagtc ttcctcttccccccaaaacccaaggacaccctcatgatctcccggacccc tgaggtcacatgcgtggtggtagacgtgagccaggaagaccccgatgtca agttcaactggtacgtaaacggcgcggaggtgcatcatgcccagacgaag ccacgggagacgcagtacaacagcacatatcgtgtggtcagcgtcctcac cgtcacgcaccaggactggctgaacggcaaggagtacacgtgcaaggtct ccaacaaagccctcccggtccccatccagaaaaccatctccaaagacaaa gggcagccccgagagcctcaggtgtacaccctgcccccgtcccgggagga gctgaccaagaaccaggtcagcctgacctgcctggtcaaaggcttctacc ccagcgacatcgtcgtggagtgggagaacagcgggcagccggagaacacc tacaagaccaccccgcccgtgctggactccgacggctcctacttcctcta cagcaagctcaccgtggacaagagcaggtggcagcaggggaacgtcttct catgctccgtgatgcatgaggctctgcacaaccactacacgcaggaattc aaaggacaggagtttgcaccttcacatcagcaagtttatgcacctcttag agcagacggagataagccaagggcacacctgacagttgtgacacaaactc ccacacagcactttaaaaatcagtteccagctctgcactgagaacatgaa ctaggcctggccttcaccaagaaccgaatgaactataccaacaaattcct gctgatcccagagtcgggagactacttcatttactcccaggtcacattcc gtgggatgacctctgagtgcagtgaaatcagacaagcaggccgaccaaac aagccagactccatcactgtggtcatcaccaaggtaacagacagctaccc tgagccaacccagctcctcatggggaccaagtctgtgtgcgaagtaggta gcaactggttccagcccatctacctcggacccatgttctccttgcaagaa ggggacaagctaatggtgaacgtcagtgacatctccttggtggattacac aaaagaagataaaaccttctttggagccttcttactatag;

and

Amino Acid Sequence:

(SEQ ID NO: 10)

metdtlllwvlllwvpgstgdleiktcgggskpptcppcpapellggps vflfppkpkdtlmisrtpevtcyvvdvsgedpdvkfnwyvngaevhhagt kpretqynstyrvvsyltvthqdwlngkeytckvsnkalpvpiqktiskd kgqprepgvytlppereeltkngveltclvkgfypsdivvewensggpen tykttppvldsdgsyflyskltvdksrwqqgnvfscsvmhealhnhytqef kgqefapshqqvyaplradgdkprahltvvtqtptqhfknqfpalhwe helqlaftknrmnytnkfllipesgdyfiysqvtfrgmtsecseirqaqr -continued pnkpdsitvvitkvtdsypeptqllmgtksvcevgsnwfqpiylgpmfsl qegdklmvnvsdislvdytkedktffgafll.

In each of the above complete fusion protein sequences (DNA and amino acid), the italicized and underlined residues correspond to the mouse kappa leader sequence; the bold and italicized text corresponds to restriction enzyme cloning sites; the plain text corresponds to the rhesus macaque IgG1 hinge-CH2-CH3 sequence; and the underlined text corresponds to rhesus macaque TL1A extracellular domain sequence. The nucleic acid and amino acid sequences of the TL1A portion of the human TL1A-Ig fusion protein were as follows:

Nucleic Acid Sequence:

(SEQ ID NO: 11)

cgggcccagggagaggcctgtgtgcagttccaggctctaaaaggacagga gtttgcaccttcacatcagcaagtttatgcacctcttagagcagacggag ataagccaagggcacacctgacagttgtgagacaaactcccacacagcac tttaaaaatcagttcccagctctgcactgggaacatgaactaggcctggc cttcaccaagaaccgaatgaactataccaacaaattcctgctgatcccag agtcgggagactacttcatttactcccaggtcacattccgtgggatgacc tctgagtgcagtgaaatcagacaagcaggccgaccaaacaagccagactc catcactgtggtcatcaccaaggtaacagacagctaccctgagccaaccc agctcctcatggggaccaagtctgtgtgcgaagtaggtagcaactggttc cagcccatctacctcggagccatgttctccttgcaagaaggggacaagct aatggtgaacgtcagtgacatctctttggtggattacacaaaagaagata aaaccttctttggagccttcttactatag;

and

Amino Acid Sequence:

(SEQ ID NO: 12)

raqgeacvqfgalkgqefapshqqvyaplradgdkprahltvvrqtptqh fknqfpalhwehelglaftknrmnytnkfllipesgdyfiysqvtfrgmt secseirqagrpnkpdsitvvitkvtdsypeptqllmgtksvcevgsnwf qpiylgamfslqegdklmvnvsdislvdytkedktffgafll.

The nucleic acid and amino acid sequences of the human IgG1 hinge-CH2-CH3 sequence were as follows:

Nucleic Acid Sequence:

(SEQ ID NO: 13)

tgtgacaaaactcacacatgcccaccgtgcccagcacctgaactcctggg gggaccgtcagtcttcctcttccccccaaaacccaaggacaccctcatga tctcccggacccctgaggtcacatgcgtggtggtggacgtgagccacgaa gaccctgaggtcaagttcaactggtacgtggacggcgtggaggtgcataa tgccaagacaaagccgcgggaggagcagtacaacagcacgtaccgtgtgg tcagcgtcctcaccgtcctgcaccaggactggctgaatggcaaggagtac aagtgcaaggtctccaacaaagccctcccagcccccatcgagaaaaccat ctccaaagccaaagggcagccccgagaaccacaggtgtacaccctgcccc catcccgggatgagctgaccaagaaccaggtcagcctgacctgcctggtc -continued aaaggcttctatcccagcgacatcgccgtggagtgggagagcaatgggca gccggagaacaactacaagaccacgcctcccgtgctggactccgacggct ccttcttcctctacagcaagctcaccgtggacaagagcaggtggcagcag gggaacgtatctcatgctccgtgatgcatgaggctctgcacaaccactac acgcagaagagcctctccctgtctccgggtaaa;

and

Amino Acid Sequence:

(SEQ ID NO: 14)

cdkthtcppcpapellggpsvflfppkpkdtlmisrtpevtcvvvdvshe dpevkfnwyvdgvevhnaktkpreeqynstyrvvsyltvlhqdwlngkey kckvsnkalpapiektiskakgqprepqvytlppsrdeltknqvsltclv kgfypsdiavewesngqpennykttppvldsdgsfflyskltvdkerwqq gnvfscsvmhealhnhytqkslslspgk.

The nucleic acid and amino acid sequences of the complete hTL1A-Ig fusion protein were as follows:

Nucleic Acid Sequence (SEQ ID NO: 15)

tgtgacaaaactcacacatgcccaccgtgcccagcacctgaactcctggg gggaccgtcagtcttcctcttcccccccaaaacccaaggacaccctcatga tctcccggacccctgaggtcacatgcgtggtggtggacgtgagccacgaa gaccctgaggtcaagttcaactggtacgtggacggcgtggaggtgcataa tgccaagacaaagccgcgggaggagcagtacaacagcacgtaccgtgtgg tcagcgtcctcaccgtcctgcaccaggactggctgaatggcaaggagtac aagtgcaaggtctccaacaaagccctcccagcccccatcgagaaaaccat ctccaaagccaaagggcagccccgagaaccacaggtgtacaccctgcccc catcccgggatgagctgaccaagaaccaggtcagcctgacctgcctggtc aaaggcttctatcccagcgacatcgccgtggagtgggagagcaatgggca gccggagaacaactacaagaccacgcctcccgtgctggactccgacggct ccttcttcctctacagcaagctcaccgtggacaagagcaggtggcagcag gggaacgtcttctcatgctccgtgatgcatgaggctctgcacaaccacta cacgcagaagagcctctccctgtctccgggtaaa*gaattc*cgggcccagg gagaggcctgtgtgcagttccaggctctaaaaggacaggagtttgcacct tcacatcagcaagtttatgcacctettagagcagacggagataagccaag ggcacacctgacagttgtgagacaaactcccacacagcactttaaaaatc agtteccagctctgcactgggaacatgaactaggcctggccttcaccaag aaccgaatgaactataccaacaaattcctgctgatcccagagtcgggaga ctacttcatttactcccaggtcacattccgtgggatgacctctgagtgca gtgaaatcagacaagcaggccgaccaaacaagccagactccatcactgtg gtcatcaccaaggtaacagacagctaccctgagccaacccagctcctcat ggggaccaagtctgtgtgcgaagtaggtagcaactggttccagcccatct acctcggagccatgttctecttgcaagaaggggacaagctaatggtgaac gtcagtgacatctctttggtggattacacaaaagaagataaaaccttctt tggagccttcttactatag;

and

Amino Acid Sequence (SEQ ID NO: 16)

cdkthtcppcpapellggpsvflfppkpkdtlmisrtpevtcvvvdvshe dpevkfnwyvdgvevhnaktkpreeqynstyrvvsvltvlhqdwlngkey kckvsnkalpapiektiskakgqprepqvytlppsrdeltknqvsltclv kgfypsdiavewesngqpennykttppvldsdgsfflyskltvdkerwqq gnvfscsvmhealhnhytqkslslspgk*ef*raqqeacvqfqalkqqefap shqqvyaplradqdkprahltvvrgtptghfknqfpalhwehelglaftk nrmnytnkfllipesqdyfiysqvtfrqmtsecseirqagrpnkpdsitv vitkvtdsypeptqllmqtksvcevqsnwfqpiylqamfslqegdklmvn vsdislvdytkedktffgafll.

In each of the above complete fusion protein sequences (human nucleic acid and amino acid sequences), the bold and italicized residues correspond to the restriction enzyme cloning site, the residues occurring before the restriction enzyme cloning site (plain text) correspond to the human IgG1 hinge-CH2-CH3 sequence, and the residues following the restriction enzyme cloning site (underlined text) correspond to the human TL1A extracellular domain sequence.

A murine TL1A-Ig fusion protein was also constructed. The method for its construction, and the functional characterization of the murine fusion protein are described in detail in Khan, S. Q., et al. (2013) "Cloning, expression, and functional characterization of TL1A-Ig. J Immunol 190: 1540-1550," the content of which is herein incorporated by reference in its entirety.

Cell Culture

Transfections of NIH—CHO cells were performed using standard electroporation and lipid-based transfection methods. Transfected cells were selected with an appropriate antibiotic (hygromycin) and further selected by limiting dilution single-cell cloning techniques to identify high-titer producing clones. Selected clones were then weaned off of serum and adapted to grow in serum-free conditions. The stable clone, growing in serum free media, was then loaded into a hollow-fiber cartridge system for fusion protein manufacturing. NIH—CHO-hTL1A-Ig cells were maintained in OPTI-CHO media and cell culture supernatants containing hTL1A-Ig were collected. Purification of hTL1A-Ig was performed by binding to a Protein A or Protein G column using standard methods and eluted from the column using a basic elution buffer to maintain appropriate functionality of the fusion protein. Elution with a basic buffer was essential, as elution with acidic buffers destroyed functional activity. Following elution, the protein fractions were pooled and quantitated using both standard protein assays (Bradford) and specific ELISA assays for detection of the IgG tail. Purified protein was then dialyzed to PBS and stored at −80 degrees C.

Reagents, antibodies and flow cytometry

Commercial antibodies for use in flow cytometry, ELISA and in vivo studies were purchased from BD Pharmingen, eBioscience or BioLegend. The Armenian Hamster IgG Isotype control was bought from eBioscience. Armenian hamster hybridomas producing antibodies to mouse TNFRSF25 (4C12, agonistic) were generated as described in Fang, et al. 2008. Essential role of TNF receptor superfamily 25 (TNFRSF25) in the development of allergic lung inflammation. J Exp Med 205:1037-1048. Briefly, 4C12, hTL1A-Ig and rmTL1A-Ig were produced in hollow fiber bioreactors (Fibercell Systems, Frederick, Md.) and purified from serum-free supernatants on a protein G (4C12) or protein A (TL1A-Ig) column (GE Healthcare, UK). For flow cytometry analysis, single cell suspensions were prepared from spleen and lymph nodes. $10^6$ cells were pre-blocked with anti-mouse CD16/CD32 and stained with different antibody combinations. Intracellular staining was performed according to standard procedures. Flow cytometric acquisition was performed on a Becton Dickinson Fortessa instrument and FACSDIVA or FlowJo software was used for analysis.

Western Blot

Standard methods were used including loading of 4-12% SDS-PAGE gels with 10-40 ng per well, gel running using standard buffers and voltages, transferring to PVDF membranes using standard methods and one-step staining using a-hIgG-HRP and subsequent detection using Pico or Femto alkaline phosphatase based detection reagents (Pierce).

Caspase Detection Assay

Human TNFRSF25 (hTNFRSF25) was cloned and used to transfect p815 cells (purchased from ATCC). Cells were transfected using standard electroporation or lipid based transfection methods. The transfected p815 cells were then co-incubated with increasing concentrations of purified hTL1A-Ig (1 pg/ml-1 μg/ml) and caspase detection assay was performed according to manufacturer protocol (Roche, Caspase 3 Activity Assay, Product 12012952001).

T Cell Proliferation Assay

These assays were performed as described in Khan et al. J. Immunol. 2013 Feb. 15; 190(4):1540-50.

Generation of Humanized Mice

Human fetal livers from elective terminations (12-20 weeks of gestational age, Advanced Bioscience Resources) were acquired on a fee for service basis. CD34+ cells were enriched using immunomagnetic beads according to the manufacturer's instructions following density gradient centrifugation of single cell suspensions (CD34+ selection kit; Miltenyi Biotec, Auburn, Calif.). Purity of CD34+ cells isolated was evaluated by flow cytometry and was >85%. Cells were aliquotted and frozen for later HLA typing and transplanted into sub-lethally irradiated neonatal NSG mice. HLA typed CD34+ cells hematopoietic stem cells (HSC) were placed into culture containing 10% human serum, 10 ng/ml each of interleukin (IL)-3, IL-6 and stem cell factor (SCF) in IMDM for 3-5 days. On the day of transplant, cells were harvested from culture dishes and washed in HBSS and CFU and LTC-IC assays were performed to evaluate proliferation and differentiation potential. These assays were performed using standard reagents (StemCell Inc.) and methods as published by the manufacturer. CFU potential was identical to bone marrow progenitor cells following 14 day culture in methylcellulose media supplemented with SCF, GM-CSF, IL-3 and EPO. These assays readily reveal whether gross morphological characteristics and colony numbers of isolated HSC are within expected limits. One-day old NSG mice generated from timed matings were housed with foster-dams for 24 hours post-irradiation (sub-lethal, 1 Gy, whole body irradiation) at which time they are transplanted with $1\times10^6$–$2\times10^6$ pre-cultured HSC intra-hepatically (i.h.) in a volume of 20 μl using a Hamilton syringe and a 30 gauge ½ inch needle. The pups were immediately returned to their foster-dams and allowed to nurse until weaning at 28 days. Human/mouse chimerism was evaluated in peripheral blood at 15 weeks of age by determining the relative percentages of murine and human CD45+ cells by flow cytometry. Once human CD45+ cells were detected, analysis was extended to include human CD3, CD4, CD8, CD11c and CD19 on all blood collections. Successfully engrafted mice were selected when the fraction of human CD45+ cells in peripheral blood exceeded 60% (NSG-hu).

Safety and Activity of TL1A-Ig in Rhesus Macaque The safety and efficacy of TL1A-Ig in non-human primates (NHP) (Indian-origin macaca mulatta) were determined. Following routine screening and 60-day quarantine, rhesus macaque (rm) TL1A-Ig or human (h) TL1A-Ig were administered to the NHP on Day 0 by intravenous (IV) bolus infusion (15 minutes) Animal weights and cage-side observations were performed daily and peripheral blood was collected for analysis of complete blood counts, routine chemistries, CD4 TruCounts, serum isolation and flow cytometry analysis. For flow cytometry analysis, peripheral blood cells were counted on a Countess automated cell counter and aliquots of $1.5\times10^6$ cells were distributed per sample tube, FMO (Fluorescent Minus One), controls, and compensation tubes. Test samples were stained in D-PBS and 0.5% FBS with 1 μL/mL live dead aqua blue discriminator (Life Technologies). Test samples and appropriate controls were surface stained for 30 minutes with the indicated cocktails of antibodies (purchased from BD, Becton Dickinson, eBioscience or Life Technologies). For intracellular staining, cells were permeabilized with Fix/perm solution (eBioscience) for 30 minutes at 4° C. Cells were washed and stained intracellularly with anti-FoxP3 antibody for 30 minutes. Following staining, cells were washed and resuspended in 300 μL, FACs wash buffer for acquisition on a BD™ LSR11 flow cytometer (Beckton Dickinson (BD)). Cells were acquired and analysis was done of FlowJo software (Tree Star, Inc., Ashland, Oreg.). For CD4/CD8 Trucounts, CD45, CD3, CD4 and CD8 antibodies were dispensed in TruCount tubes (BD, Cat.No. 340334); 50 uL samples were added and allowed to stain for 15 minutes at room temperature in the dark. Subsequently, samples are lysed with 450 μL FACS lysing solution, and incubated for 15 minutes. Sample tubes were analyzed in the cytometer (Calibur, BD). The events were gated on lymphocytes in side scatter (SSC) dot plot and the CD45-positive population was selected, and then reported: CD3+CD4+ T cells, and CD3+CD8+ T cells. For multiplex analysis of serum cytokines, serum from the indicated days was collected and samples and controls for standard curves were placed in filter plates, and then diluted ¼, and incubated for 2 hour at room temperature with anti-cytokine beads. The content was removed and washed 2 times with the buffer before adding a mixture of biotinylated detection antibodies to each well. After incubating with detection antibody for 1 hour, plates were washed 2 times and incubated for 30 minutes with streptavidin-PE. Plates were again washed and wells were resuspended with 150 μL sheath fluid; plates were then read and analyzed on the Luminex® SD Analyzer (Life Technologies, Inc.). The PE signal (Median Fluorescent Intensity, MFI) is proportional to the amount of each cytokine present in the sample; concentrations were calculated from the standard curve.

Statistical Analysis

All graphing and statistical analyses were performed using the ABI Prism® program (Applied Biosystems). Paired analysis was performed using the Student's t-test. Analysis of conditions with more than two conditions was performed using one-way ANOVA with Tukey's post-hoc test. Significance is indicated throughout Figures as * ($p<0.05$);  ($p<0.01$); and * ($p<0.001$).

Example 2

Connate Antigen-Dependent Tree Proliferation

This Example demonstrates that Treg proliferation stimulated by TNFRSF25 is dependent on cognate antigen.

A mouse model was utilized wherein $CD4^{-/-}$ mice were adoptively transferred with a mixed population of $CD4^{+}$ $FoxP3^{GFP+}$ (tTreg), which are specific for self antigen, and ovalbumin (ova)-specific $CD4^{+}V\alpha2^{+}V\beta5^{+}FoxP3^{RFP-}$ ($OTII_{conv}$, generated by crossing OT-II mice to FIR mice) as described in Schreiber, T. H., et al. 2012. Oncoimmunology 1:642-648. The model is represented as a schematic outline in FIG. 1. In these studies, tTreg are presumed to include all thymic-derived Treg cells recognizing endogenous (germline encoded) self antigens. pTreg are presumed to include all Treg that are generated from peripheral T cells that exited the thymus without expressing FoxP3, and therefore were presumed to recognize foreign (non-germline encoded) antigens. pTreg are therefore presumed to be important for regulation of immune response in tissue that regularly encounter endogenous environmental or microbial antigens including the gastrointestinal tract, skin and lungs. OT-$II_{conv}$ are cells derived from transgenic mice expressing a MHC class II restricted T cell receptor specific for the foreign antigen ovalbumin ("ova"). These cells were isolated from OT-II transgenic mice on the basis of expression of CD4 and non-expression of FoxP3.

Following a five-day oral administration of 0.5% ovalbumin in drinking water, the mice were treated with either IgG isotype control antibody or TNFRSF25 agonistic antibody, clone 4C12. After 5 days, splenocytes and mesenteric lymph node (mLN) cells were harvested and analyzed for OT-II pTreg cells and FoxP3-RFP positive nTreg cells. This model provided a tractable model in which predominantly self-antigen specific tTreg could be distinguished from OVA-specific $pTreg_{OTII}$ on the basis of $FoxP3^{GFP}$ and $FoxP3^{RFP}$ expression, respectively.

Figure 2:
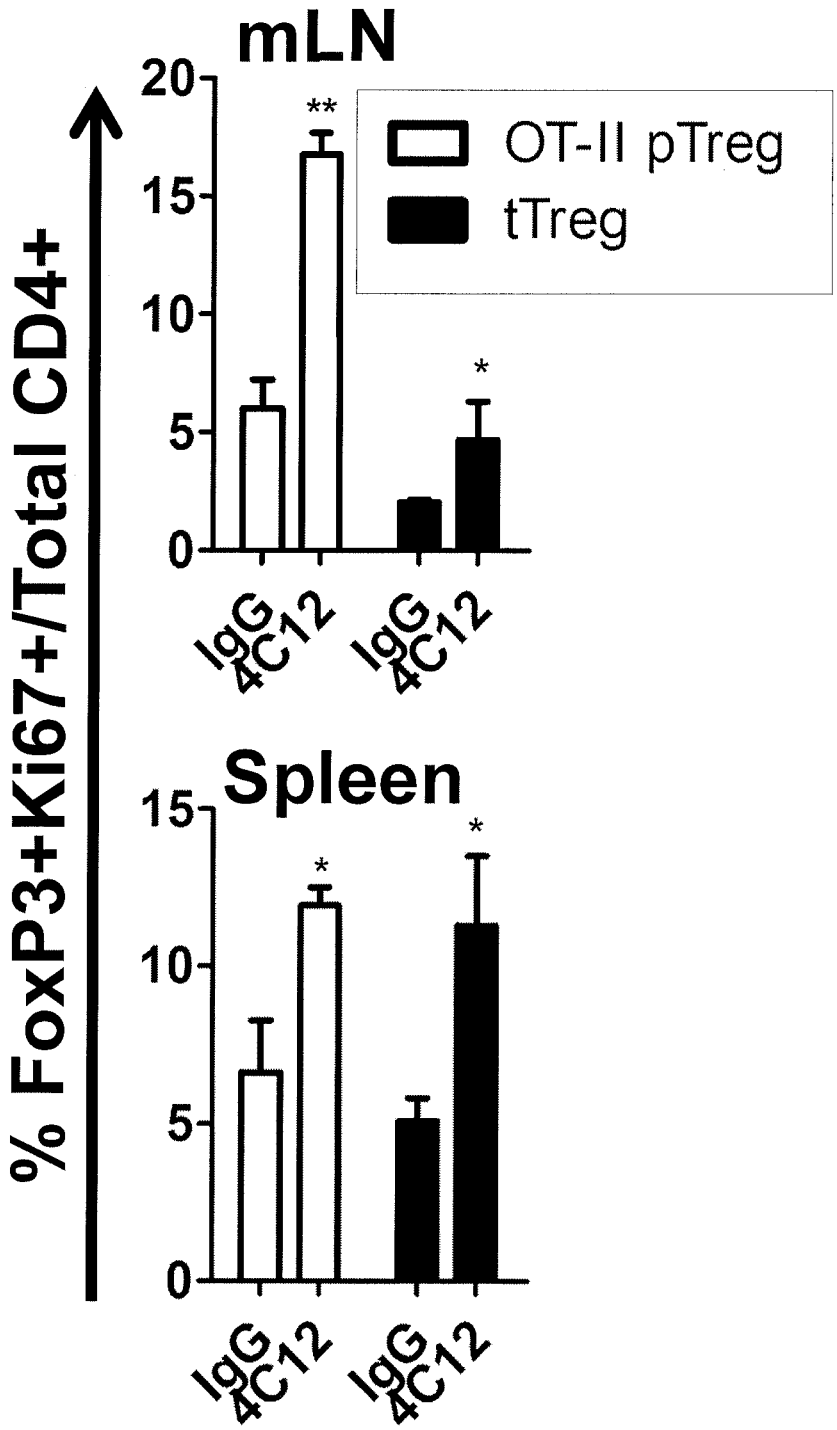
FIG. 2 depicts a bar graph quantifying the proportion of OT-II pTreg cells and FoxP3-RFP positive nTreg cells, expressed as a percentage (%) FoxP3+ Ki67+ cells out of total CD4+ cells, in mesenteric lymph node (mLN) (upper graph) and spleen cells (lower graph). Data illustrate the mean±S.E.M. with ≥3 mice per group; * indicates a statistical significance of $p<0.05$.
Figures 3A, 3B, 3C, 3D:
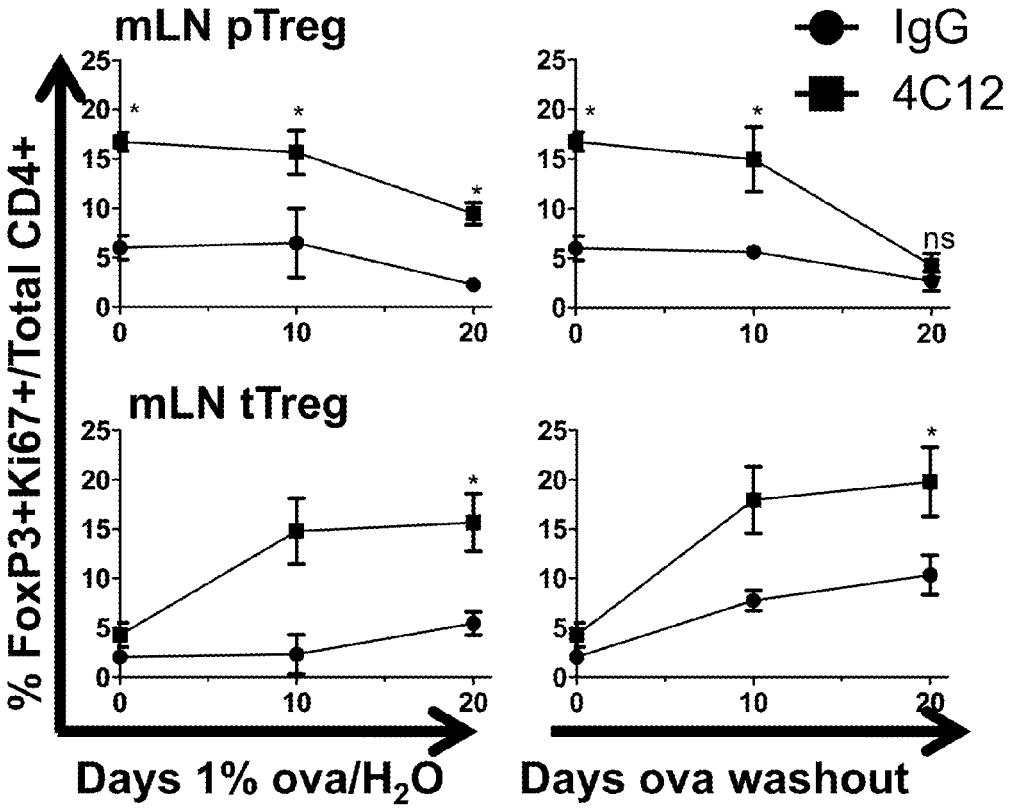
FIGS. 3A-3D are line graphs quantifying the proportion of FoxP3+Ki67+ mLN pTreg (FIGS. 3A and 3B) and in mLN tTreg (FIGS. 3C and 3D) cells out of total CD4+ cells in groups of mice that received 1% ovalbumnin (ova) in drinking water continuously (FIGS. 3A and 3C) or in groups of mice that had 1% ova containing drinking water replaced with normal water to 'washout' ova for the indicated number of days (0-20) (FIGS. 3B and 3D). One group of mice in each graph corresponds to mice that received isotype control IgG and the other group corresponds to mice that received the 4C12 antibody. Data illustrate the mean±S.E.M. with ≥3 mice per group for the 0 and 10 day time points and from 2 independent experiments with N≥4 mice per group for the 20 day time point; * indicates a statistical significance of $p<0.05$.
Figures 4A, 4B, 4C, 4D:
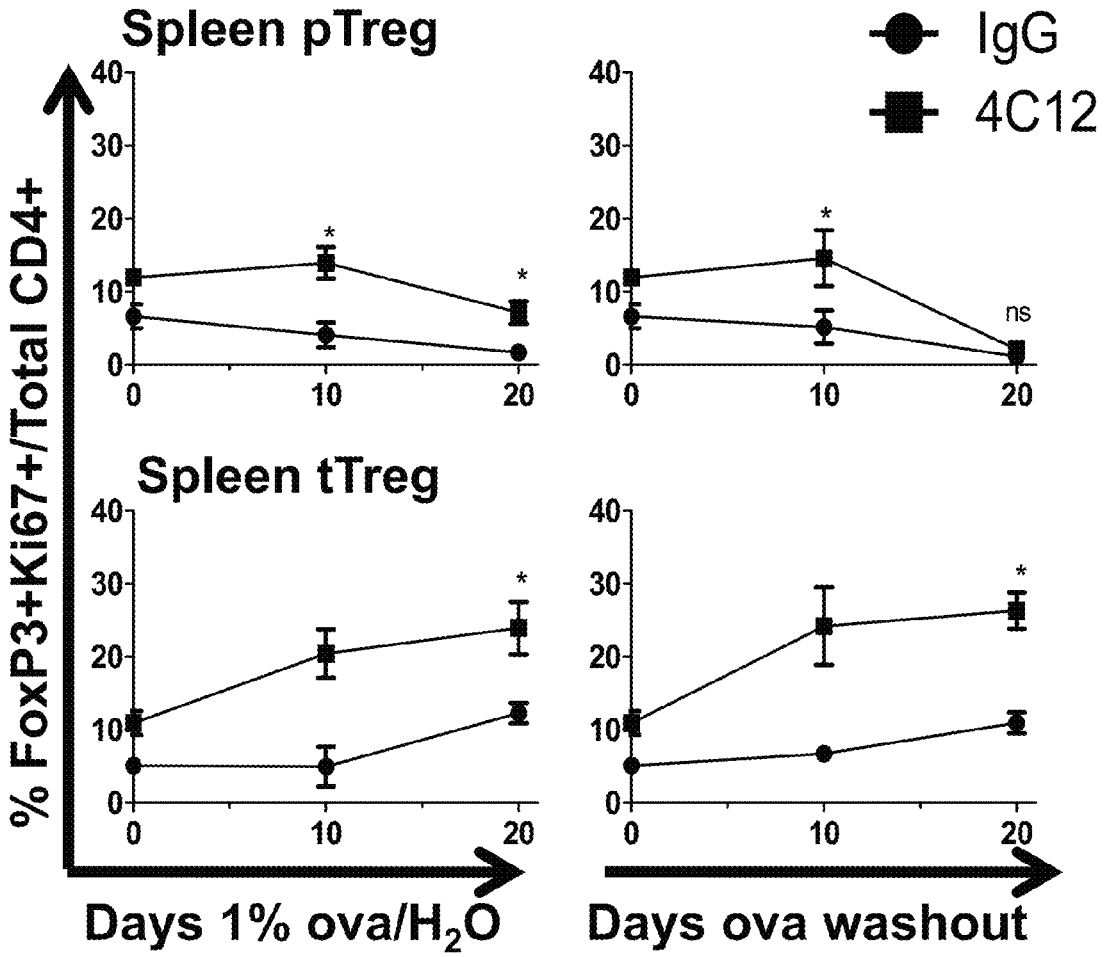
FIGS. 4A-4D are line graphs quantifying the proportion of splenic FoxP3+Ki67+ pTreg (FIGS. 4A and 4B) and in splenic tTreg (FIGS. 4C and 4D) cells out of total CD4+ cells in groups of mice that received 1% ova in drinking water continuously (FIGS. 4A and 4C) or in groups of mice that had 1% ova containing drinking water replaced with normal water to 'washout' ova for the indicated number of days (0-20) (FIGS. 4B and 4D). One group of mice in each graph corresponds to mice that received isotype control IgG and the other group corresponds to mice that received the 4C12 antibody. Data illustrate the mean±S.E.M. with ≥3 mice per group for the 0 and 10 day time points and from 2 independent experiments with N≥4 mice per group for the 20 day time point; * indicates a statistical significance of $p<0.05$.

In another experiment, following a five-day oral administration of 0.5% ovalbumin in drinking water, $CD4^{-/-}$ mice in which a mixed population of tTreg and $OTII_{conv}$, had been adoptively transferred, as above, were treated with either IgG isotype control antibody or TNFRSF25 agonistic antibody, clone 4C12. In FIG. 2, the proportionvof OT-II-iTreg cells and nTreg cells undergoing proliferation (Ki67+) in the mLN and spleen is illustrated. 6.6±1.6% of splenic $OTII_{conv}$ were induced to express $FoxP3^{RFP}$ and became $pTreg_{OTII}$. In a separate experiment, to determine the antigen-dependence of OT-II iTreg cell or nTreg cell proliferation in the mLN (FIGS. 3A-3D) and spleen (FIGS. 4A-4D), 1% ova in drinking water was either continued (FIGS. 3A, 3C, 4A and 4C) or replaced with normal water to 'washout' ovalbumin (ova) for the indicated number of days (FIGS. 3B, 3D, 4B, and 4D). After the indicated treatment period (0, 10 or 20 days), groups were treated with either IgG isotype control antibody or 4C12 antibody and OT-II iTreg cells and nTreg cells were analyzed as above, to determine the percentage of FoxP3+Ki67+ cells, in each tissue 5 days later. Following induction of $pTreg_{OTII}$ with oral administration of ovalbumin, individual cages were either maintained on ovalbumin-containing drinking water or switched to regular drinking water to determine the relationship between cognate antigen availability and sensitivity to TNFRSF25 stimulation.

Administration of the TNFRSF25 agonistic antibody, clone 4C12, prior to antigen withdrawal (day 0) led to proliferation of both $pTreg_{OTII}$ and tTreg in all mice (FIGS. 3A-3D). For all groups, proliferation of tTreg served as the internal control because of persistent availability of cognate 'self' antigen for tTreg. Following 10 days of ovalbumin antigen withdrawal ("Days ova washout"), $pTreg_{OTII}$ continued to proliferate following administration of 4C12, indicating that ovalbumin persists for at least 10 days following its withdrawal from the drinking water. Following 20 days of ovalbumin antigen withdrawal, however, no proliferation of $pTreg_{OTII}$ was observed following administration of 4C12, despite the continued proliferation of tTreg in both the mesenteric lymph nodes (FIGS. 3A-3D) and spleen (FIGS. 4A-4D). If drinking water containing ova was provided for the same 20 day period, $pTreg_{OTII}$ continued to proliferate in response to 4C12 in both tissues (mLN and spleen). These data demonstrated that withdrawal of cognate antigen prevented responsiveness of $pTreg_{OTII}$ to 4C 12 stimulated proliferation, indicating an antigen-specific response.

Example 3

Human TL1A-Ig Stimulates Proliferation of Human tTre2 in Humanized Mice

This Example demonstrates that human TL1A-Ig fusion protein induced strong proliferation of human Tregs systemically and in the mucosa of humanized mice.

Figure 5:
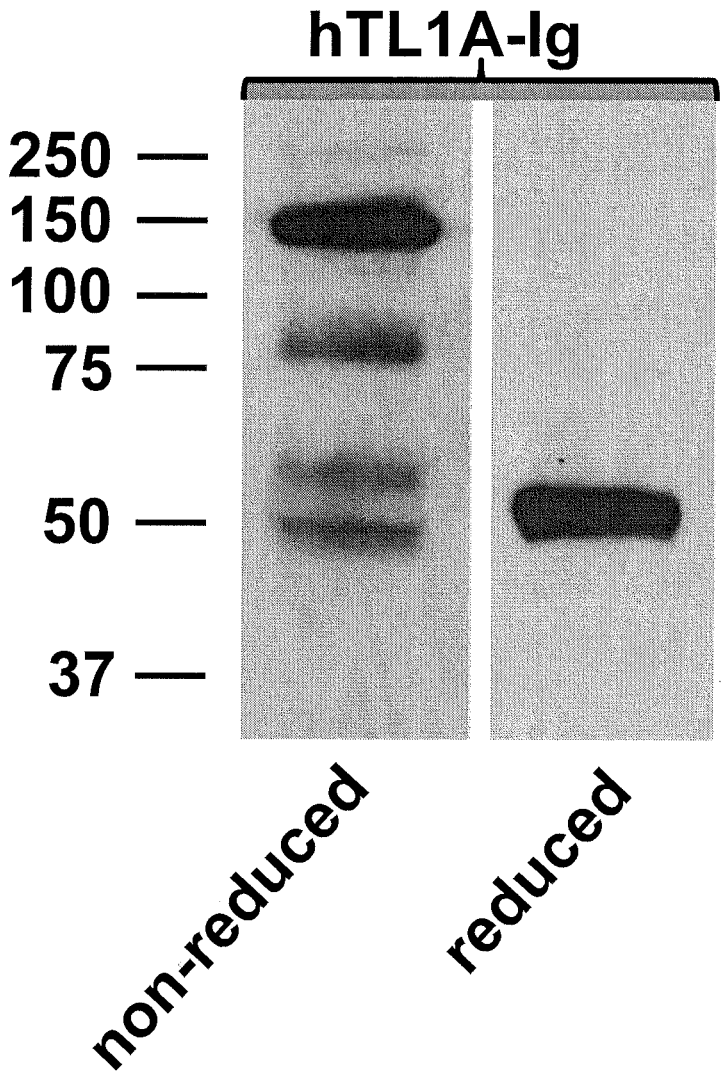
FIG. 5 depicts a Western blot of purified hTL1A under non-reduced and reduced conditions. Molecular weights are shown to the left of the photograph.
Figure 6:
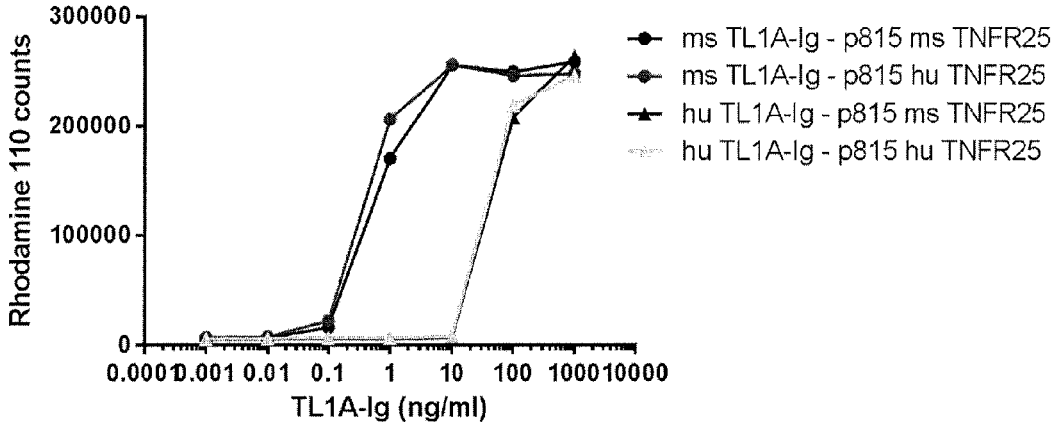
FIG. 6 depicts a line graph quantifying the functional activity (based on Rhodamine 110 counts) of human (h)TNFRSF25 transfected p815 cells treated with murine (ms) or human (hu) TL1A-Ig fusion protein at the indicated dose (ng/ml).

A fusion protein containing the extracellular domain of human TL1A and the hinge-CH2-CH3 domain of human IgG1 was cloned and purified from cell-culture supernatants, as described above. Monomeric and multimeric hTL1A-Ig complexes were identified by Western blot (FIG. 5). The in vitro activity of human TL1A-Ig (hTL1A-Ig) was demonstrated using a caspase detection assay in which human TNFRSF25 (hTNFRSF25) transfected p815 cells were co-incubated with increasing concentrations of purified hTL1A-Ig (FIG. 6).

To determine the in vivo activity of hTL1A-Ig on human Tregs, humanized mice were generated using human fetal liver $CD34^{+}$ cells transferred into NOD, SCID, common γ-chain deficient (NSG) recipient mice, as described above. Human $CD45^{+}$ cell engraftment in the experimental mice (NSG-hu) showed ≥60% chimerism in splenocytes and ≥90% chimerism in lymph nodes in all mice at 15 weeks of age. The majority of human CD45+ lymphocytes in the spleen were T cells (~50%) followed by B cells (~35%), NK cells (~2-3%) and dendritic cells (~1%).

Administration of hTL1A-Ig did not significantly alter the overall balance of $hCD45^{+}$, $hCD4^{+}$ or $hCD8^{+}$ cells in any of the spleen, lymph nodes, or small intestine in recipient mice analyzed on day 5 after injection (FIGS. 7-9). However, analysis of human Treg cells as a percentage of $FoxP3^{+}$ cells out of total $CD4^{+}CD25^{hi}CD127^{-}$ cells demonstrated a significant increase both in the total frequency of Treg and the proportion of Treg in active proliferation ($Ki67^{+}$) on day 5 after treatment in spleen, lymph node and small intestine (FIGS. 7-9). In spleen, the mean Treg value (±SEM) for the controls is 0.72±0.11% and for hTL1A-Ig 1.71±0.24% (FIGS. 7A-7D). In lymph nodes, the control mean Treg value was 0.91±0.12 whereas for hTL1A-Ig it was 1.94±0.21 (FIGS. 8A-8D). In the small intestine, the mean Treg value (±SEM) for the controls is 1.56±0.31% and for the hTL1A-Ig treated is 4.54±0.69% (FIGS. 9A-9D). Phenotypically, Treg cells had a mainly central memory ($CCR7^{+}$ $CD45^{-}RA^{-}$; ~70-80%) phenotype whereas non-Treg cells show a mainly naïve ($CCR7^{+}CD45^{-}RA^{+}$; ~70-80%) pheootype. Analysis of activation markers (CD25, CD69) expressed by conventional CD4+ and CD8+ T cells demonstrated increased expression of CD69 in both $CD4^{+}$ (p=0.0363) and $CD8^+$ (p=0.0064) conventional cells in the spleen but not in lymph nodes of hTL1A-Ig treated NSG-hu. These data demonstrated that hTL1A-Ig induced strong proliferation of human Tregs systemically and in the mucosa of humanized mice.

Similar results were obtained using the murine fusion protein, as described in detail in Khan, S. Q. et al. (supra).

Example 4

Safety and Activity of TL1A-Ig in Rhesus Macaques

This Example demonstrates that TL1A-Ig was capable of safely and selectively stimulating the proliferation of cognate Treg cells in vivo in humanized mice and primates.

An inherent limitation of rodent animal models is related to the highly controlled and restricted history of foreign antigen challenge of laboratory animals bred and housed under pathogen-free conditions. Given the antigen-dependent activity of TNFRSF25 agonists, this limitation has important consequences for translational studies of these agents into NHP, wherein the history of foreign antigen exposure is dramatically more diverse. To address this question, rhesus macaque TL1A-Ig (rmTL1A-Ig) was produced and tested in NHP. Treatment-naïve Indian-origin rhesus macaques (nonhuman primates (NHP)) were procured, housed and treated by expert personnel at Advanced Bioscience Laboratories (ABL, Rockville, Md.). Rhesus macaque TL1A-Ig (rmTL1A-Ig) and human (h) TL1A-Ig were manufactured and purified as described above and shipped to ABL personnel at the indicated concentration in blinded tubes diluted in a total volume of 10 ml PBS. After clearing 60-day quarantine, baseline complete blood counts (CBC) and serum chemistries were obtained 14 days prior to the scheduled intravenous injection of rmTL1A-Ig and hTL1A-Ig. 2 animals received 0.5 mg/kg rmTL1A-Ig, 4 animals received 1.5 mg/kg rmTL1A-Ig, and 2 animals received 1.5 mg/kg hTL1A-Ig by a single IV injection on day 0 of the study. TL1A-Ig half-life, Treg expansion, $T_{conv}$, subset and activation analysis and cytokine profiles were monitored by serial blood draws over the 21 day course of the experiment together with tissue histopathology from animals sacrificed on day 21 of the study.

Figure 10:
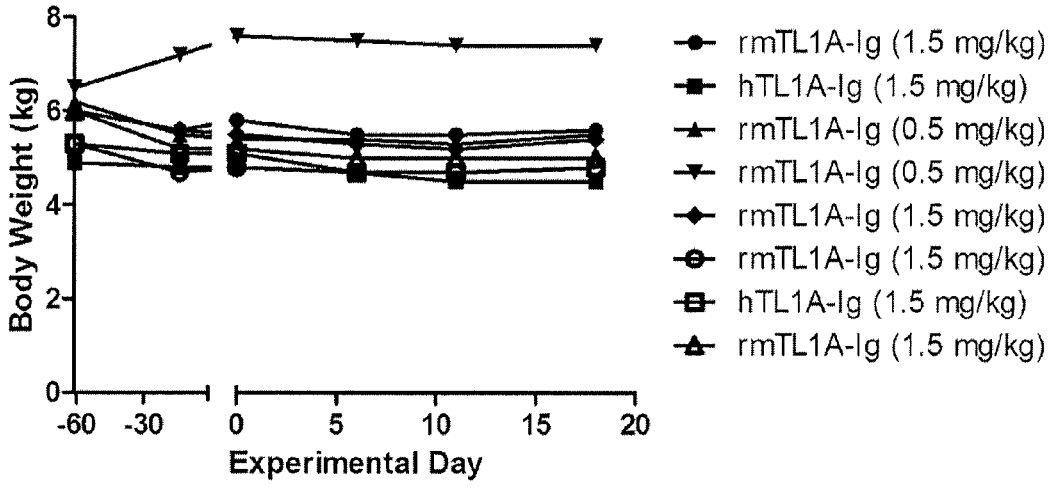
FIG. 10 depicts a line graph quantifying the body weight (kg) over time (experimental day) of rhesus macaques that were administered rhesus macaque (rm) or human (h) TL1A-Ig fusion protein at the indicated dose (mg/kg) on day 0.
Figure 11:
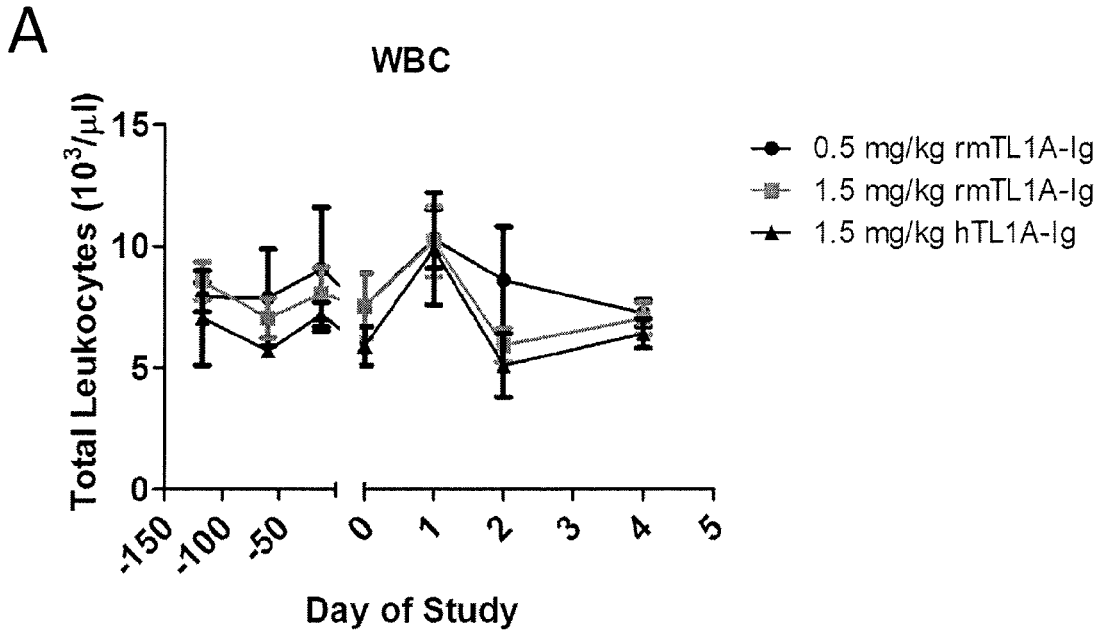
FIGS. 11A and 11B are line graphs quantifying the absolute number of leukocytes ($10^3$/μl) (FIG. 11A) and total polymorphonuclear (PMN) cells ($10^3$/μl) (FIG. 11B) determined by peripheral blood CBC analysis on the indicated day of study, following administering individual rhesus macaques rhTL1A-Ig or hTL1A-Ig fusion protein at the indicated dose on day 0.
Figure 11:
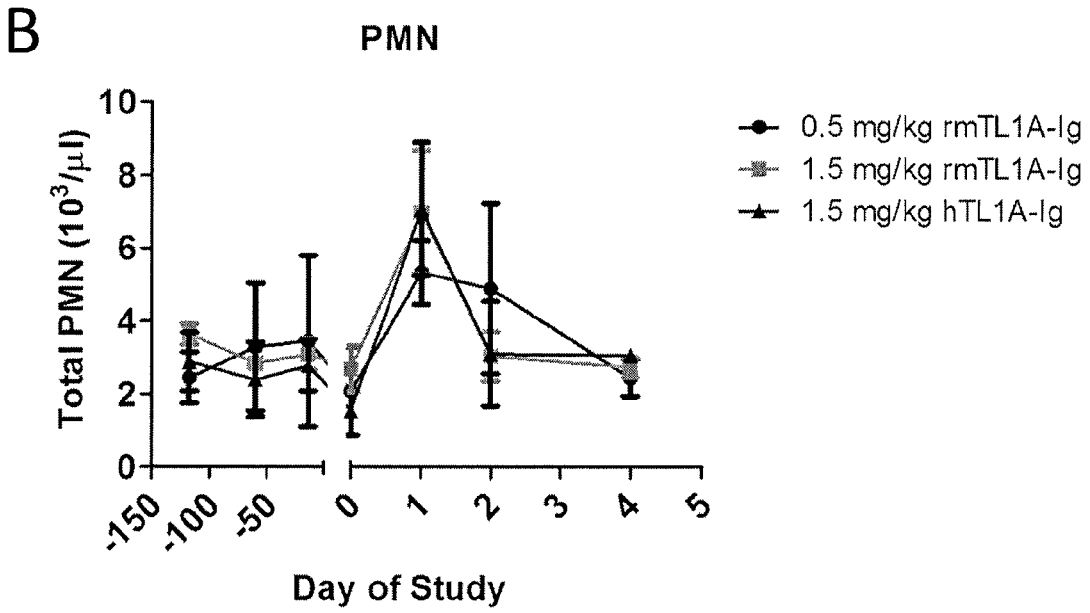

No acute toxicities were observed either in the immediate twelve hours post-injection in any NHP or during the remainder of the study. Daily cage-side observations noted normal behavior of all NHP throughout the course of the study and no evidence of wheezing, somnolence, diarrhea, vomiting, anaphylaxis, skin rashes or irritation, peripheral edema, joint effusions or mucous membrane discharge. There was no diarrhea or weight loss observed in any of the NHP over the course of the study (FIG. 10). Serum chemistries indicated no changes in electrolyte levels: sodium, potassium, phosphate, chloride, calcium, glucose, creatinine, blood urea nitrogen, total serum protein, albumin, total cholesterol or globulin. Complete blood counts indicated an increase in total white blood cells (FIG. 11A) and neutrophils (FIG. 11B) on the first day after treatment but no changes in total hemoglobin, hematocrit, total red blood cells, MCV, MCH, platelets, lymphocytes, monocytes, eosinophils or basophils over the course of the study were observed. A liver enzyme panel indicated no changes in alkaline phosphatase, total bilirubin or ALT. However, in all animals, approximate 10-fold increases in AST and creatinine phosphokinase were observed on the first day after treatment, increases which are routinely observed in NHP following intramuscular injection of anesthetic prior to the treatment protocol. The levels of AST and CPK returned to baseline by day 4 of the study in all animals.

Figure 12:
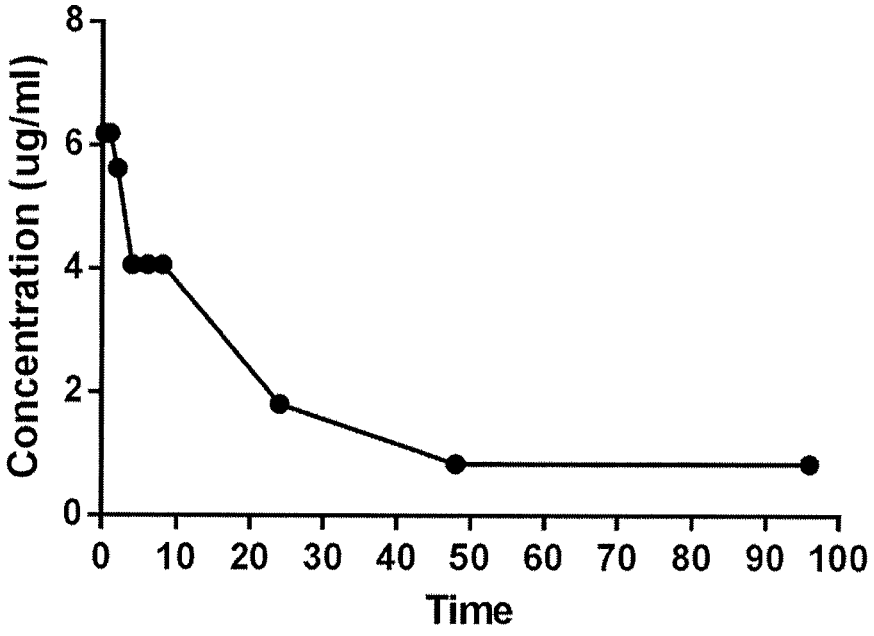
FIG. 12 depicts a line graph quantifying the mean concentration (μg/ml) of human TL1A-Ig fusion protein over time in serum of rhesus macaques treated with the fusion protein.
Figure 14:
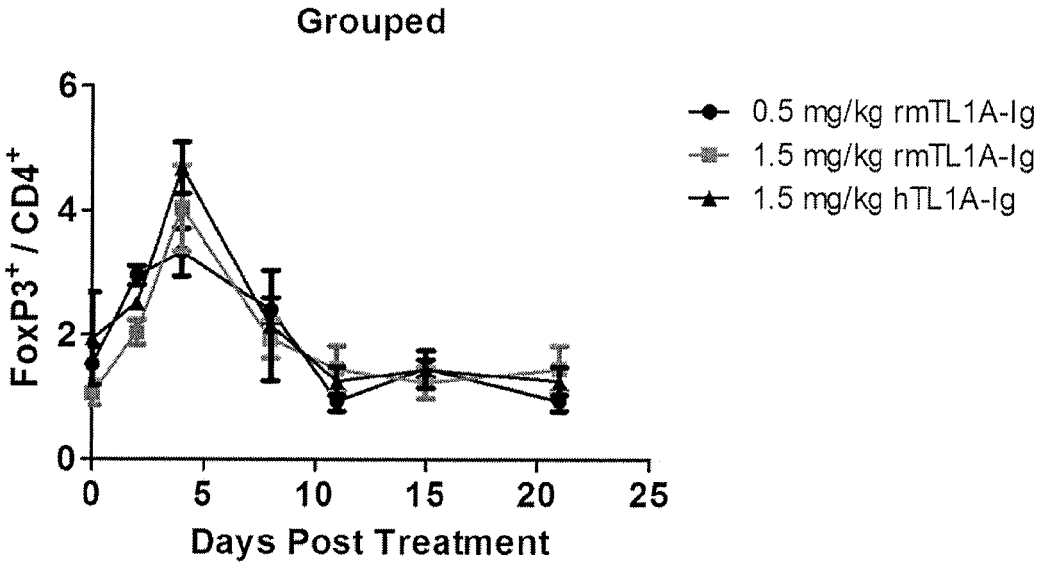
FIGS. 14-15 depict line graphs quantifying the frequency (%) of FoxP3 Treg cells (out of total CD4+ cells) (FIG. 14) and the frequency (%) of CD28+CD95− naïve CD4 T cells (out of total CD4+CCR7+) (FIG. 15) in rhesus macaques on the indicated day post treatment with rhTL1A-Ig or hTL1A-Ig fusion protein at the indicated dose on day 0.

Analysis of serially collected serum samples indicated a half-life of 12.5 hours for hTL1A-Ig in NHP, calculated using a one-phase exponential decay model (FIG. 12). Multiplex analysis (Luminex®) of serum cytokines at baseline (day 0), day 2 and at the time of peak Treg expansion (day 4) demonstrated no detectable changes in the levels of IL-2, IL-4, IL-5, IL-10 or TNF-α, and a trend toward decreased levels of IFN-γ and TGF-β by day 4 after treatment (FIGS. 13A-13B). Analysis of peripheral blood Treg cells by flow cytometry demonstrated nearly identical relative magnitude and kinetics of in vivo Treg expansion in rhesus macaque as compared to humanized mice (FIG. 14). The relative fold-expansion peaked at 4 days post-treatment with approximately 3-fold expansion of the Treg compartment. Similar responses were observed using 1.5 mg/kg of both rmTL1A-Ig and hTL1A-Ig, with the 0.5 mg/kg rmTL1A-Ig dose demonstrating a non-significantly reduced trend for Treg expansion.

Figure 15:
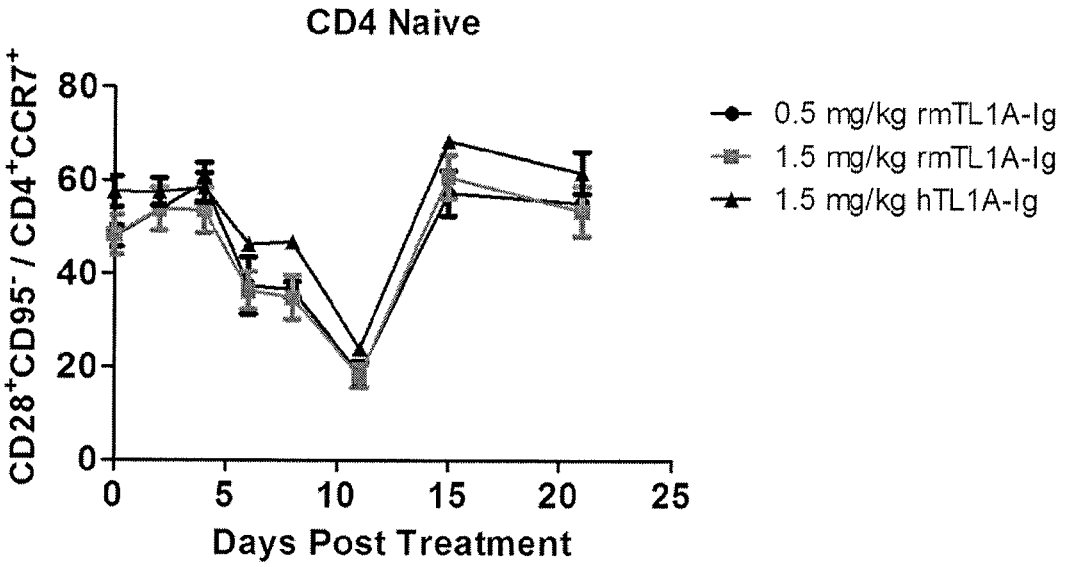

To monitor for CD4+ and CD8+ $T_{conv}$ cell activation, naïve (CCR7+CD28+CD95−), central memory (CCR7+CD28+CD95+), effector memory (CCR7−CD28−CD95+) and transitional effector memory (CCR7−CD28+CD95+) T cell subsets were monitored over the course of the experiment in the peripheral blood. This analysis demonstrated no significant fluctuations in the CD8 naïve, central memory, effector memory or transitional effector memory T cell compartments. Within the CD4 compartment, there was a significant reduction in the frequency of peripheral blood naïve CD4 cells by day 11 of the study, which then rapidly rebounded to baseline by day 15 (FIG. 15). Although not significant, there was a trend toward increased frequencies of CD4 central memory by day 11 of the study, which, when adjusted for absolute cell numbers, demonstrated no change; indicating that this relative difference was likely related to the relative reduction in naïve cells rather than a proliferative effect on central memory cells.

Although there was no evidence of CD4+ or CD8+ effector T cell activation or increased concentrations of inflammatory cytokines immediately following TL1A-Ig administration, it remained possible that signs of sub-clinical immunopathology may be present within individual tissues. To investigate signs of immunopathology within individual tissues, 2 animals receiving rmTL1A-Ig (1.5 mg/kg) and the 2 animals receiving hTL1A-Ig (1.5 mg/kg) were selected for necropsy and end-organ histopathology on day 21 of the study. Analysis of hematoxylin and eosin stained sections of the midbrain, brainstem, liver and pancreas demonstrated no evidence of inflammation or pathology in any of the animals analyzed. In one animal, lung sections demonstrated evidence of minimal, multifocal perivascular lymphocytic aggregates, with the remaining three animals interpreted as essentially normal lung tissue. In two animals, sections of haired skin were shown to exhibit mild to moderate areas of focally extensive dermal edema, with the remaining two animals interpreted as essentially normal skin tissue. In three of the four animals, jejunal sections demonstrated evidence of mild, diffuse submucosal edema. In four out of four animals, sections of the terminal ileum demonstrated evidence of mild, diffuse mucosal and submucosal edema. In four out of four animals, sections of sigmoid colon demonstrated evidence of mild, multifocal, lymphoplasmacytic infiltrates. Mesenteric lymph node sections were interpreted as essentially normal tissue in three or four animals, with one animal showing evidence of mild, diffuse lymphocytosis.

Together, these results provide evidence that stimulation of TNFRSF25 with receptor agonistic antibodies and ligand fusion proteins provides a unique and specific method for in vivo modulation of human and NHP Treg cells. The kinetics and specificity of Treg stimulation are remarkably similar in mice, in NSG-hu and in NHP following treatment with mouse, rhesus macaque and human-specific TL1A-Ig; which may indicate that the underlying mechanism involving cognate antigen/TCR engagement, IL-2 receptor and Akt activation is also conserved in humans as was also demonstrated in mice (Khan et al. (supra)). The observation in NHP of a decrease in naïve CD4 T cells immediately following the peak in Treg expansion in the peripheral blood may indicate evidence of in vivo suppression of CD4 naïve cells.

Discussion

The data in Examples 2-4 indicate that TL1A-Ig is a molecule capable of safely and selectively stimulating the proliferation of cognate Treg cells in vivo in mice, NSG-hu and NHP. Of particular concern were possible susceptibilities to inflammatory bowel disease (IBD) due both to epidemiologic data linking TL1A polymorphism to IBD in humans and to murine studies demonstrating that transgenic expression of TL1A predisposes to IBD susceptibility. Because tolerance to endogenous 'foreign' antigens in the gut is particularly dependent upon the immunosuppressive activity of Treg, it was predicted that modulation of TNFRSF25 in NHP would lead to similar immunopathology. No such toxicities were observed in these studies as demonstrated by behavioral changes, diarrhea or weight loss over the course of these studies, and there was no evidence of diffuse effector cell activation or inflammatory cytokine production in the peripheral blood. End-organ histopathology demonstrated only mild accumulation of lymphoid cells within the terminal ileum and sigmoid colon, without overt signs of tissue immunopathology.

Example 5

Combination Therapy with TNFRSF25 Agonists and IL-2

This Example demonstrates the surprising and unexpected discovery that the combination of a low or a very dose of IL-2 with a TNFRSF25 agonist, such as TL1A-Ig fusion protein or the agonistic anti-TNFRSF25 antibody 4C12, had a synergistic effect on the expansion of Treg cells in vivo.

In a first set of experiments, wild type mice were treated with low-dose IL-2 (300,000 units/$m^2$), control (IgG), TL1A-Ig (0.5 mg/kg), or a combination treatment with TL1A-Ig and a single injection of very low-dose IL-2 (30,000 units/$m^2$) or with a combination treatment with TL1A-Ig and a single injection of low dose IL-2 (300,000 units/$m^2$). The frequency of CD4+FoxP3+ cells out of total CD4+ cells was monitored in the peripheral blood on the indicated days.

Figure 16:
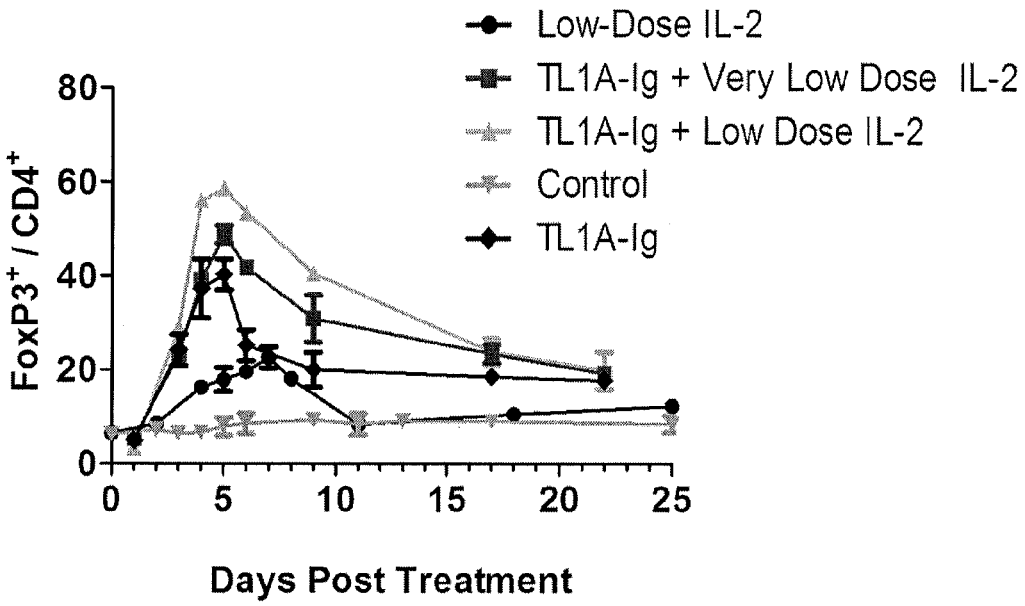
FIG. 16 is a line graph quantifying the frequency (%) of FoxP3+CD4+ Treg cells out of total CD4+ cells (cells were pre-gated on CD3+ cells) on the Y-axis versus the number of days post treatment with the indicated treatment regimen (Low-dose IL-2 (300,000 units); TL1A-Ig fusion protein+ very low dose IL-2 (30,000 units); TL1A-Ig fusion protein+ Low Dose IL-2 (300,000 units); control (IgG); or TL1A-Ig fusion protein) on the X-axis. Data are illustrated as the mean±SEM using 3 mice per group. Day 5 analysis using one-way ANOVA with Tukey post test demonstrated significant differences for TL1A-Ig vs control ($p<0.05$), TL1A-Ig+very low dose IL-2 vs control ($p<0.01$) and TL1A-Ig plus low dose IL-2 versus control ($p<0.001$).

As shown in FIG. 16, treatment with TL1A-Ig and either dose of IL-2 (very lose dose IL-2 (30,000 units) or low dose (300,000 units) had a synergistic effect on the Treg cell expansion compared to treatment with TL1A-Ig or IL-2 alone. For example, 5 days post-treatment, the percentage of FoxP3+ Treg cells was 60% in mice treated with TL1A-Ig and Low Dose IL-2, and 50% in mice treated with TL1A-Ig and very lose dose IL-2, compared to 40% in mice treated with TL1A-Ig and less than 20% in mice treated with Low dose IL-2 alone. The synergistic effect was even more pronounced 6 days after treatment, when the frequency of Treg cells was 55% and about 40% following combination treatment with TL1A-Ig and low or very low dose IL-2, respectively, compared to less than 25% and less than 20% following treatment with TL1A-Ig or Low dose IL-2, respectively.

In a second set of experiments, wild type mice were treated with low-dose IL-2 (300,000 units/m2), control (IgG), 4C12 antibody (0.4 mg/kg), or with a combination treatment with 4C12 antibody and a single injection of low dose IL-2 (300,000 units/m2). The frequency of CD4+ FoxP3+ cells out of total CD4+ cells was monitored in the peripheral blood on the indicated days.

Figure 17:
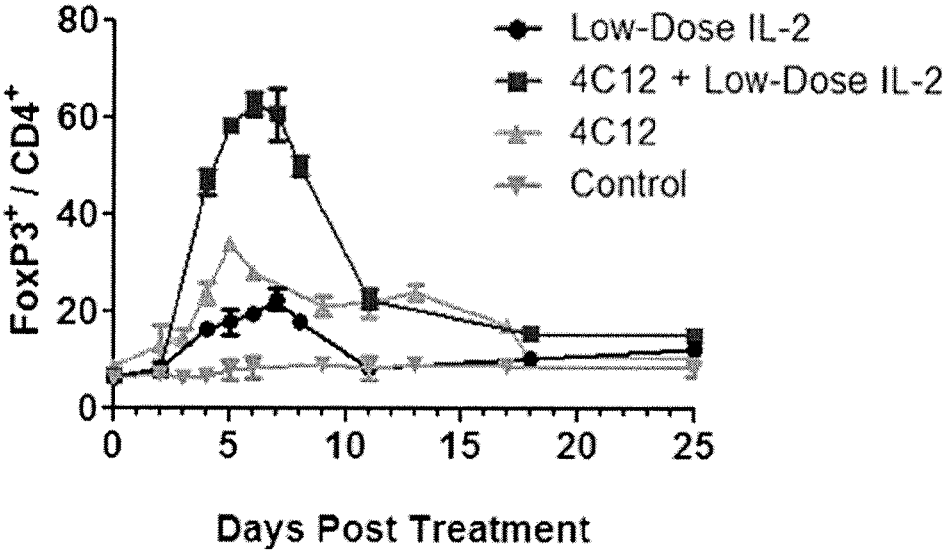
FIG. 17 is a line graph quantifying the frequency (%) of FoxP3+CD4+ Treg cells out of total CD4+ cells (cells were pre-gated on CD3+ cells) on the Y-axis versus the number of days post treatment with the indicated treatment regimen (Low-dose IL-2 (300,000 units); 4C12 antibody+Low Dose IL-2 (300,000 units); 4C12 antibody; or control (IgG)) on the X-axis. Data are illustrated as the mean±SEM using 5 mice per group. Day 5 analysis using one-way ANOVA with Tukey post test demonstrated significant differences for 4C12 vs control ($p<0.05$) and 4C12+ low dose IL-2 vs control ($p<0.001$).

As shown in FIG. 17, treatment with a combination of the 4C12 antibody and the Low Dose IL-2 had a dramatic, synergistic effect on expansion of Treg cells. Six days after treatment with the 4C12/IL-2 combination, the frequency of Treg cells was about 70% of all CD4+ CD3+ peripheral blood cells, compared to about 30% of all CD4+ CD3+ peripheral blood cells, and less than 20% of all CD4+ CD3+ peripheral blood cells, in mice that received only 4C12 antibody or only low-dose IL-2, respectively.

The results achieved with the above-described combination therapies were surprising and unexpected, for a number of reasons. For example: 1) the TNFRSF25 agonist/IL-2 combination achieved Treg expansion at a dose of IL-2 (300,000 units) not previously shown to expand Treg cells; 2) the combination treatments achieved Treg expansion at a 10-fold lower dose than what had been considered "low-dose" IL-2 (30,000 units); and 3) the magnitude of Treg expansion was unprecedented. This is believed to be the first description of obtaining 50% Treg cells in the CD4 compartment (i.e., 50% of all CD4+ cells were Treg cells), and in the case of 4C 12/low dose IL-2, that fraction even reached 70%. Furthermore, these high numbers of Treg cells were achieved using both TL1A-Ig and TNFRSF25 agonistic antibodies in the combination therapy with IL-2, indicating that this is a property of the receptor itself and not of a specific reagent.

Example 6

Combination Therapy with TL1A-Ig and Rapamycin

This Example demonstrates the surprising and unexpected discovery that the combination of rapamycin with TL1A-Ig fusion protein preserved Treg cell expansion in vivo while eliminating concurrent effector T cell activation.

Wild-type mice were adoptively transferred with ovalbumin specific CD8 (OT-I) or CD4 (OT-II) T cells on day-2. Mice were then immunized with Aluminum hydroxide ("alum")-adjuvanted ovalbumin together with either control IgG, TL1A-Ig (0.5 mg/kg) and/or a 6-day course of low-dose rapamycin (75 μg/kg). The frequency of OT-I cells out of total CD8+ cells, OT-II cells out of total CD4+ cells, and the frequency of CD4+FoxP3+ cells (Treg cells) out of total CD4+ cells were monitored by flow cytometry over 18 days.

Figure 18:
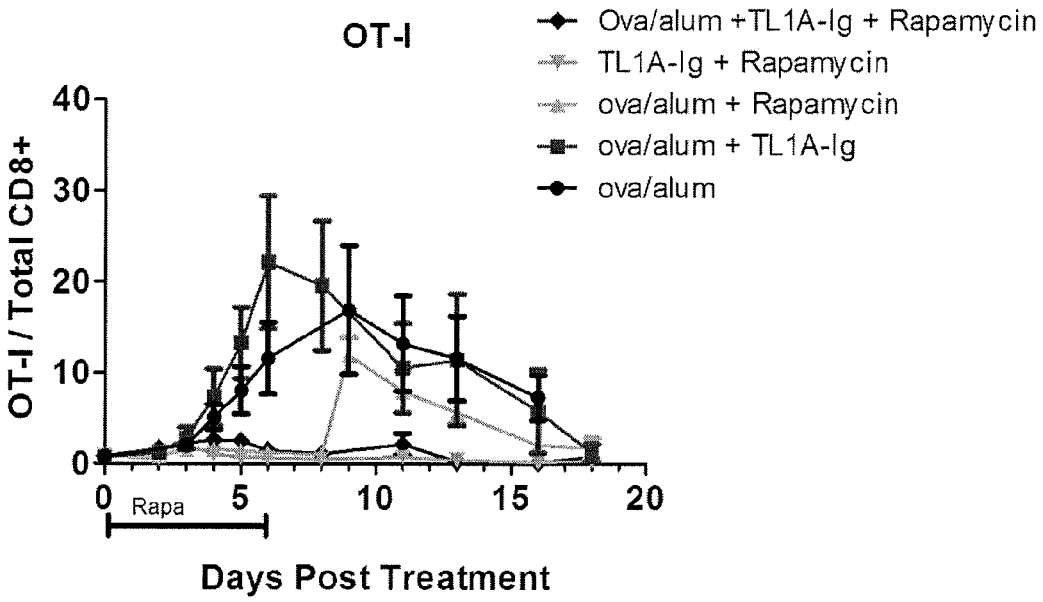
FIGS. 18, 19 and 20 depict line graphs quantifying the frequency (percentage) of adoptively transferred OT-I (CD8+ ovalbumin (ova)-specific) T cells out of total CD8+ T cells (FIG. 18), or of adoptively transferred OT-II (CD4+ ova-specific) T cells out of total CD4+ T cells (FIG. 19), or of CD4+FoxP3+ Treg cells out of total CD4+ cells (FIG. 20) in the peripheral blood of mice from the groups treated as indicated in the graph (Ova/alum+TL1A-Ig fusion protein+ Rapamycin; TL1A-Ig fusion protein+Rapamycin; ova/alum+Rapamycin; ova/alum+TL1A-Ig fusion protein; or ova/alum). Data are illustrated as the mean±SEM using 6 mice per group from a total of two independent experiments.
Figure 19:
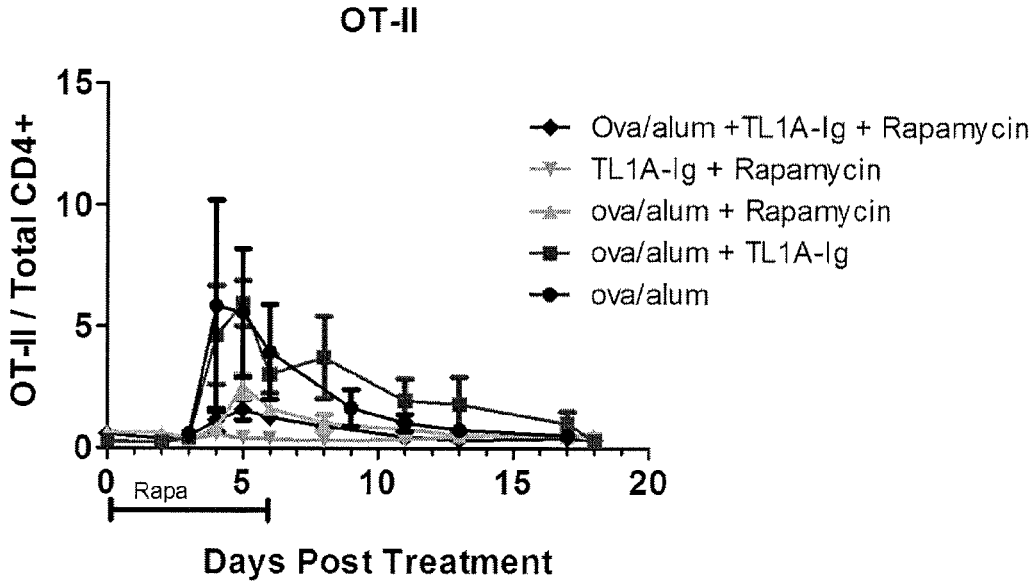
Figure 20:
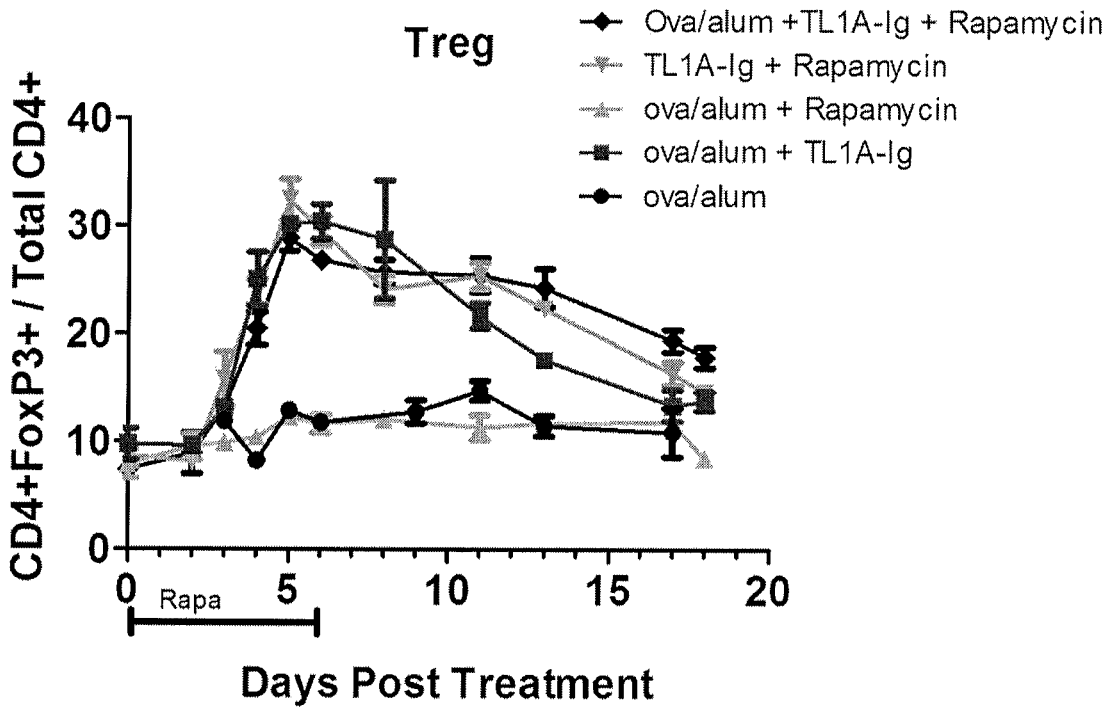

As shown in FIG. 18 and FIGS. 19, the overall frequency of CD8+ (OT-I) and CD4+ (OT-II) cells following treatment that included rapamycin was markedly reduced. What was most striking, however, was that the frequency of Treg cells following treatment with OVA/alum, TL1A-Ig, and Rapamycin was not affected (FIG. 20), indicating the effect of rapamycin was specifically on activated T effector cells and not Treg cells.

This finding was surprising and indicates that therapies that involve the administration of TNFRSF25 agonists (such as TL1A-Ig fusion protein, and other agonists, e.g., 4C12 antibody) benefit from co-administration of rapamycin to prevent unwanted activation and expansion of CD4 and CD8 T effector cells.

Prophetic Example 1

Administration to Human Subjects of Human TL1A-Ig Fusion Protein

The hTL1A-Ig fusion protein is formulated in buffered saline for intravenous administration. Increasing dosages, ranging from 0.1 mg/kg/day to 10 mg/kg/day of hTL1A-Ig fusion protein, prepared and isolated as described in Example 1, above, are administered to human patients as an induction agent several days prior to solid organ or stem cell transplantation. The efficacy of this treatment is then measured by serial blood draws over a period of several weeks wherein the frequencies of Treg cells, T effector ($T_{eff}$) cells and inflammatory cytokines are measured in the peripheral blood of treated subjects. Long-term benefit of this treatment is also measured in treated subjects based on the ability for early weaning of standard immunosuppressive maintenance therapy including, but not limited to, tacrolimus or other mTOR inhibitors, cyclosporine inhibitors and steroid regimens including prednisone and methylprednisone.

An initial safety study may also be performed in healthy subjects wherein 0.1-10 mg/kg/day hTL1A-Ig is administered in buffered saline intravenously. The function of hTL1A-Ig is then measured in treated subjects by serial blood draws over a period of several weeks wherein the frequencies of Treg cells, Teff cells and inflammatory cytokines are measured in the peripheral blood of treated subjects. Safety is also monitored using standard observational methods.

Prophetic Example 2

Combination Therapy with Human TL1A-12 Fusion Protein and Interleukin-2

The hTL1A-Ig fusion protein is formulated in buffered saline for intravenous administration in a dosage found to be effective in Prophetic Example 1, above (e.g., in the range from 0.1 mg/kg/day to 10 mg/kg/day), prepared and isolated as described in Example 1, above. The hTL1A fusion protein is administered to human patients as an induction agent several days prior to solid organ or stem cell transplantation. One or two days prior to, on the same day as, or one or two days following the administration of the hTL1A-Ig fusion protein, the patients are also administered either low dose (300,000 units) or very low dose (30,000 units) or a dose between 30,000 and 300,000 units per square meter of IL-2 intravenously.

The efficacy of this treatment is then measured by serial blood draws over a period of several weeks wherein the frequencies of Treg cells, T effector ($T_{eff}$) cells and inflammatory cytokines are measured in the peripheral blood of treated subjects. Long-term benefit of this treatment is also measured in treated subjects based on the ability for early weaning of standard immunosuppressive maintenance therapy including, but not limited to, tacrolimus or other mTOR inhibitors, cyclosporine inhibitors and steroid regimens including prednisone and methylprednisone.

Prophetic Example 3

Combination Therapy with TNFRSF25 Agonist and Rapamycin

The human TL1A-Ig fusion protein described in, e.g., Examples 1 and 3, above, or an agonistic anti-TNFRSF25 antibody is formulated in buffered saline for intravenous administration in an effective dosage (e.g., for TL1A-Ig fusion protein, a dosage found to be effective in Prophetic Example 1, above (e.g., in the range from 0.1 mg/kg/day to 10 mg/kg/day), prepared and isolated as described in Example 1, above. The human TL1A fusion protein or agonistic anti-TNFRSF25 antibody is administered to human patients as an induction agent several days prior to solid organ or stem cell transplantation. One or two days prior to, on the same day as, or one or two days following the administration of the TNFRSF25 agonist, the patients are also administered rapamycin at a dosage of between 75 and 300 micrograms per kg body weight per day.

The efficacy of this treatment is then measured by serial blood draws over a period of several weeks wherein the frequencies of Treg cells, T effector ($T_{eff}$) cells and inflammatory cytokines are measured in the peripheral blood of treated subjects. Long-term benefit of this treatment is also measured in treated subjects based on the ability for early weaning of standard immunosuppressive maintenance therapy including, but not limited to, tacrolimus or other mTOR inhibitors, cyclosporine inhibitors and steroid regimens including prednisone and methylprednisone.

A number of embodiments of the invention have been described. Nevertheless, it will be understood that various modifications may be made without departing from the spirit and scope of the invention. It is further to be understood that all values are approximate, and are provided for description. Accordingly, other embodiments are within the scope of the following claims.

SEQUENCE LISTING

```
<160> NUMBER OF SEQ ID NOS: 16

<210> SEQ ID NO 1
<211> LENGTH: 756
<212> TYPE: DNA
<213> ORGANISM: Homo sapiens

<400> SEQUENCE: 1

atggccgagg atctgggact gagctttggg gaaacagcca gtgtggaaat gctgccagag      60

cacggcagct gcaggcccaa ggccaggagc agcagcgcac gctgggctct cacctgctgc     120

ctggtgttgc tccccttcct tgcaggactc accacatacc tgcttgtcag ccagctccgg     180
```

```
gcccagggag aggcctgtgt gcagttccag gctctaaaag gacaggagtt tgcaccttca    240

catcagcaag tttatgcacc tcttagagca gacggagata agccaagggc acacctgaca    300

gttgtgagac aaactcccac acagcacttt aaaaatcagt tcccagctct gcactgggaa    360

catgaactag gcctggcctt caccaagaac cgaatgaact ataccaacaa attcctgctg    420

atcccagagt cgggagacta cttcatttac tcccaggtca cattccgtgg gatgacctct    480

gagtgcagtg aaatcagaca agcaggccga ccaaacaagc cagactccat cactgtggtc    540

atcaccaagg taacagacag ctaccctgag ccaacccagc tcctcatggg gaccaagtct    600

gtatgcgaag taggtagcaa ctggttccag cccatctacc tcggagccat gttctccttg    660

caagaagggg acaagctaat ggtgaacgtc agtgacatct ctttggtgga ttacacaaaa    720

gaagataaaa ccttctttgg agccttctta ctatag                              756


<210> SEQ ID NO 2
<211> LENGTH: 251
<212> TYPE: PRT
<213> ORGANISM: Homo sapiens

<400> SEQUENCE: 2

Met Ala Glu Asp Leu Gly Leu Ser Phe Gly Glu Thr Ala Ser Val Glu
1               5                   10                  15

Met Leu Pro Glu His Gly Ser Cys Arg Pro Lys Ala Arg Ser Ser Ser
            20                  25                  30

Ala Arg Trp Ala Leu Thr Cys Cys Leu Val Leu Leu Pro Phe Leu Ala
        35                  40                  45

Gly Leu Thr Thr Tyr Leu Leu Val Ser Gln Leu Arg Ala Gln Gly Glu
    50                  55                  60

Ala Cys Val Gln Phe Gln Ala Leu Lys Gly Gln Glu Phe Ala Pro Ser
65                  70                  75                  80

His Gln Gln Val Tyr Ala Pro Leu Arg Ala Asp Gly Asp Lys Pro Arg
                85                  90                  95

Ala His Leu Thr Val Val Arg Gln Thr Pro Thr Gln His Phe Lys Asn
            100                 105                 110

Gln Phe Pro Ala Leu His Trp Glu His Glu Leu Gly Leu Ala Phe Thr
        115                 120                 125

Lys Asn Arg Met Asn Tyr Thr Asn Lys Phe Leu Leu Ile Pro Glu Ser
    130                 135                 140

Gly Asp Tyr Phe Ile Tyr Ser Gln Val Thr Phe Arg Gly Met Thr Ser
145                 150                 155                 160

Glu Cys Ser Glu Ile Arg Gln Ala Gly Arg Pro Asn Lys Pro Asp Ser
                165                 170                 175

Ile Thr Val Val Ile Thr Lys Val Thr Asp Ser Tyr Pro Glu Pro Thr
            180                 185                 190

Gln Leu Leu Met Gly Thr Lys Ser Val Cys Glu Val Gly Ser Asn Trp
        195                 200                 205

Phe Gln Pro Ile Tyr Leu Gly Ala Met Phe Ser Leu Gln Glu Gly Asp
    210                 215                 220

Lys Leu Met Val Asn Val Ser Asp Ile Ser Leu Val Asp Tyr Thr Lys
225                 230                 235                 240

Glu Asp Lys Thr Phe Phe Gly Ala Phe Leu Leu
                245                 250
```

<210> SEQ ID NO 3
<211> LENGTH: 1659
<212> TYPE: DNA
<213> ORGANISM: Rhesus macaque

<400> SEQUENCE: 3 ggaaaaggga aggaggagac tgagtgatta agtcacccac tgtgagagct ggtcttctat 60 ttaatggggg ctctctctgc ccaggagtca gaggtgcctc caggagcagc aagagcatgg 120 ccgaggatct gggactgagc tttggggaga cagccagtgt ggaaatgctg ccagagcacg 180 gcagctgcag gcccaaggcc aggagcagca gcgcatgctg ggctctcacc tgctgcctgg 240 tgttgctccc cttccttgca gggctcacca cctacctgct tgtcagccag ctccgggccc 300 aaggagaggc ctgtgtgcag ctccaggatc taaaaggaca ggagtttgca ccttcacatc 360 agcaagttta tgcacctctt agagcagatg gagataagcc aagggcacac ctgacagttg 420 tgagacaaac tcccacacag cacttaaaaa atcagttccc agctctgcac tgggaacatg 480 aactaggcct ggccttcacc aagaaccgaa tgaactatac caacaaattc ctgctgatcc 540 cagagtcggg agactacttc gtttactccc aggtcacatt ccgtgggatg acctctgagt 600 gcagtgaaat cagacaagca ggccgaccaa acaagccaga ctccatcact gtggtcatca 660 ccaaggtaac agacagctac cctgagccaa cccagctcct catggggacc aagtctgtgt 720 gtgaagtagg cagtaactgg ttccagccca tctacctcgg agccatgttc tccttgcaag 780 aaggggacaa gctcatggtg aacgtcagtg acatctcttt ggtggattac acaaaagaag 840 ataaaacctt ctttggagcc ttcttactat aggaggagag caaatatcat tatgtgaagt 900 cctctgccac cgagttccta attttcttcg ttcaaatgta attacaacca ggggttttct 960 tggggccggg agtagggggc attccgcagg gacaatggtt tagctatgaa atttggggcc 1020 caaaatttca cacttcatgt gccttactga tgaaagtact aactggaaaa aggctgaaga 1080 gagcaaatat attattatgg tgggttggag gattggtgag tttctaaata ttaagacact 1140 gatcactaaa cgaatggatg atctactcag gtcaggattg aaagagaaat atttcaacac 1200 cttcctgcta cacaatggtc accagtggtc cagttattgt tcaatttgat cataaatttg 1260 cttcaattca ggagctttga aggaagtcca aggaaagctc tagaaaacag tataaacctt 1320 cagaggcaaa atccttcacc aatttttccg catactttca tgccttgcct aaaaaaatta 1380 acagagagtt ggtatgtctc atgaatgctc tcacagaagg agttgctttt catgtcatct 1440 acagcatatg agaaaagcta cctttctttt gattatatac acagatatca aaataagcaa 1500 ggatgagttt tacgtgtata tcaaaaatac aacagttgct tgtattcagc cgagttttct 1560 tgaccaccta ttatgttctg ggtgctacct taacccagaa gacactatga aaaacaagac 1620 agacttcact caaaacttac atgaacacca ctagatgct 1659

<210> SEQ ID NO 4
<211> LENGTH: 251
<212> TYPE: PRT
<213> ORGANISM: Rhesus macaque

<400> SEQUENCE: 4

Met Ala Glu Asp Leu Gly Leu Ser Phe Gly Glu Thr Ala Ser Val Glu
1 5 10 15

Met Leu Pro Glu His Gly Ser Cys Arg Pro Lys Ala Arg Ser Ser Ser
20 25 30

Ala Cys Trp Ala Leu Thr Cys Cys Leu Val Leu Leu Pro Phe Leu Ala
35 40 45

```
Gly Leu Thr Thr Tyr Leu Leu Val Ser Gln Leu Arg Ala Gln Gly Glu
    50                  55                  60

Ala Cys Val Gln Leu Gln Asp Leu Lys Gly Gln Glu Phe Ala Pro Ser
65                  70                  75                  80

His Gln Gln Val Tyr Ala Pro Leu Arg Ala Asp Gly Asp Lys Pro Arg
                85                  90                  95

Ala His Leu Thr Val Val Arg Gln Thr Pro Thr Gln His Leu Lys Asn
            100                 105                 110

Gln Phe Pro Ala Leu His Trp Glu His Glu Leu Gly Leu Ala Phe Thr
        115                 120                 125

Lys Asn Arg Met Asn Tyr Thr Asn Lys Phe Leu Leu Ile Pro Glu Ser
    130                 135                 140

Gly Asp Tyr Phe Val Tyr Ser Gln Val Thr Phe Arg Gly Met Thr Ser
145                 150                 155                 160

Glu Cys Ser Glu Ile Arg Gln Ala Gly Arg Pro Asn Lys Pro Asp Ser
                165                 170                 175

Ile Thr Val Val Ile Thr Lys Val Thr Asp Ser Tyr Pro Glu Pro Thr
            180                 185                 190

Gln Leu Leu Met Gly Thr Lys Ser Val Cys Glu Val Gly Ser Asn Trp
        195                 200                 205

Phe Gln Pro Ile Tyr Leu Gly Ala Met Phe Ser Leu Gln Glu Gly Asp
    210                 215                 220

Lys Leu Met Val Asn Val Ser Asp Ile Ser Leu Val Asp Tyr Thr Lys
225                 230                 235                 240

Glu Asp Lys Thr Phe Phe Gly Ala Phe Leu Leu
                245                 250


<210> SEQ ID NO 5
<211> LENGTH: 540
<212> TYPE: DNA
<213> ORGANISM: rhesus macaque

<400> SEQUENCE: 5

aaaggacagg agtttgcacc ttcacatcag caagtttatg cacctcttag agcagacgga     60

gataagccaa gggcacacct gacagttgtg acacaaactc ccacacagca ctttaaaaat    120

cagttcccag ctctgcactg ggaacatgaa ctaggcctgg ccttcaccaa gaaccgaatg    180

aactatacca acaaattcct gctgatccca gagtcgggag actacttcat ttactcccag    240

gtcacattcc gtgggatgac ctctgagtgc agtgaaatca gacaagcagg ccgaccaaac    300

aagccagact ccatcactgt ggtcatcacc aaggtaacag acagctaccc tgagccaacc    360

cagctcctca tggggaccaa gtctgtgtgc gaagtaggta gcaactggtt ccagcccatc    420

tacctcggac ccatgttctc cttgcaagaa ggggacaagc taatggtgaa cgtcagtgac    480

atctccttgg tggattacac aaaagaagat aaaaccttct ttggagcctt cttactatag    540


<210> SEQ ID NO 6
<211> LENGTH: 179
<212> TYPE: PRT
<213> ORGANISM: rhesus macaque

<400> SEQUENCE: 6

Lys Gly Gln Glu Phe Ala Pro Ser His Gln Gln Val Tyr Ala Pro Leu
1               5                   10                  15

Arg Ala Asp Gly Asp Lys Pro Arg Ala His Leu Thr Val Val Thr Gln
            20                  25                  30
```

```
Thr Pro Thr Gln His Phe Lys Asn Gln Phe Pro Ala Leu His Trp Glu
        35                  40                  45

His Glu Leu Gly Leu Ala Phe Thr Lys Asn Arg Met Asn Tyr Thr Asn
    50                  55                  60

Lys Phe Leu Leu Ile Pro Glu Ser Gly Asp Tyr Phe Ile Tyr Ser Gln
65                  70                  75                  80

Val Thr Phe Arg Gly Met Thr Ser Glu Cys Ser Glu Ile Arg Gln Ala
                85                  90                  95

Gly Arg Pro Asn Lys Pro Asp Ser Ile Thr Val Val Ile Thr Lys Val
            100                 105                 110

Thr Asp Ser Tyr Pro Glu Pro Thr Gln Leu Leu Met Gly Thr Lys Ser
        115                 120                 125

Val Cys Glu Val Gly Ser Asn Trp Phe Gln Pro Ile Tyr Leu Gly Pro
    130                 135                 140

Met Phe Ser Leu Gln Glu Gly Asp Lys Leu Met Val Asn Val Ser Asp
145                 150                 155                 160

Ile Ser Leu Val Asp Tyr Thr Lys Glu Asp Lys Thr Phe Phe Gly Ala
                165                 170                 175

Phe Leu Leu


<210> SEQ ID NO 7
<211> LENGTH: 675
<212> TYPE: DNA
<213> ORGANISM: rhesus macaque

<400> SEQUENCE: 7

ataaaaacat gtggtggtgg cagcaaacct cccacgtgcc caccgtgccc agcacctgaa     60

ctcctggggg gaccgtcagt cttcctcttc cccccaaaac ccaaggacac cctcatgatc    120

tcccggaccc ctgaggtcac atgcgtggtg gtagacgtga gccaggaaga ccccgatgtc    180

aagttcaact ggtacgtaaa cggcgcggag gtgcatcatg cccagacgaa gccacgggag    240

acgcagtaca acagcacata tcgtgtggtc agcgtcctca ccgtcacgca ccaggactgg    300

ctgaacggca aggagtacac gtgcaaggtc tccaacaaag ccctcccggt ccccatccag    360

aaaaccatct ccaaagacaa agggcagccc cgagagcctc aggtgtacac cctgcccccg    420

tcccgggagg agctgaccaa gaaccaggtc agcctgacct gcctggtcaa aggcttctac    480

cccagcgaca tcgtcgtgga gtgggagaac agcgggcagc cggagaacac ctacaagacc    540

accccgcccg tgctggactc cgacggctcc tacttcctct acagcaagct caccgtggac    600

aagagcaggt ggcagcaggg gaacgtcttc tcatgctccg tgatgcatga ggctctgcac    660

aaccactaca cgcag                                                     675


<210> SEQ ID NO 8
<211> LENGTH: 225
<212> TYPE: PRT
<213> ORGANISM: rhesus macaque

<400> SEQUENCE: 8

Ile Lys Thr Cys Gly Gly Gly Ser Lys Pro Pro Thr Cys Pro Pro Cys
1               5                   10                  15

Pro Ala Pro Glu Leu Leu Gly Gly Pro Ser Val Phe Leu Phe Pro Pro
            20                  25                  30

Lys Pro Lys Asp Thr Leu Met Ile Ser Arg Thr Pro Glu Val Thr Cys
        35                  40                  45
```

```
Val Val Val Asp Val Ser Gln Glu Asp Pro Asp Val Lys Phe Asn Trp
    50                  55                  60

Tyr Val Asn Gly Ala Glu Val His His Ala Gln Thr Lys Pro Arg Glu
65                  70                  75                  80

Thr Gln Tyr Asn Ser Thr Tyr Arg Val Val Ser Val Leu Thr Val Thr
                85                  90                  95

His Gln Asp Trp Leu Asn Gly Lys Glu Tyr Thr Cys Lys Val Ser Asn
            100                 105                 110

Lys Ala Leu Pro Val Pro Ile Gln Lys Thr Ile Ser Lys Asp Lys Gly
        115                 120                 125

Gln Pro Arg Glu Pro Gln Val Tyr Thr Leu Pro Pro Ser Arg Glu Glu
    130                 135                 140

Leu Thr Lys Asn Gln Val Ser Leu Thr Cys Leu Val Lys Gly Phe Tyr
145                 150                 155                 160

Pro Ser Asp Ile Val Val Glu Trp Glu Asn Ser Gly Gln Pro Glu Asn
                165                 170                 175

Thr Tyr Lys Thr Thr Pro Pro Val Leu Asp Ser Asp Gly Ser Tyr Phe
            180                 185                 190

Leu Tyr Ser Lys Leu Thr Val Asp Lys Ser Arg Trp Gln Gln Gly Asn
        195                 200                 205

Val Phe Ser Cys Ser Val Met His Glu Ala Leu His Asn His Tyr Thr
    210                 215                 220

Gln
225


<210> SEQ ID NO 9
<211> LENGTH: 1290
<212> TYPE: DNA
<213> ORGANISM: Artificial Sequence
<220> FEATURE:
<223> OTHER INFORMATION: synthetic oligonucleotide

<400> SEQUENCE: 9

atggagacag acacactcct gctatgggta ctgctgctct gggttccagg ttccactggt     60

gacctcgaga taaaaacatg tggtggtggc agcaaacctc ccacgtgccc accgtgccca    120

gcacctgaac tcctgggggg accgtcagtc ttcctcttcc ccccaaaacc caaggacacc    180

ctcatgatct cccggacccc tgaggtcaca tgcgtggtgg tagacgtgag ccaggaagac    240

cccgatgtca agttcaactg gtacgtaaac ggcgcggagg tgcatcatgc ccagacgaag    300

ccacgggaga cgcagtacaa cagcacatat cgtgtggtca gcgtcctcac cgtcacgcac    360

caggactggc tgaacggcaa ggagtacacg tgcaaggtct ccaacaaagc cctcccggtc    420

cccatccaga aaaccatctc caaagacaaa gggcagcccc gagagcctca ggtgtacacc    480

ctgcccccgt cccgggagga gctgaccaag aaccaggtca gcctgacctg cctggtcaaa    540

ggcttctacc ccagcgacat cgtcgtggag tgggagaaca gcgggcagcc ggagaacacc    600

tacaagacca ccccgcccgt gctggactcc gacggctcct acttcctcta cagcaagctc    660

accgtggaca agagcaggtg gcagcagggg aacgtcttct catgctccgt gatgcatgag    720

gctctgcaca accactacac gcaggaattc aaaggacagg agtttgcacc ttcacatcag    780

caagtttatg cacctcttag agcagacgga gataagccaa gggcacacct gacagttgtg    840

acacaaactc ccacacagca ctttaaaaat cagttcccag ctctgcactg ggaacatgaa    900

ctaggcctgg ccttcaccaa gaaccgaatg aactatacca acaaattcct gctgatccca    960

gagtcgggag actacttcat ttactcccag gtcacattcc gtgggatgac ctctgagtgc   1020
```

```
agtgaaatca gacaagcagg ccgaccaaac aagccagact ccatcactgt ggtcatcacc   1080

aaggtaacag acagctaccc tgagccaacc cagctcctca tggggaccaa gtctgtgtgc   1140

gaagtaggta gcaactggtt ccagcccatc tacctcggac ccatgttctc cttgcaagaa   1200

ggggacaagc taatggtgaa cgtcagtgac atctccttgg tggattacac aaaagaagat   1260

aaaaccttct ttggagcctt cttactatag                                    1290


<210> SEQ ID NO 10
<211> LENGTH: 429
<212> TYPE: PRT
<213> ORGANISM: Artificial Sequence
<220> FEATURE:
<223> OTHER INFORMATION: synthetic peptide

<400> SEQUENCE: 10

Met Glu Thr Asp Thr Leu Leu Leu Trp Val Leu Leu Leu Trp Val Pro
1               5                   10                  15

Gly Ser Thr Gly Asp Leu Glu Ile Lys Thr Cys Gly Gly Gly Ser Lys
            20                  25                  30

Pro Pro Thr Cys Pro Pro Cys Pro Ala Pro Glu Leu Leu Gly Gly Pro
        35                  40                  45

Ser Val Phe Leu Phe Pro Pro Lys Pro Lys Asp Thr Leu Met Ile Ser
    50                  55                  60

Arg Thr Pro Glu Val Thr Cys Val Val Val Asp Val Ser Gln Glu Asp
65                  70                  75                  80

Pro Asp Val Lys Phe Asn Trp Tyr Val Asn Gly Ala Glu Val His His
                85                  90                  95

Ala Gln Thr Lys Pro Arg Glu Thr Gln Tyr Asn Ser Thr Tyr Arg Val
            100                 105                 110

Val Ser Val Leu Thr Val Thr His Gln Asp Trp Leu Asn Gly Lys Glu
        115                 120                 125

Tyr Thr Cys Lys Val Ser Asn Lys Ala Leu Pro Val Pro Ile Gln Lys
    130                 135                 140

Thr Ile Ser Lys Asp Lys Gly Gln Pro Arg Glu Pro Gln Val Tyr Thr
145                 150                 155                 160

Leu Pro Pro Ser Arg Glu Glu Leu Thr Lys Asn Gln Val Ser Leu Thr
                165                 170                 175

Cys Leu Val Lys Gly Phe Tyr Pro Ser Asp Ile Val Val Glu Trp Glu
            180                 185                 190

Asn Ser Gly Gln Pro Glu Asn Thr Tyr Lys Thr Thr Pro Pro Val Leu
        195                 200                 205

Asp Ser Asp Gly Ser Tyr Phe Leu Tyr Ser Lys Leu Thr Val Asp Lys
    210                 215                 220

Ser Arg Trp Gln Gln Gly Asn Val Phe Ser Cys Ser Val Met His Glu
225                 230                 235                 240

Ala Leu His Asn His Tyr Thr Gln Glu Phe Lys Gly Gln Glu Phe Ala
                245                 250                 255

Pro Ser His Gln Gln Val Tyr Ala Pro Leu Arg Ala Asp Gly Asp Lys
            260                 265                 270

Pro Arg Ala His Leu Thr Val Val Thr Gln Thr Pro Thr Gln His Phe
        275                 280                 285

Lys Asn Gln Phe Pro Ala Leu His Trp Glu His Glu Leu Gly Leu Ala
    290                 295                 300

Phe Thr Lys Asn Arg Met Asn Tyr Thr Asn Lys Phe Leu Leu Ile Pro
305                 310                 315                 320
```

```
Glu Ser Gly Asp Tyr Phe Ile Tyr Ser Gln Val Thr Phe Arg Gly Met
                325                 330                 335

Thr Ser Glu Cys Ser Glu Ile Arg Gln Ala Gly Arg Pro Asn Lys Pro
            340                 345                 350

Asp Ser Ile Thr Val Val Ile Thr Lys Val Thr Asp Ser Tyr Pro Glu
        355                 360                 365

Pro Thr Gln Leu Leu Met Gly Thr Lys Ser Val Cys Glu Val Gly Ser
    370                 375                 380

Asn Trp Phe Gln Pro Ile Tyr Leu Gly Pro Met Phe Ser Leu Gln Glu
385                 390                 395                 400

Gly Asp Lys Leu Met Val Asn Val Ser Asp Ile Ser Leu Val Asp Tyr
                405                 410                 415

Thr Lys Glu Asp Lys Thr Phe Phe Gly Ala Phe Leu Leu
            420                 425


<210> SEQ ID NO 11
<211> LENGTH: 579
<212> TYPE: DNA
<213> ORGANISM: Homo sapiens

<400> SEQUENCE: 11

cgggcccagg gagaggcctg tgtgcagttc caggctctaa aaggacagga gtttgcacct     60

tcacatcagc aagtttatgc acctcttaga gcagacggag ataagccaag ggcacacctg    120

acagttgtga gacaaactcc cacacagcac tttaaaaatc agttcccagc tctgcactgg    180

gaacatgaac taggcctggc cttcaccaag aaccgaatga actataccaa caaattcctg    240

ctgatcccag agtcgggaga ctacttcatt tactcccagg tcacattccg tgggatgacc    300

tctgagtgca gtgaaatcag acaagcaggc cgaccaaaca agccagactc catcactgtg    360

gtcatcacca aggtaacaga cagctaccct gagccaaccc agctcctcat ggggaccaag    420

tctgtgtgcg aagtaggtag caactggttc cagcccatct acctcggagc catgttctcc    480

ttgcaagaag gggacaagct aatggtgaac gtcagtgaca tctctttggt ggattacaca    540

aaagaagata aaaccttctt tggagccttc ttactatag                           579


<210> SEQ ID NO 12
<211> LENGTH: 192
<212> TYPE: PRT
<213> ORGANISM: Homo sapiens

<400> SEQUENCE: 12

Arg Ala Gln Gly Glu Ala Cys Val Gln Phe Gln Ala Leu Lys Gly Gln
1               5                   10                  15

Glu Phe Ala Pro Ser His Gln Gln Val Tyr Ala Pro Leu Arg Ala Asp
            20                  25                  30

Gly Asp Lys Pro Arg Ala His Leu Thr Val Val Arg Gln Thr Pro Thr
        35                  40                  45

Gln His Phe Lys Asn Gln Phe Pro Ala Leu His Trp Glu His Glu Leu
    50                  55                  60

Gly Leu Ala Phe Thr Lys Asn Arg Met Asn Tyr Thr Asn Lys Phe Leu
65                  70                  75                  80

Leu Ile Pro Glu Ser Gly Asp Tyr Phe Ile Tyr Ser Gln Val Thr Phe
                85                  90                  95

Arg Gly Met Thr Ser Glu Cys Ser Glu Ile Arg Gln Ala Gly Arg Pro
            100                 105                 110
```

```
Asn Lys Pro Asp Ser Ile Thr Val Val Ile Thr Lys Val Thr Asp Ser
        115                 120                 125

Tyr Pro Glu Pro Thr Gln Leu Leu Met Gly Thr Lys Ser Val Cys Glu
    130                 135                 140

Val Gly Ser Asn Trp Phe Gln Pro Ile Tyr Leu Gly Ala Met Phe Ser
145                 150                 155                 160

Leu Gln Glu Gly Asp Lys Leu Met Val Asn Val Ser Asp Ile Ser Leu
                165                 170                 175

Val Asp Tyr Thr Lys Glu Asp Lys Thr Phe Phe Gly Ala Phe Leu Leu
            180                 185                 190


<210> SEQ ID NO 13
<211> LENGTH: 684
<212> TYPE: DNA
<213> ORGANISM: Homo sapiens

<400> SEQUENCE: 13

tgtgacaaaa ctcacacatg cccaccgtgc ccagcacctg aactcctggg gggaccgtca     60

gtcttcctct tccccccaaa acccaaggac accctcatga tctcccggac ccctgaggtc    120

acatgcgtgg tggtggacgt gagccacgaa gaccctgagg tcaagttcaa ctggtacgtg    180

gacggcgtgg aggtgcataa tgccaagaca aagccgcggg aggagcagta caacagcacg    240

taccgtgtgg tcagcgtcct caccgtcctg caccaggact ggctgaatgg caaggagtac    300

aagtgcaagg tctccaacaa agccctccca gcccccatcg agaaaaccat ctccaaagcc    360

aaagggcagc cccgagaacc acaggtgtac accctgcccc catcccggga tgagctgacc    420

aagaaccagg tcagcctgac ctgcctggtc aaaggcttct atcccagcga catcgccgtg    480

gagtgggaga gcaatgggca gccggagaac aactacaaga ccacgcctcc cgtgctggac    540

tccgacggct ccttcttcct ctacagcaag ctcaccgtgg acaagagcag gtggcagcag    600

gggaacgtct tctcatgctc cgtgatgcat gaggctctgc acaaccacta cacgcagaag    660

agcctctccc tgtctccggg taaa                                           684


<210> SEQ ID NO 14
<211> LENGTH: 228
<212> TYPE: PRT
<213> ORGANISM: Homo sapiens

<400> SEQUENCE: 14

Cys Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125
```

```
Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225


<210> SEQ ID NO 15
<211> LENGTH: 1269
<212> TYPE: DNA
<213> ORGANISM: Artificial Sequence
<220> FEATURE:
<223> OTHER INFORMATION: synthetic oligonucleotide

<400> SEQUENCE: 15

tgtgacaaaa ctcacacatg cccaccgtgc ccagcacctg aactcctggg gggaccgtca     60

gtcttcctct tccccccaaa acccaaggac accctcatga tctcccggac ccctgaggtc    120

acatgcgtgg tggtggacgt gagccacgaa gaccctgagg tcaagttcaa ctggtacgtg    180

gacggcgtgg aggtgcataa tgccaagaca aagccgcggg aggagcagta caacagcacg    240

taccgtgtgg tcagcgtcct caccgtcctg caccaggact ggctgaatgg caaggagtac    300

aagtgcaagg tctccaacaa agccctccca gcccccatcg agaaaaccat ctccaaagcc    360

aaagggcagc cccgagaacc acaggtgtac accctgcccc catcccggga tgagctgacc    420

aagaaccagg tcagcctgac ctgcctggtc aaaggcttct atcccagcga catcgccgtg    480

gagtgggaga gcaatgggca gccggagaac aactacaaga ccacgcctcc cgtgctggac    540

tccgacggct ccttcttcct ctacagcaag ctcaccgtgg acaagagcag gtggcagcag    600

gggaacgtct tctcatgctc cgtgatgcat gaggctctgc acaaccacta cacgcagaag    660

agcctctccc tgtctccggg taaagaattc cgggcccagg gagaggcctg tgtgcagttc    720

caggctctaa aaggacagga gtttgcacct tcacatcagc aagtttatgc acctcttaga    780

gcagacggag ataagccaag ggcacacctg acagttgtga gacaaactcc cacacagcac    840

tttaaaaatc agttcccagc tctgcactgg gaacatgaac taggcctggc cttcaccaag    900

aaccgaatga actataccaa caaattcctg ctgatcccag agtcgggaga ctacttcatt    960

tactcccagg tcacattccg tgggatgacc tctgagtgca gtgaaatcag acaagcaggc   1020

cgaccaaaca agccagactc catcactgtg gtcatcacca aggtaacaga cagctaccct   1080

gagccaaccc agctcctcat ggggaccaag tctgtgtgcg aagtaggtag caactggttc   1140

cagcccatct acctcggagc catgttctcc ttgcaagaag gggacaagct aatggtgaac   1200

gtcagtgaca tctctttggt ggattacaca aaagaagata aaaccttctt tggagccttc   1260

ttactatag                                                           1269
```

<210> SEQ ID NO 16
<211> LENGTH: 422
<212> TYPE: PRT
<213> ORGANISM: Artificial Sequence
<220> FEATURE:
<223> OTHER INFORMATION: synthetic peptide

<400> SEQUENCE: 16

Cys Asp Lys Thr His Thr Cys Pro Pro Cys Pro Ala Pro Glu Leu Leu
1 5 10 15

Gly Gly Pro Ser Val Phe Leu Phe Pro Pro Lys Pro Lys Asp Thr Leu
20 25 30

Met Ile Ser Arg Thr Pro Glu Val Thr Cys Val Val Val Asp Val Ser
35 40 45

His Glu Asp Pro Glu Val Lys Phe Asn Trp Tyr Val Asp Gly Val Glu
50 55 60

Val His Asn Ala Lys Thr Lys Pro Arg Glu Glu Gln Tyr Asn Ser Thr
65 70 75 80

Tyr Arg Val Val Ser Val Leu Thr Val Leu His Gln Asp Trp Leu Asn
85 90 95

Gly Lys Glu Tyr Lys Cys Lys Val Ser Asn Lys Ala Leu Pro Ala Pro
100 105 110

Ile Glu Lys Thr Ile Ser Lys Ala Lys Gly Gln Pro Arg Glu Pro Gln
115 120 125

Val Tyr Thr Leu Pro Pro Ser Arg Asp Glu Leu Thr Lys Asn Gln Val
130 135 140

Ser Leu Thr Cys Leu Val Lys Gly Phe Tyr Pro Ser Asp Ile Ala Val
145 150 155 160

Glu Trp Glu Ser Asn Gly Gln Pro Glu Asn Asn Tyr Lys Thr Thr Pro
165 170 175

Pro Val Leu Asp Ser Asp Gly Ser Phe Phe Leu Tyr Ser Lys Leu Thr
180 185 190

Val Asp Lys Ser Arg Trp Gln Gln Gly Asn Val Phe Ser Cys Ser Val
195 200 205

Met His Glu Ala Leu His Asn His Tyr Thr Gln Lys Ser Leu Ser Leu
210 215 220

Ser Pro Gly Lys Glu Phe Arg Ala Gln Gly Glu Ala Cys Val Gln Phe
225 230 235 240

Gln Ala Leu Lys Gly Gln Glu Phe Ala Pro Ser His Gln Gln Val Tyr
245 250 255

Ala Pro Leu Arg Ala Asp Gly Asp Lys Pro Arg Ala His Leu Thr Val
260 265 270

Val Arg Gln Thr Pro Thr Gln His Phe Lys Asn Gln Phe Pro Ala Leu
275 280 285

His Trp Glu His Glu Leu Gly Leu Ala Phe Thr Lys Asn Arg Met Asn
290 295 300

Tyr Thr Asn Lys Phe Leu Leu Ile Pro Glu Ser Gly Asp Tyr Phe Ile
305 310 315 320

Tyr Ser Gln Val Thr Phe Arg Gly Met Thr Ser Glu Cys Ser Glu Ile
325 330 335

Arg Gln Ala Gly Arg Pro Asn Lys Pro Asp Ser Ile Thr Val Val Ile
340 345 350

Thr Lys Val Thr Asp Ser Tyr Pro Glu Pro Thr Gln Leu Leu Met Gly
355 360 365

-continued

```
Thr Lys Ser Val Cys Glu Val Gly Ser Asn Trp Phe Gln Pro Ile Tyr
    370                 375                 380

Leu Gly Ala Met Phe Ser Leu Gln Glu Gly Asp Lys Leu Met Val Asn
385                 390                 395                 400

Val Ser Asp Ile Ser Leu Val Asp Tyr Thr Lys Glu Asp Lys Thr Phe
                405                 410                 415

Phe Gly Ala Phe Leu Leu
            420
```

What is claimed is:

1. A composition comprising (i) a human TL1A-Ig fusion protein, the fusion protein comprising (a) a first polypeptide comprising an extracellular domain of a human TL1A polypeptide or a fragment thereof that specifically binds to Tumor Necrosis Factor Receptor Superfamily, Member 25 (TNFRSF25); and (b) a second polypeptide comprising an immunoglobulin (Ig) polypeptide; and (ii) one or both of an effective amount of interleukin (IL)-2 and an effective amount of an mTOR inhibitor.

2. The composition of claim 1, wherein, when administered to a human in need thereof, the composition reduces the frequency of naive CD4 T cells in the human.

3. The composition of claim 1, wherein the first polypeptide comprises (a) the amino acid sequence of SEQ ID NO 12, or (b) an amino acid sequence that has at least 90% sequence identity to SEQ ID NO 12.

4. The composition of claim 1, wherein the fusion protein is a homomultimer, and wherein the homomultimer is a dimer of trimers.

5. The composition of claim 1, wherein the Ig polypeptide comprises one or more of a hinge region, a CH2 domain, and a CH3 domain of an IgG polypeptide.

6. The composition claim 1, wherein the Ig polypeptide comprises (a) the amino acid sequence of SEQ ID NO 14, or (b) an amino acid sequence that has at least 90% sequence identity to SEQ ID NO 14.

7. The composition of claim 1, wherein the fusion protein comprises (a) the amino acid sequence of SEQ ID NO 16, or (b) an amino acid sequence that has at least 90% sequence identity to SEQ ID NO 16.

8. The composition of claim 1, wherein the in vivo efficacy of the composition is higher than the in vivo efficacy of the first polypeptide when it is not coupled with an Ig polypeptide.

9. The composition of claim 1, wherein the effective amount of IL-2 is an amount that, in combination with the TL1A-Ig fusion protein, is sufficient to achieve a synergistic effect on the expansion of Treg cells when administered to a subject.

10. The composition of claim 1, wherein the effective amount of IL-2 is a dose of IL-2 that would induce suboptimal, or fail to induce, expansion of Treg cells if administered alone to a human patient.

11. The composition of claim 10, wherein the dose of IL-2 is less than 1 million units per square meter per day.

12. The composition of claim 11, wherein the dose of IL-2 is an amount in the range of about 30,000 to about 300,000 units per square meter per day.

13. The composition of claim 12, wherein the dose of IL-2 is about 300,000 units per square meter per day.

14. The composition of claim 12, wherein the dose of IL-2 is about 30,000 units per square meter per day.

15. The composition of claim 1, wherein the mTOR inhibitor is selected from the group consisting of rapamycin (sirolimus), CI-779, everolimus ABT-578, tacrolimus, AP-23675, BEZ-235, OSI-027, QLT-0447, ABI-009, BC-210, salirasib, TAFA-93, deforolimus (AP-23573), temsirolimus, 2-(4-Amino-1-isopropyl-1H-pyrazolo[3,4-d]pyrimidin-3-yl)-1H-indol-5-ol (PP242), AP-23841, 32-deoxorapamycin, 16-pent-2-ynyloxy-32-deoxorapamycin, 16-pent-2-ynyloxy-32(S or R)-dihydro-rapamycin, 16-pent-2-ynyloxy-32(S or R)-dihydro-40-O-(2-hydroxyethyl)-rapamycin, 40-[3-hydroxy-2-(hydroxymethyl)-2-methylpropanoate]-rapamycin (CCI779), 40-epi-(tetrazolyl)-rapamycin (ABT578), biolimus-7, biolimus-9, and AP23464.

16. The composition of claim 15, wherein the mTOR inhibitor is rapamycin.

17. The composition of claim 16, wherein the effective amount of rapamycin is a dosage between about 25 μg/kg and about 500 μg/kg.

18. The composition of claim 1, wherein the composition comprises the fusion protein and the IL-2.

19. The composition of claim 1, wherein the composition comprises the fusion protein and the mTOR inhibitor.

*20. A method of increasing the frequency of FoxP3+CD4+ Treg cells out of total CD4+ cells in a patient, the method comprising:*

*(a) administering a fusion protein to the patient, the fusion protein comprising, from N- to C-terminal:*

*i) a human IgG domain, and*

*ii) a human TL1A extracellular domain that specifically binds to Tumor Necrosis Factor Receptor Superfamily Member 25 (TNFRSF25); and*

*(b) administering to the patient an effective amount of IL-2.*

*21. The method of claim 20, wherein an effective amount of IL-2 is an amount that, in combination with the fusion protein, is sufficient to achieve a synergistic effect on the expansion of Treg cells when administered to a subject.*

*22. The method of claim 20, wherein an effective amount of IL-2 is a dose of IL-2 that induces suboptimal, or fails to induce, expansion of Treg cells if administered alone to a human patient.*

*23. The method of claim 22, wherein the dose of IL-2 is less than 1 million units per square meter per day.*

*24. The method of claim 23, wherein the dose of IL-2 is an amount in the range of about 30,000 to about 300,000 units per square meter per day.*

*25. The method of claim 23, wherein the dose of IL-2 is about 300,000 units per square meter per day.*

*26. The method of claim 23, wherein the dose of IL-2 is about 30,000 units per square meter per day.*

*27. A method of decreasing the frequency and/or expansion of effector T cells in a patient, the method comprising:*

(*a*) *administering to the patient a fusion protein, the fusion protein comprising, from N- to C-terminal:*

*i*) *a human IgG domain, and*

*ii*) *a human TL1A extracellular domain that specifically binds to Tumor Necrosis Factor Receptor Superfamily Member 25* (*TNFRSF25*)*; and*

(*b*) *administering to the patient an effective amount of an mTOR inhibitor.*

*28. The method of claim 27, wherein the mTOR inhibitor is selected from the group consisting of rapamycin* (*sirolimus*)*, CI-779, everolimus ABT-578, tacrolimus, AP-23675, BEZ-235, OSI-027, QLT-0447, ABI-009, BC-210, salirasib, TAFA-93, deforolimus* (*AP-23573*)*, temsirolimus, 2-*(*4-Amino-1-isopropyl-1H-pyrazolo*[*3,4-d*]*pyrimidin-3-yl*)*-1H-indol-5-ol* (*PP242*)*, AP-23841, 32-deoxorapamycin, 16-pent-2-ynyloxy-32-deoxorapamycin, 16-pent-2-ynyloxy-32*(*S or R*)*-dihydro-rapamycin, 16-pent-2-ynyloxy-32*(*S or R*)*-dihydro-40-O-*(*2-hydroxyethyl*)*-rapamycin, 40-*[*3-hydroxy-2-*(*hydroxymethyl*)*-2-methylpropanoate*]*-rapamycin* (*CCI779*)*, 40-epi-*(*tetrazolyl*)*-rapamycin* (*ABT578*)*, biolimus-7, biolimus-9, and AP23464.*

*29. A method of claim 28, wherein the mTOR inhibitor is rapamycin.*

*30. A method of claim 29, wherein the effective amount of rapamycin is between about 25 μg/kg and about 500 μg/kg.*

* * * * *